US008815586B2

(12) United States Patent
Corey et al.

(10) Patent No.: US 8,815,586 B2
(45) Date of Patent: Aug. 26, 2014

(54) MODULATION OF GENE EXPRESSION USING OLIGOMERS THAT TARGET GENE REGIONS DOWNSTREAM OF 3' UNTRANSLATED REGIONS

(75) Inventors: David R. Corey, Dallas, TX (US); Xuan Yue, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 12/766,574

(22) Filed: Apr. 23, 2010

(65) Prior Publication Data

US 2010/0273863 A1    Oct. 28, 2010

Related U.S. Application Data

(60) Provisional application No. 61/172,528, filed on Apr. 24, 2009, provisional application No. 61/227,952, filed on Jul. 23, 2009.

(51) Int. Cl.
| C12Q 1/68 | (2006.01) |
| C12N 5/00 | (2006.01) |
| C12P 19/34 | (2006.01) |
| C07H 21/02 | (2006.01) |
| C07H 21/04 | (2006.01) |

(52) U.S. Cl.
USPC ........... 435/375; 435/6; 435/91.1; 435/91.31; 435/455; 514/44; 536/23.1; 536/24.5

(58) Field of Classification Search
USPC ............ 435/6, 91.1, 91.31, 455, 375; 514/44; 536/23.1, 24.5
See application file for complete search history.

(56) References Cited

U.S. PATENT DOCUMENTS

| 5,000,000 | A  | * | 3/1991 | Ingram et al. ................. 435/161 |
| 5,859,221 | A  |   | 1/1999 | Cook et al. .................... 536/23.1 |
| 5,877,160 | A  |   | 3/1999 | Harper et al. ................... 514/44 |
| 6,506,559 | B1 |   | 1/2003 | Fire et al. ........................... 435/6 |
| 6,673,611 | B2 |   | 1/2004 | Thompson et al. ........... 435/455 |
| 6,867,349 | B2 |   | 3/2005 | Ekker et al. ..................... 800/21 |
| 2003/0143732 | A1 | | 7/2003 | Fosnaugh et al. .............. 514/44 |
| 2004/0259247 | A1 | | 12/2004 | Tuschl et al. ................. 536/24.5 |
| 2005/0032733 | A1 | | 2/2005 | McSwiggen et al. ........... 514/44 |
| 2006/0205635 | A1 | | 9/2006 | Corey et al. ..................... 514/44 |
| 2007/0111963 | A1 | | 5/2007 | Corey et al. ..................... 514/44 |
| 2009/0004668 | A1 | * | 1/2009 | Chen et al. ......................... 435/6 |

FOREIGN PATENT DOCUMENTS

| WO | WO 97/32024 | 9/1997 |
| WO | WO 01/75164 | 10/2001 |
| WO | WO 01/83793 | 11/2001 |
| WO | WO 03/070918 | 8/2003 |
| WO | WO 2004/020631 | 3/2004 |
| WO | WO 2006/113246 | 10/2006 |
| WO | WO 2009/046397 | 4/2009 |

OTHER PUBLICATIONS

Wahlestedt, C., Drug Discovery Today, vol. 11, No. 11-12, pp. 503-508 (2006).*
Doench et al., Genes & Dev., vol. 18, No. 5, pp. 504-511 (2004).*
Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Opalinska et al., Nature Rev., vol. 1, pp. 503-514 (2002).*
Jang et al., Expert Rev. Medical Devices, vol. 1, No. 1, pp. 127-138 (2004).*
Janowski et al., Nature Chem. Biol., vol. 3, No. 3, pp. 166-173 (2007).*
Paroo et al., Trends in Biotech., vol. 22, No. 8, pp. 390-394 (2004).*
International Search Report and Written Opinion issued in PCT/US2010/032271, dated Nov. 5, 2010.
Tan-Wong et al., "Dynamic interactions between the promoter and terminator regions of the mammalian BRCA1 gene," *Proc. Natl. Acad. of Sci.*, 105: 5160-5165, 2008.
Yue et al., "Transcriptional regulation by small RNAs at sequences downstream from 3' gene termini," *Nature Chemical Biology*, 6: 621-629, 2010.
Affymetrix/Cold Spring Harbor Laboratory ENCODE Transcriptome Project, "Post-transcriptional processing generates a diversity of 5'-modified long and short RNAs," *Nature*, 457:1028-1032, 2009.
Aartsma-Rus and vanOmmen, "Antisense-mediated exon skipping: a versatile tool with therapeutic and research applications," *RNA*, 13:1609-1624, 2007.
Amaral and Mattick, "Noncoding RNA in development," *Mamm. Genome*, 19:454-492, 2008.
Braasch et al., "RNA interference in mammalian cells by chemically-modified RNA," *Biochemistry*, 42:7967-7975, 2003.
Check, "RNA interference: hitting the on switch," *Nature*, 448(7156):855-858, 2007.
Chen et al., "A systematic analysis of disease-associated variants in the 3' regulatory regions of human protein-coding genes II: the importance of mRNA secondary structure in assessing the functionality of 3' UTR variants," *Hum. Gen.*, 120:301-333, 2006.
Corey, "RNA learns from antisense," *Nat. Chem. Biol.*, 3:8-11, 2007.
Czauderna et al. "Structural variations and stabilising modifications of synthetic siRNAs in mammalian cells," *Nucleic Acids Res.*, 31(11):2705-2716, 2003.
Elmén et al., "Locked nucleic acid (LNA) mediated improvements in siRNA stability and functionality," *Nucleic Acids Res.*, 33(1):439-447, 2005.
Gingeras, "Origin of phenotypes: genes and transcripts," *Genome Res.*, 17:682-690, 2007.
Goodrich and Kugel, "From bacteria to humans, chromatin to elongation, and activation to repression: The expanding roles of noncoding RNAs in regulating transcription," *Crit. Rev. Biochem. Mol. Biol.*, 44:3-15, 2009.

(Continued)

*Primary Examiner* — Jane Zara
(74) *Attorney, Agent, or Firm* — Parker Highlander PLLC

(57) ABSTRACT

Gene expression can be selectively modulated by contacting a cell with an oligomer that targets a gene region downstream of a '3-UTR, thereby increasing or decreasing the expression of the target gene.

28 Claims, 39 Drawing Sheets

(56) References Cited

OTHER PUBLICATIONS

Griffiths-Jones et al., "miRBase: microRNA sequences, targets and gene nomenclature," *Nucleic Acids Res.*, 34:D140-4, 2006.
Griffiths-Jones et al., "miRBase: tools for microRNA genomics," *Nucleic Acids Res.*, 36:D154-8, 2008.
Griffiths-Jones, "The microRNA Registry," *Nucleic Acids Res.*, 32:D109-11, 2004.
Grimson et al., "MicroRNA targeting specificity in mammals: determinants beyond seed pairing," *Mol. Cell.*, 27:91-105, 2007.
Han et al., "Promoter-associated RNA is required for RNA-directed transcriptional gene silencing in human cells," *Proc. Natl. Acad. USA*, 104:12422-12427, 2007.
He et al., "The antisense transcriptomes of human cells," *Science*, 322:1855-7, 2008.
Hwang et al., "A Flexanucleotide element directs microRNA nuclear import," *Science*, 315:97-100, 2007.
Janowski et al., "Activating gene expression in mammalian cells with promoter-targeted duplex RNAs," *Nat. Chem. Biol.*, 3:166-73, 2007.
Janowski et al., "Inhibiting gene expression at transcription start sites in chromosomal DNA with antigene RNAs," *Nat. Chem. Biol.*, 1:216-22, 2005.
Janowski et al., "Inhibiting transcription of chromosomal DNA with antigene peptide nucleic acids," *Nat Chem. Biol.*, 1:210-215, 2005.
Janowski et al., "Involvement of AGO1 and AGO2 in mammalian transcriptional silencing," *Nat. Struct. Mol. Biol.*, 13:787-92, 2006.
John et al., "Human MicroRNA targets," *PLoS Biol.*, 2:e363, 2004.
Kaihatsu, "Recognition of chromosomal DNA by PNAs," *Chemistry & Biology*, 11:749-758, 2004.
Kapranov et al., "Genome-wide transcription and the implications for genomic organization," *Nat. Rev. Genet.*, 8:413-23, 2007.
Kapranov et al., "New class gene-termini-associated human RNAs suggests a novel RNA copying mechanism," *Nature*, 466:642-6, 2010.
Kapranov et al., "RNA maps reveal new RNA classes and a possible function for pervasive transcription," *Science*, 316:1484-88, 2007.
Kawasaki and Taira, "Induction of DNA methylation and gene silencing by short interfering RNAs in human cells," *Nature*, 431:211-217, 2004.
Keen and Davidson, "The biology of breast cancer," *Cancer*, 97(s3):825-833, 2003.
Kim et al., "Argonaute-1 directs siRNA-mediated transcriptional gene silencing in human cells," *Nat. Struct. Mot. Biol.*, 13:793-7, 2006.
Kim et al., "MicroRNA-directed transcriptional gene silencing in mammalian cells," *PNAS*, 105:16230-16235, 2008.
Kuwabara et al., "A small modulatory dsRNA specifies the fate of adult neural stem cells," *Cell*, 116:779-793, 2004.
Lagos-Quintana et al., "Identification of novel genes coding for small expressed RNAs," *Science*, 294:853-8, 2001.
Lee et al., "The *C. elegans* heterochronic gene lin-4 encodes small RNAs with antisense complementarity to lin-14," *Cell*, 75:843-54, 1993.
Li et al., "Small dsRNAs induce transcriptional activation in human cells," *Proc. Natl. Acad. Sci. USA*, 103:17337-42, 2006.
Li et al., "Small interfering RNA directed transcriptional activation in human cells," *Proceedings of the Annual Meeting of the American Association for Cancer Research*, New York, New York, 46:1436, 2005.
Liu et al., "Argonaute2 is the catalytic engine of mammalian RNAi," *Science*, 305:1437-1441, 2004.
Meister et al., "Human Argonaute2 mediates RNA cleavage targeted by miRNAs and siRNAs," *Mol. Cell.*, 15:185-197, 2004.
Morris et al., "Small interfering RNA-induced transcriptional gene silencing in human cells," *Science*, 305:1289-1292, 2004.
Ota et al., "Complete sequencing and characterization of 21,243 full-length human cDNAs," *Nat. Genet.*, 36:40-5, 2004.
Park et al., "Double-stranded siRNA targeted to the huntingtin gene does not induce DNA methylation," *Biochem. Biophys. Res. Comm.*, 323:275-280, 2004.
Paroo and Corey, "Challenges for RNAi in vivo," *Trends Biotechnol.*, 22:390-394, 2004.
Place et al., "MicroRNA-373 induces expression of genes with complementary promoter sequences," *Proc. Natl. Acad. Sci. USA*, 105:1608-13, 2008.
Pulukuri and Rao, "Small interfering RNA directed reversal of urokinase plasminogen activator demethylation inhibits prostate tumor growth and metastasis," *Cancer Res.*, 67:6637-6646, 2007.
Riken Genome Exploration Research Group and Genome Science Group (Genome Network Project Core Group) and the FANTOM Consortium, "Antisense transcription in the mammalian transcriptome," *Science*, 309(5740):1564-1566, 2005.
Rossi et al., "Transcriptional activation by small RNA duplexes," *Nature Chemical Biology*, 3:136-137, 2007.
Schwartz el al., "Antisense transcripts are targets for activating small RNAs," *Nat. Struct. Mol. Biol.*, 15:842-8, 2008.
Stark et al., "Identification of *Drosophila* MicroRNA targets," *PLoS Biol.*, 1:397-409, 2003.
Sun et al., "Evidence for a preferential targeting of 3'-UTRs by cis-encoded natural antisense transcripts," *Nucleic Acids Res.*, 33:5533-5543, 2005.
Suzuki et al., "Prolonged transcriptional silencing and CpG methylation induced by siRNAs targeted to the HIV-1 promoter region," *J. RNAi Gene Silencing*, 1:66-78, 2005.
Takai and Jones, "Comprehensive analysis of CpG islands in human chromosomes 21 and 22," *Proc Natl Acad Sci USA*, 99:3740-3745, 2002.
Takai and Jones, "The CpG island searcher: a new WWW resource," *In Silico Biol.*, 3:235-240, 2003.
Tang, "siRNA and miRNA: an insight into RISCs," *Trends Biochem. Sci.*, 30:106-114, 2005.
The ENCODE Project Consortium, "Identification and analysis of functional elements in 1% of the human genome by the ENCODE pilot project," *Nature*, 447:799-816, 2007.
The FANTOM Consortium, "The transcriptional landscape of the mammalian genome," *Science*, 309:1559-1563, 2005.
Ting et al., "Short double-stranded RNA induces transcriptional gene silencing in human cancer cells in the absence of DNA methylation," *Nat. Genet.*, 37:906-10, 2005.
Tsuritani et al., "Distinct class of putative "non-conserved" promoters in humans: comparative studies of alternative promoters of human and mouse genes," *Genome Res.*, 17:1005-14, 2007.
Wahlestedt, "Natural antisense and noncoding RNA transcripts as potential drug targets," *Drug Discovery Today*, 11(11-12):503-508, 2006.
Wahlestedt et al., "Potent and nontoxic antisense oligonucleotides containing locked nucleic acids," *Proc. Natl. Acad. Sci. USA*, 97:5633-5638, 2000.
Wakaguri et al., "DBTSS: database of transcription start sites, progress report 2008," *Nucleic Acids Res.*, 36:D97-101, 2008.
Younger el al., "Endogenous small RNA targets gene promoter in mammalian cells," Gordon Research Conference, Salve Regina University, Newport, RI, Jun. 1-6, 2008.
Younger et al., "Predicting potential miRNA target sites within gene promoters." *Bioorg. Med. Chem. Lett.*, 19:3791-4, 2009.
Yue, "Regulation of transcriptional by small RNAs complementary to sequence downstream from the 3' termini of genes," presented at the 7th Annual Postdoctoral Research Symposium, UT Southwestern Medical Center, Feb. 5-10, 2010.
Zhang et al., "Reduction of liver Fas expression by an antisense oligonucleotide protects mice from fulminant hepatitis," *Nature Biotech.*, 18:862-867, 2000.
Zhang et al., "Regulation of endothelial nitric oxide synthase by small RNA," *Proc. Natl. Acad. Sci USA*, 102:16967-16972, 2005.
Esau et al., "miR-122 regulation of lipid metabolism revealed by in vivo antisense targeting," *Cell Metabolism*, 3:87-98, 2006.
Gleave and Monia, "Antisense therapy for cancer," *Nature Reviews: Cancer*, 5:468-479, 2005.
Matsui et al., "Activation of LDL receptor expression by small RNAs complementary to a noncoding transcript that overlaps the LDLR promoter," *Chemistry & Biology*, 17:1344-1355, 2010.
Wolfram et al., "Mechanisms and optimization of in vivo delivery of lipophilic siRNAs," *Nature Biotechnology*, 25(10):1149-1157, 2007.
Zimmermann et al., "RNAi-mediated gene silencing in non-human primates," *Nature*, 441:111-114, 2006.

\* cited by examiner

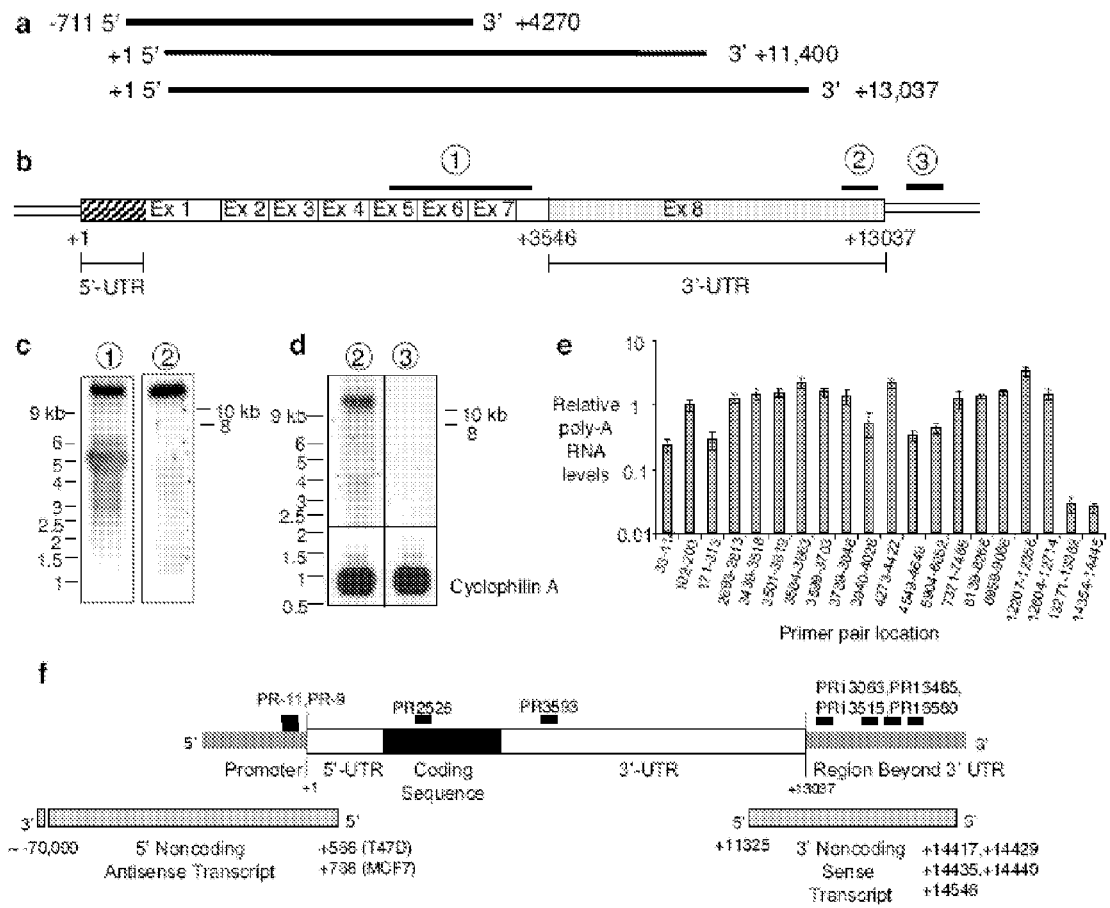
FIG. 1A-F

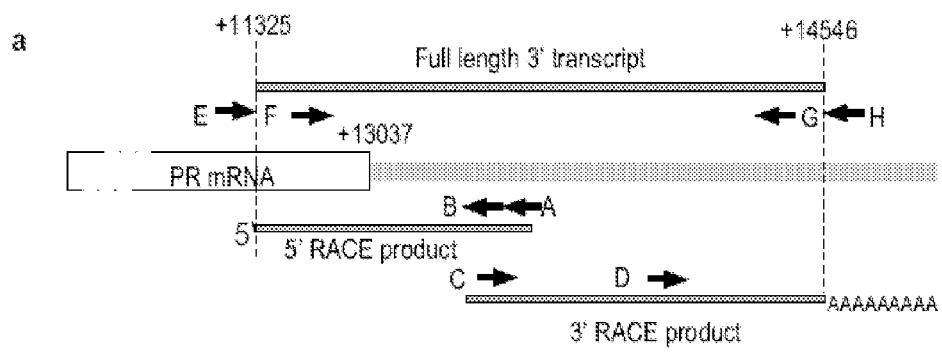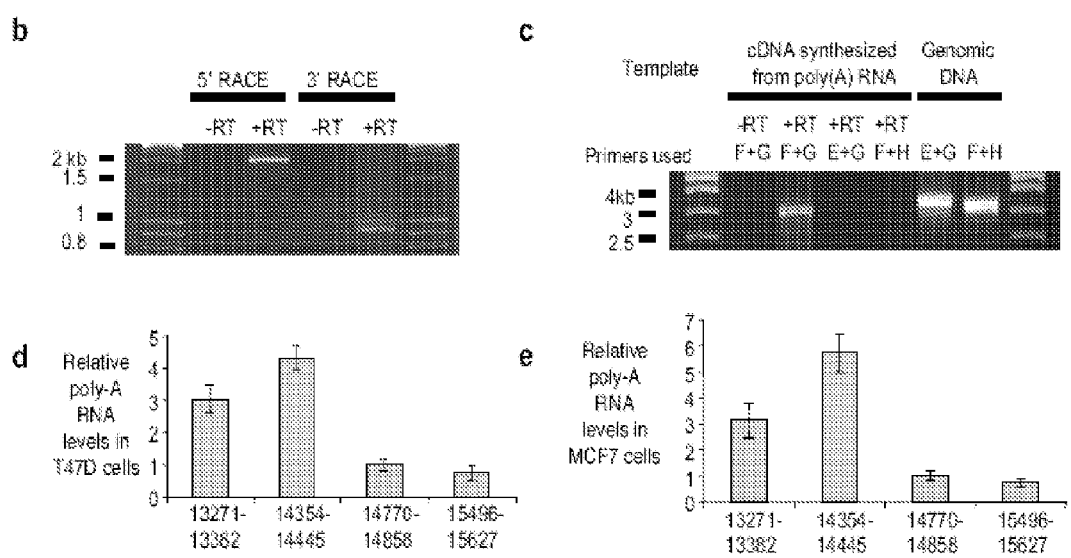
FIG. 2A-E

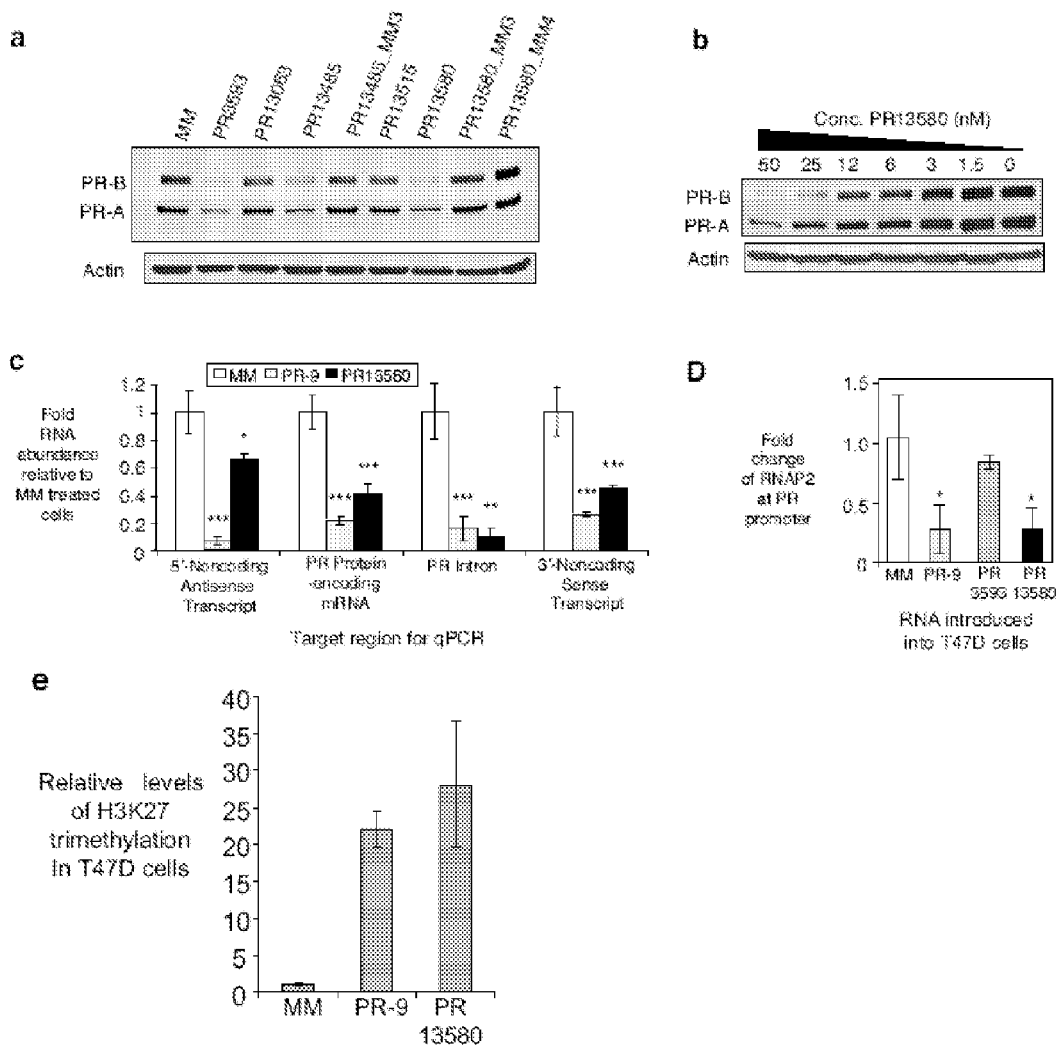
FIG. 3A-E

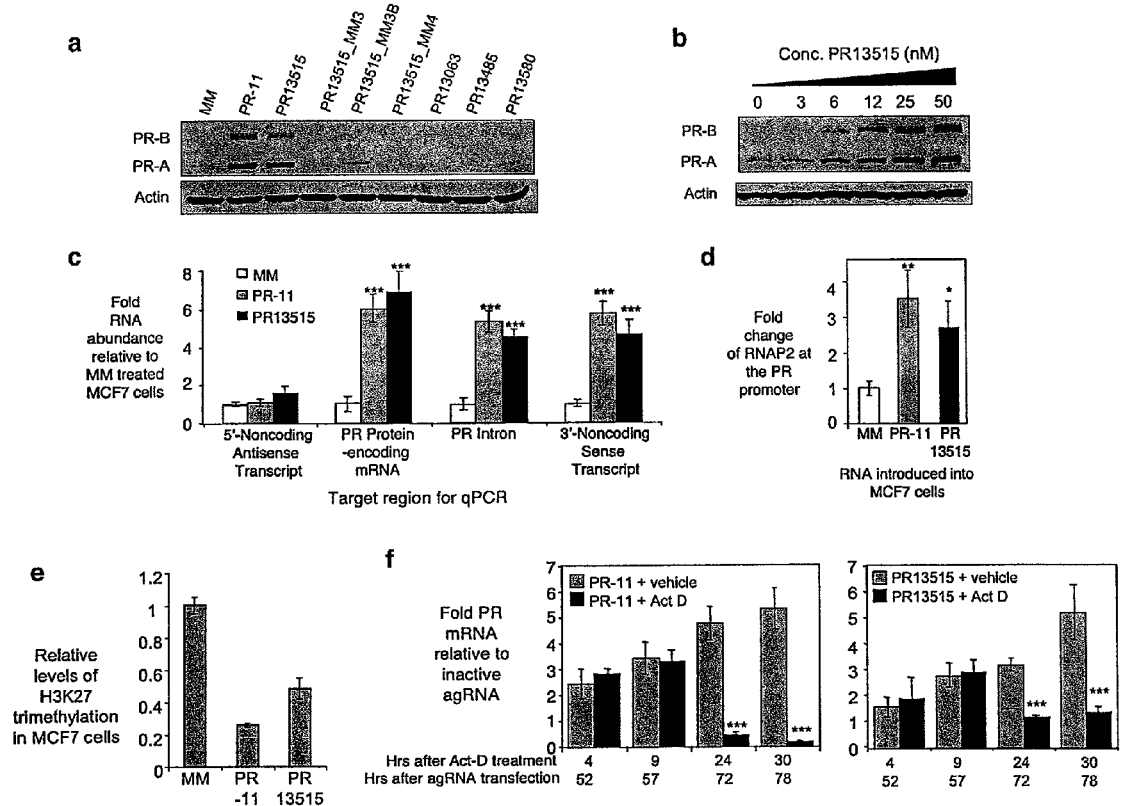
FIG. 4A-F

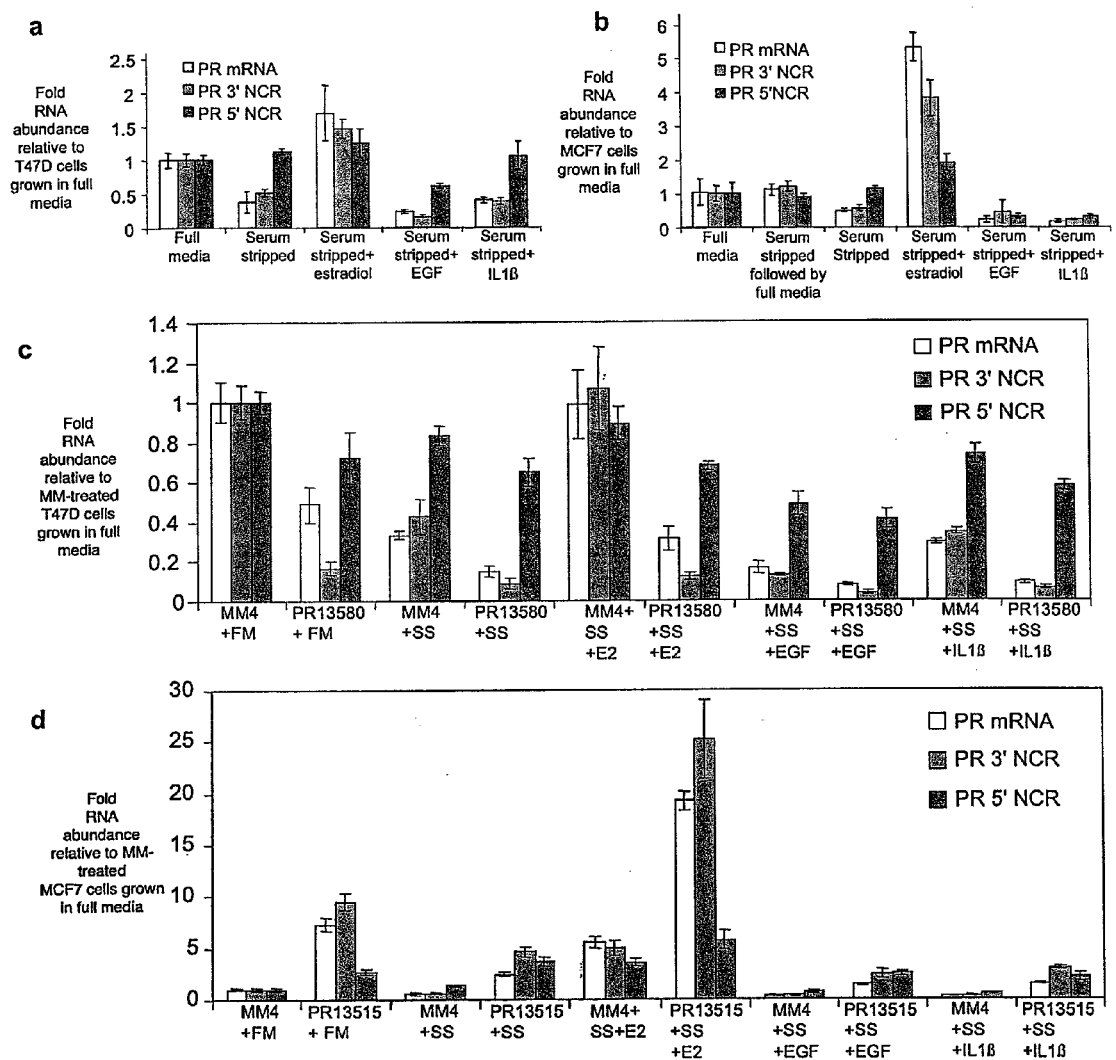
FIG. 5A-D

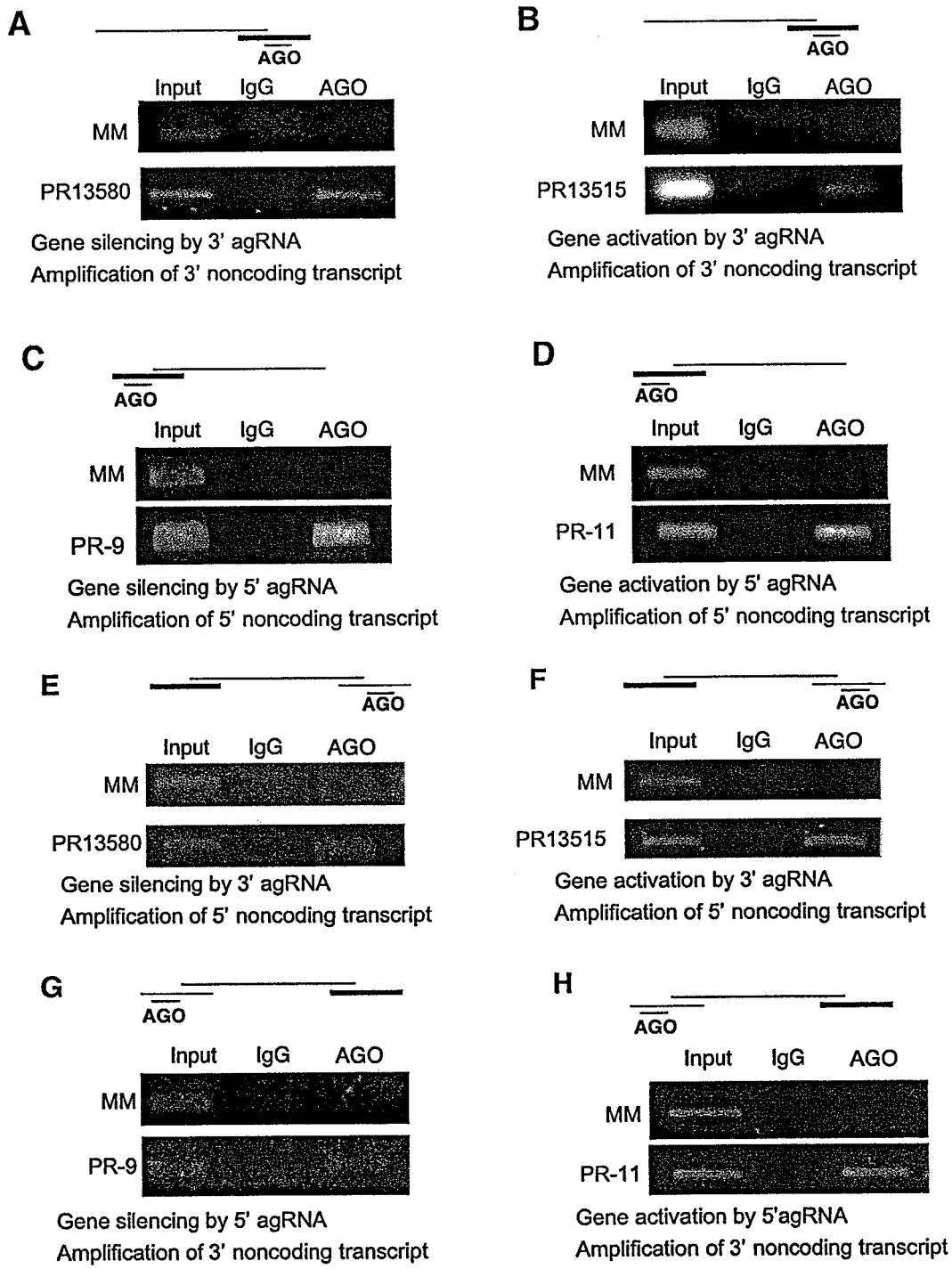
FIG. 6A-H

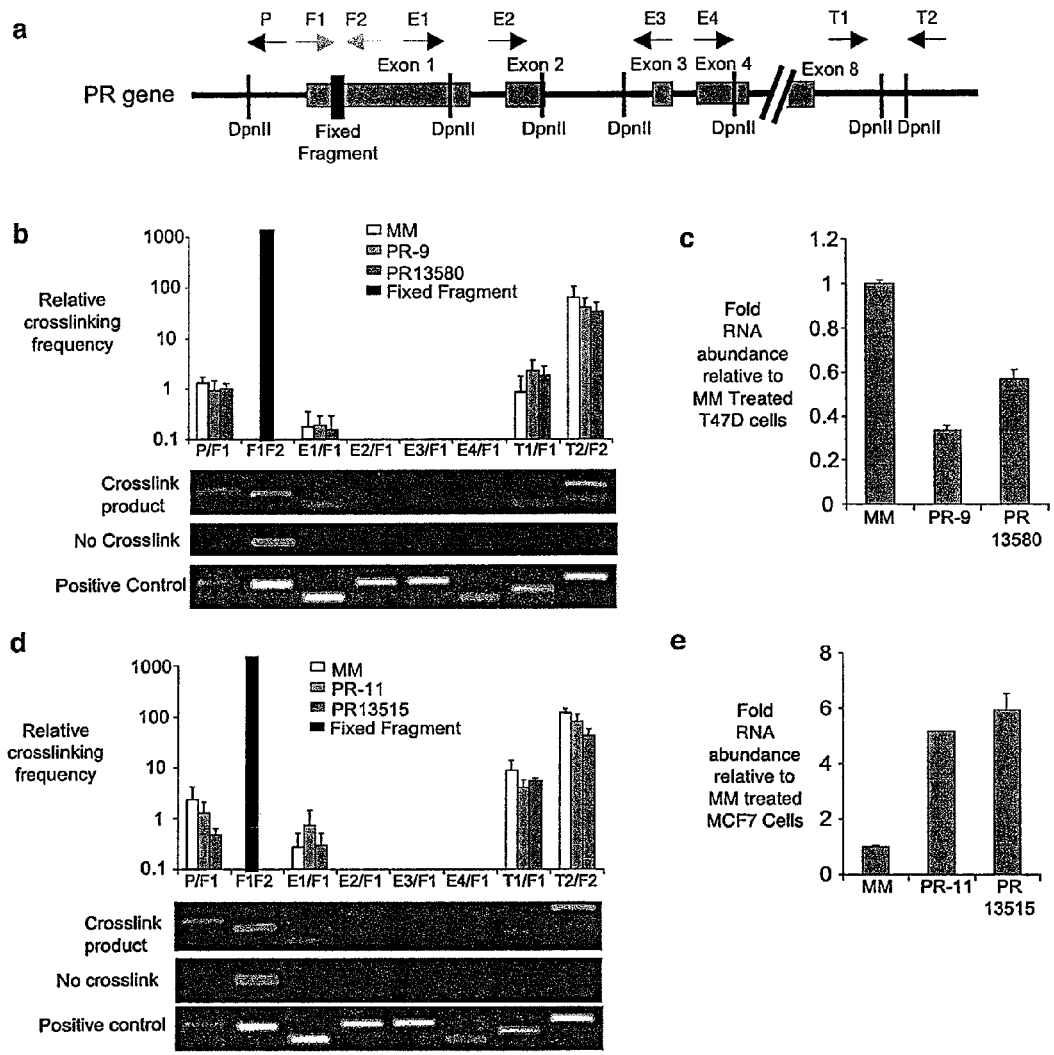
FIG. 7A-E

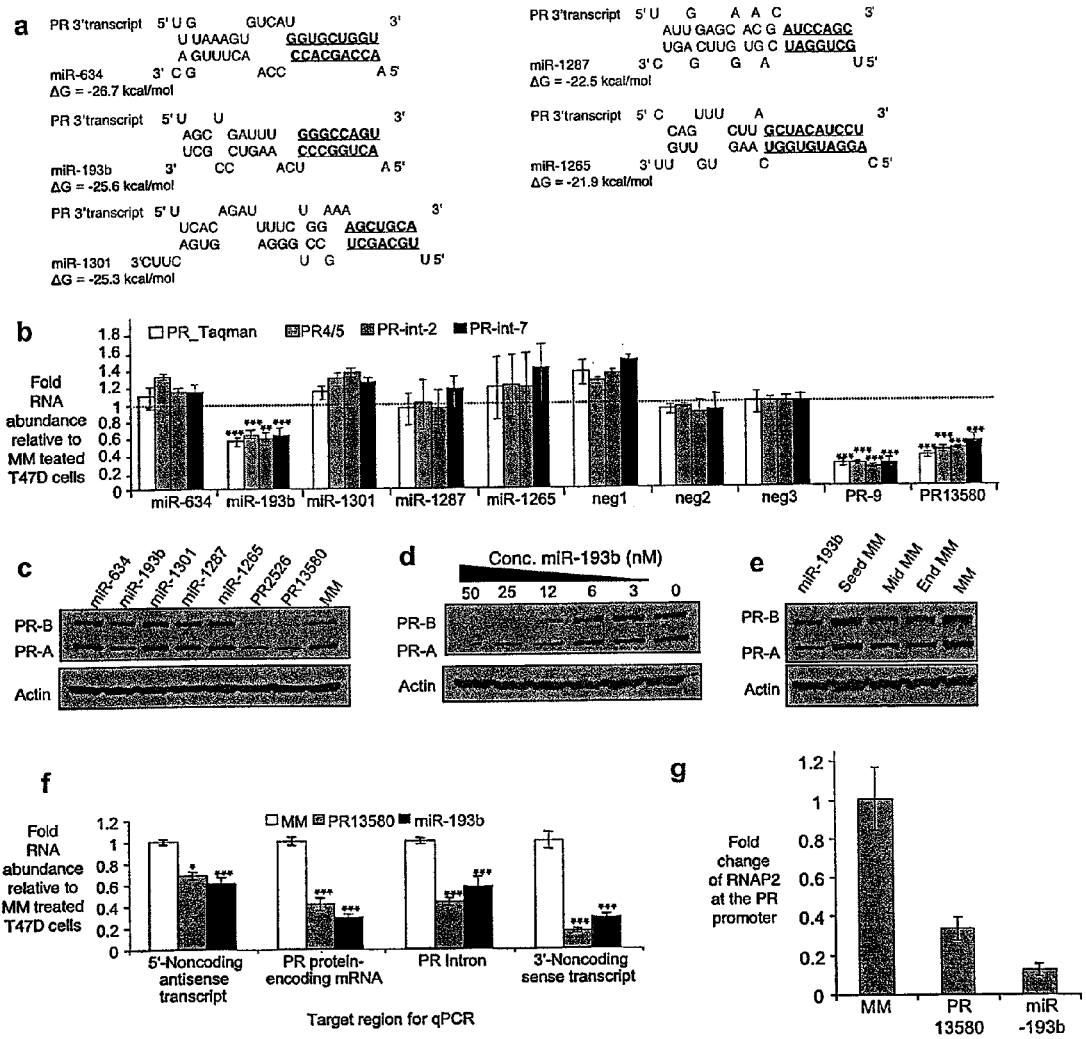
FIG. 8A-G

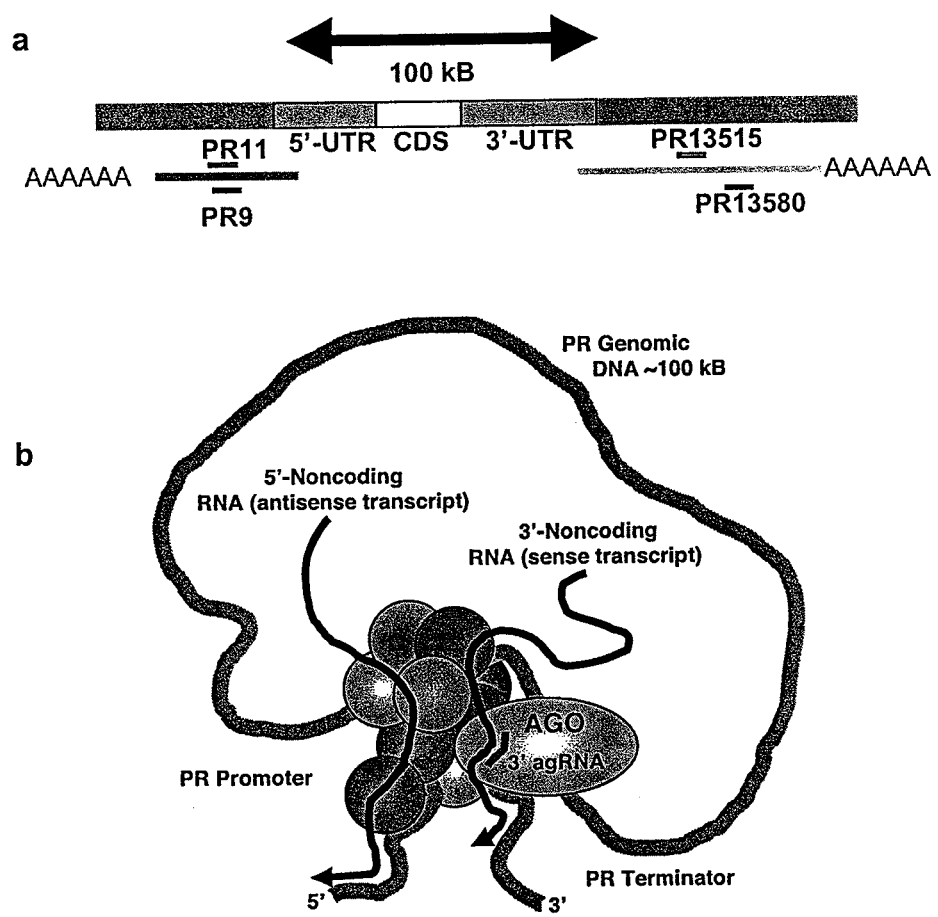
FIG. 9A-B

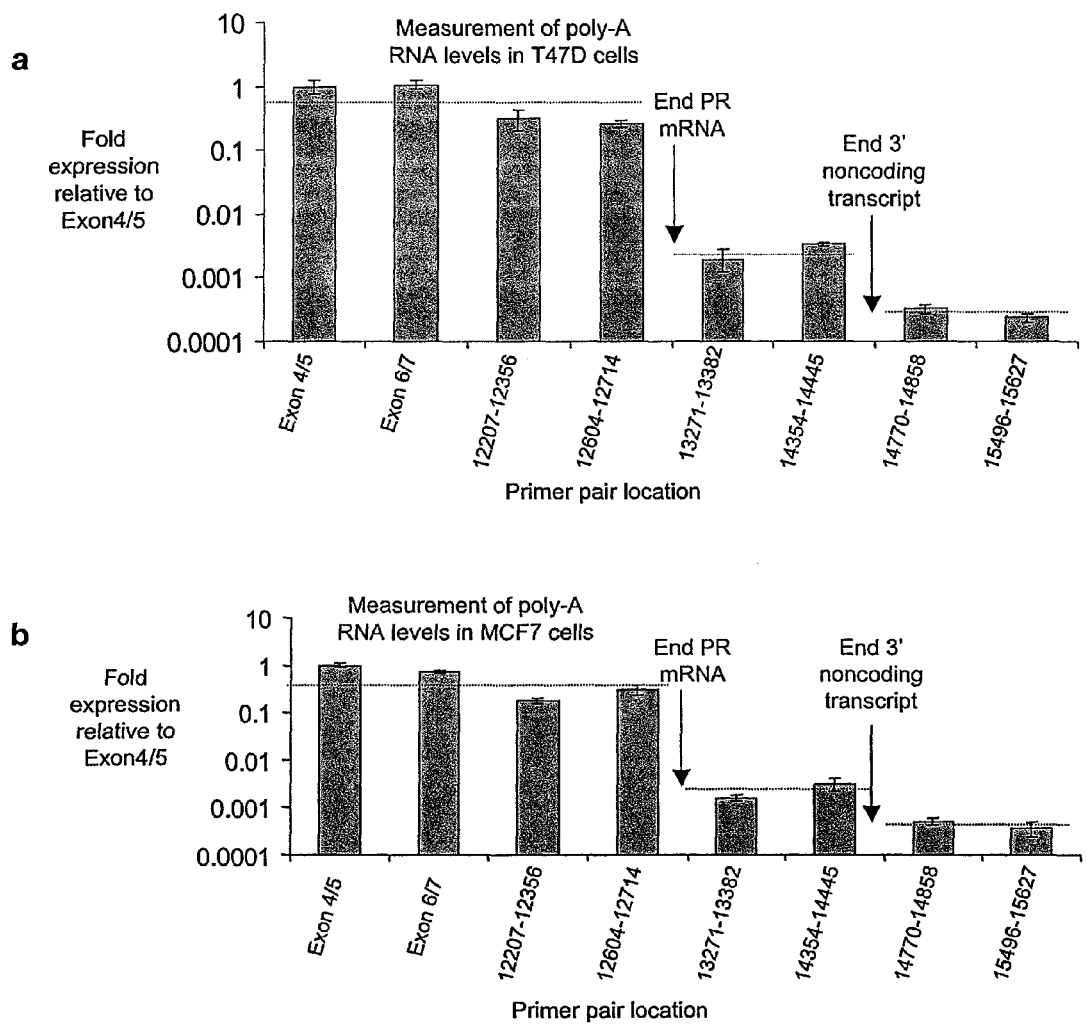
FIG. 10A-B

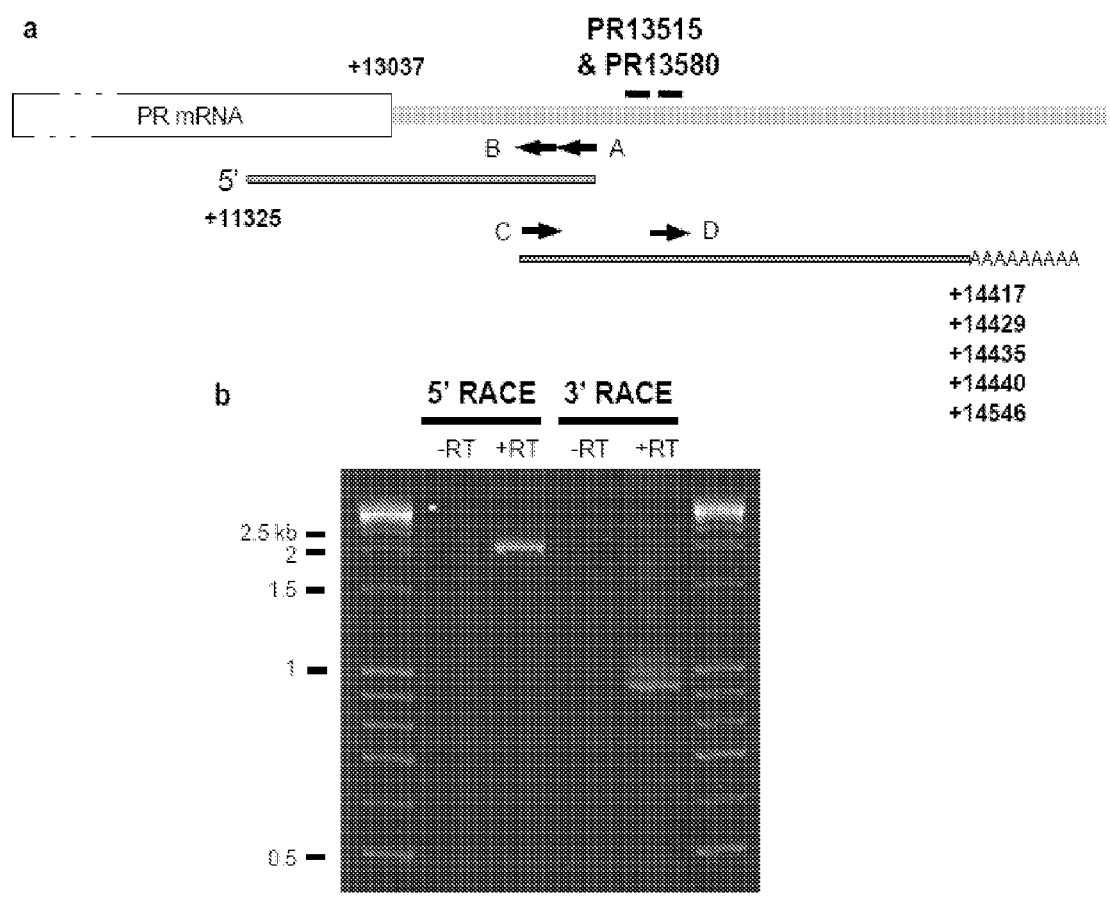
FIG. 11A-B

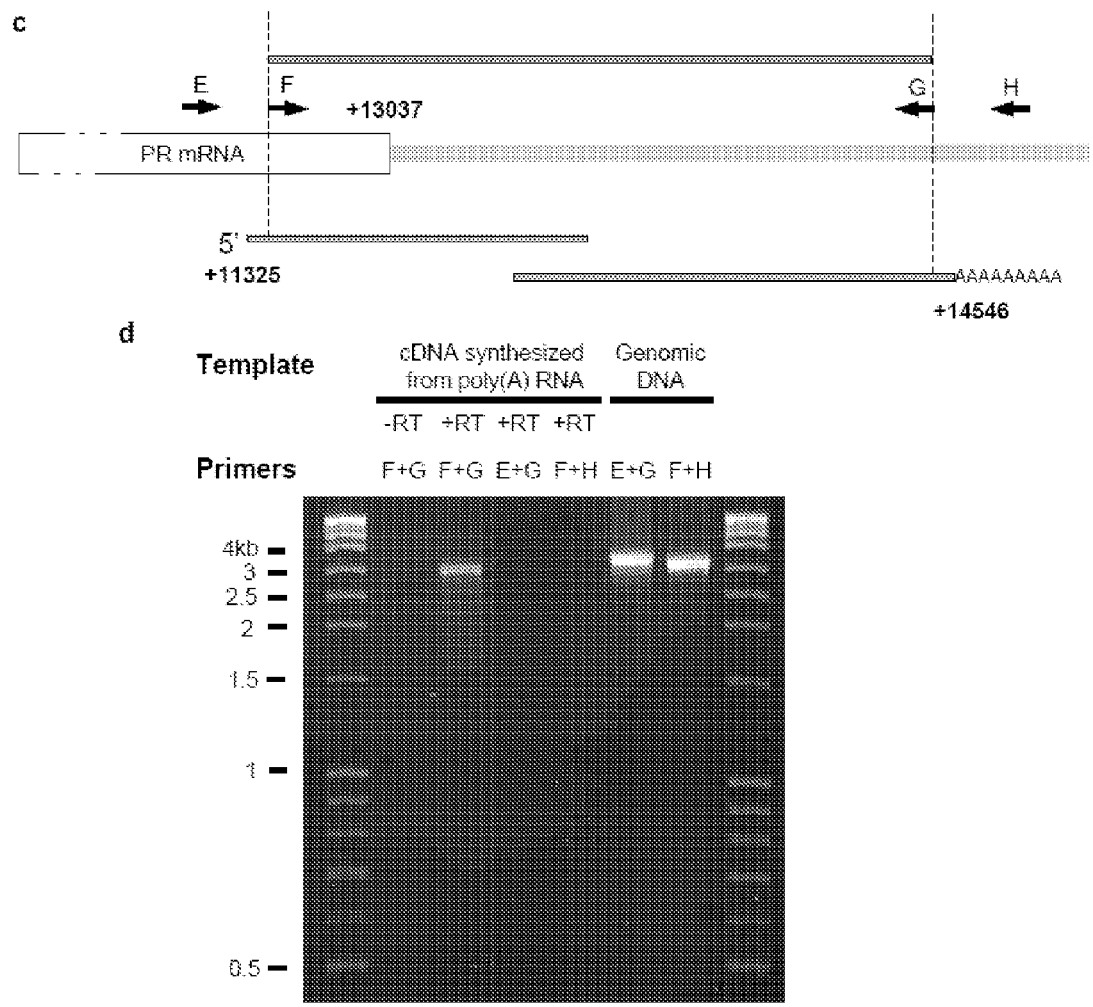
FIG. 11C-D

E  GTTTCTTTCTCCAGGTCCTCACTGGCCATACACCAGTCCCTTGTTAGTTATGCCTGGTCATAGACC
CCCGTTGCTATCATCTCATATTTAAGTCTTTGGCTTGTGAATTTATCTATTCTTTCAGCTTCAGCAC
TGCAGAGTGCTGGGACTTTGCTAACTTCCATTTCTTGCTGGCTTAGCACATTCCTCATAGGCCCAG
CTCTTTTCTCATCTGGCCCTGCTGTGGAGTCACCTTGCCCCTTCAGGAGAGCCATGGCTTACCAC
TGCCTGCTAAGCCTCCACTCAGCTGCCACCACACTAAATCCAAGCTTCTCTAAGATGTTGCAGACT
TTACAGGCAAGCATAAAAGGCTTGATCTTCCTGGACTTCCCTTTACTTGTCTGAATCTCACCTCCT
TCAACTTTCAGTCTCAGAATGTAGGCATTTGTCCTCTTTGCCCTACATCTTCCTTCTTCTGAATCAT
GAAAGCCTCTCACTTCCTCTTGCTATGTGCTGGAGGCTTCTGTCAGGTTTTAGAATGAGTTCTCAT
CTAGTCCTAGTAGCTTTTGATGCTTAAGTCCACCTTTTAAGGATACCTTTGAGATTTAGACCATGTT
TTTCGCTTGAGAAAGCCCTAATCTCCAGACTTGCCTTTCTGTGGATTTCAAAGACCAACTGAGGAA
GTCAAAAGCTGAATGTTGACTTTCTTTGAACATTTCCGCTATAACAATTCCAATTCTCCTCAGAGCA
ATATGCCTGCCTCCAACTGACCAGGAGAAAGGTCCAGTGCCAAAGAGAAAAACACAAAGATTAAT
TATTTCAGTTGAGCACATACTTTCAAAGTGGTTTGGGTATTCATATGAGGTTTTCTGTCAAGAGGG
TGAGACTCTTCATCTATCCATGTGTGCCTGACAGTTCTCCTGGCACTGGCTGGTAACAGATGCAA
AACTGTAAAAATTAAGTGATCATGTATTTTAACGATATCATCACATACTTATTTTCTATGTAATGTTT
TAAATTTCCCCTAACATACTTTGACTGTTTTGCACATGGTAGATATTCACATTTTTTTGTGTTGAAGT
TGATGCAATCTTCAAAGTTATCTACCCCGTTGCTTATTAGTAAAACTAGTGTTAATACTTGGCAAGA
GATGCAGGGAATCTTTCTCATGACTCACGCCCTATTTAGTTATTAATGCTACTACCCTATTTTGAGT
AAGTAGTAGGTCCCTAAGTACATTGTCCAGAGTTATACTTTTAAAGATATTTAGCCCCATATACTTC
TTGAATCTAAAGTCATACACCTTGCTCCTCATTTCTGAGTGGGAAAGACATTTGAGAGTATGTTGA
CAATTGTTCTGAAGGTTTTTGCCAAGAAGGTGAAACTGTCCTTTCATCTGTGTATGCCTGGGGCTG
GGTCCCTGGCAGTGATGGGGTGACAATGCAAAGCTGTAAAAACTAGGTGCTAGTGGGCACCTAA
TATCATCATCATATACTTATTTTCAAGCTAATATGCAAAATCCCATCTCTGTTTTTAAACTAAGTGTA
GATTTCAGAGAAAATATTTTGTGGTTCACATAAGAAAACAGTCTACTCAGCTTGACAAGTGTTTTAT
GTTAAATTGGCTGGTGGTTTGAAATGAATCATCTTCACATAATGTTTTCTTTAAAAATATTGTGAATT
TAACTCTAATTCTTGTTATTCTGTGTGATAATAAAGAATAAACTAATTTCTATATCTCTCTTTATTAAT
GAATTATAGCATCTAAAACCTCAATACAATTACATACAAGACACACACTAATCATCAGTAGTACATT
CTTTACCAGTCATTTAAAATTTATAACCAACATTTCAATTTGTACAATACTGTATGTGGCATAAGGT
GAGATATTTATATGGAAGATTTGGCATTATAGAGAAAATATCCTTGACTGGGTATGCATTTTAGCAA
AGCAAAGAGTGATTCTCAGGCAATCAAGTTGAAACCAACTACACAGTGTTTCAATCAGAAAGACAA
AATACAATCAACTGACATCTAGTGAGATTCAATAATATACTGTTTTGGCTATTCACATTGATTAAAAA
GTTTGGTATTATACAAGAATTTTCATATGAAATTTAATGCATTTCACATTAAGGTGAATGATATTCTA
CTTGTAATAACAAAGTATTTCAGACTACATTGGTTTCATTACTAGGAATATAATTTAGTATAGCTCTA
GAAATATACAAATATGCTCCTTTAGTAAATAAAATAAATGCCTAAATTCTATAAGGAACTGATGCAG
GCAAACCCTAAAATGGGGGCTCAGCTTGGGAGGATTTTTGGCTTAATTCAGAAAAGAATTCAAGA
GGGAACCCACAGTGAAAGAAGCCAAGTTTATTGGAGCAACAGCATCCAGCAAAATGGCTACTCCA
CAGGCAGAGTAGCCCTCGTGGGTTGCTGGCTAGCTATATGTATACCAACTCTTAATTATATGCTAA
ATATGAGGTCTGTTATTCACAGATTTCTGGAAAAGCTGCAGGGAGTTCTTGGAACTATATAACTT
AATTTCTGGGTGTTCCCATGGCATTTGTAAAGTGTCATGGTGCTGGTGCAGTGTCTCATAGCCTG
CAGATGCATTATAATTTCTAGTCCTAGCTGATTTGGGCCAGTTTCTTAGCTACATCCTGTTTTTGAT
CAGCAGGGTCATGAAAACAAGTCCTGGTGATCTTTTACCTCAGAACCATGTTAGGTCTTGGAGAC
ACAAAGATAAATGAGTGGAACAGGATTCTTGCTGTAAGTTTGAGTTGATACAATGCCACATATTATT
GTTTGAAATGTCAAAATACTTGTTTCTTATTGAATCAACTAGATTTGGAATAGACTGGAAAATCTGG
AAAGCTTTATTGGATCATTTTTCCTATCACTTAAACACTATTTTTTCCTGGTTAATACCATGTTTTCG
GTTTTTAAAACATGCCACCATATTCAGATTTACAAATGTAAATACGGTTGAGAAACTTCGTATTTAC
CTATGAAACAACATGCTGTTTTTTATAAATACTTGATTCTGATGGTTGGTGGAGTTTTTCCAATCAA
AGTTAACTAATGAATAAAGAGAAAATGTGGCAAGTGGCTGTGAATGTCAACGCACATGAGACTTTT
CCCTTGTGTCACTATATGTCACTGTATGGAGTCACTATAACAAACTAAGAGTATAGCTCTCTCTACA
CTAATCATGAATAAATACTTAATATCAAAAAAAAAAAAAAAAAAAAAAAA

FIG. 11E

A
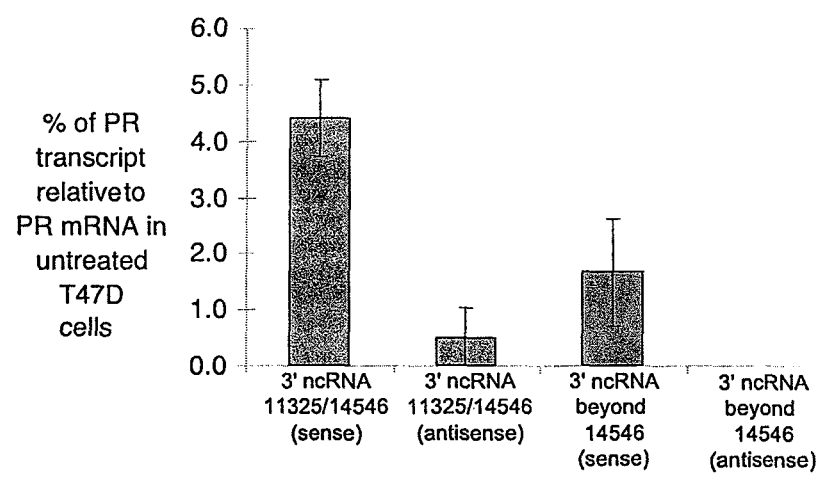
B
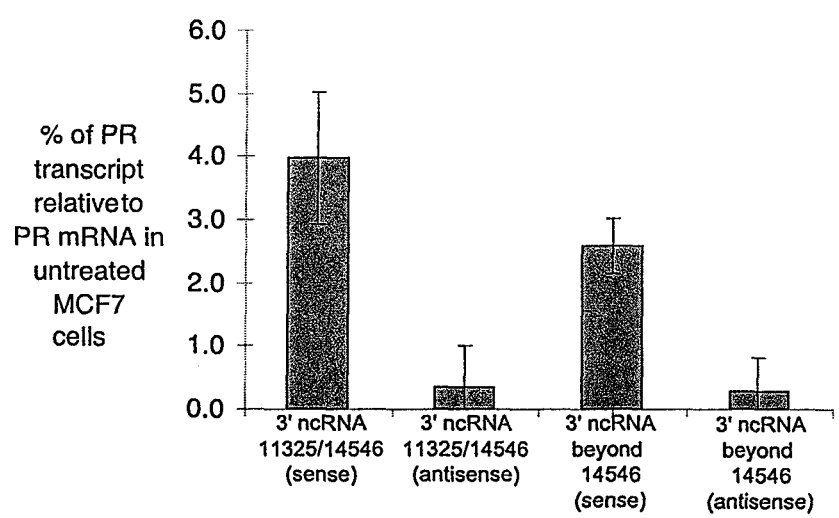
FIG 13A-B

C

PR(NM_000926) contains 8 exons and is on the minus strand of genomic DNA, spanning from Chr11:100,505,754 to Chr11:100,405,565

- Activating 3' agRNA, GTATAGCTCTAGAAATATAC, genomic DNA location: 100,405,085-100,405,065
- Inhibiting 3' agRNA, GGAACTGATGCAGGCAAAC, genomic DNA location: 100,405,025-100,405,005

Probe set 1:Complementary to the coding region of PR mRNA bDNA Probe sets 1

CE is BLUE, LE is RED and BL is green
>gi|160358783|ref|NM_000926| Homo sapiens progesterone receptor (PGR), mRNA.
[Homo sapiens] (ProbeSet1)
agtccacagctgtcactaatcggggtaagccttgttgtatttgtgcgtgtgggtggcattctcaatgagaactagcttca
cttgtcatttgagtgaaatctacaacccgaggcggctagtgctcccgcactactgggatctgagatcttcggagatgact
gtcgcccgcagtacggagccagcagaagtccgacccttcctgggaatgggctgtaccgagaggtccgactagcccaggg
ttttagtgaggggggcagtggaactcagcgagggactgagagcttcacagcatgcacgagtttgatgccagagaaaaagtc
gggagataaaggagccgcgtgtcactaaattgccgtcgcagccgcagccactcaagtgccggacttgtgagtactctgcg
tctccagtcctcggacagaagttggagaactctcttggagaactccccgagttaggagacgagatctcctaacaattact
acttttcttgcgctccccacttgccgctcgctgggacaaacgacagccacagttccctgacgacaggatggaggccaa
gggcaggagctgaccagcgccgccctcccccgcccccgacccaggaggtggagatccctccggtccagccacattcaaca
cccactttctcctccctctgccct

FIG. 13D

Probe 2 (sense): targeting the region complementary to 3' agRNAs bDNA Probe sets 2.2

CE is BLUE, LE is RED and BL is green
>gi|83641890|ref|GS00342|(ProbeSet2.2),
tattctgtgtgataataaagaataaactaatttctatatctctctttattaatgaattatagcatctaaaacctcaatac
aattacatacaagacacacactaatcatcagtagtacattctttaccagtcatttaaaatttataaccaacatttcaatt
tgtacaatactgtatgtggcataaggtgagatatttatatggaagatttggcattatagagaaaatatccttgactgggt
atgcattttagcaaagcaaagagtgattctcaggcaatcaagttgaaaccaactacacagtgtttcaatcagaaagacaa
aatacaatcaactgacatctagtgagattcaataatatactgttttggctattcacattgattaaaaagtttggtattat
acaagaatttctatatgaaatttaatgcatttcacattaaggtgaatgatattctacttgtaataacaaagtatttcaga
ctacattggtttcattactaggaatataatttagtatagctctagaaatatacaaatatgctccttagtaaataaaata
aatgcctaaattctataaggaactgatgcaggcaaaccctaaaatgggggctcagcttgggaggattttttggcttaattc
agaaaagaattcaagagggaacccacagtgaaagaagccaagtttattggagcaacagcat

FIG. 13E

Probe 3 (antisense): targeting the region complementary to 3' agRNAs.

bDNA Probe sets 3.2

CE is BLUE, LE is RED and BL is green
>gi|83641890|ref|GS00343| (ProbeSet3.2),
atgctgttgctccaataaacttggcttctttcactgtgggttccctcttgaattcttttctgaattaagccaaaaatcct
cccaagctgagccccccatttaggtttgcctgcatcagttccttatagaatttaggcatttatttatttactaaagga
gcatatttgtatatttctagagctatactaaattatattcctagtaatgaaaccaatgtagtctgaaatactttgttatt
acaagtagaatatcattcacctaatgtgaaatgcattaaatttcatatgaaaattcttgtataataccaaactttttaa
tcaatgtgaatagccaaaacagtatattattgaatctcactagatgtcagttgattgtattttgtctttctgattgaaac
actgtgtagttggtttcaacttgattgcctgagaatcactctttgctttgctaaaatgcatacccagtcaaggatatttt
ctctataatgccaaatcttccatataaatatctcaccttatgccacatacagtattgtacaaattgaaatgttggttata
aattttaaatgactggtaaagaatgtactactgatgattagtgtgtgtcttgtatgtaattgtattgaggttttagatgc
tataattcattaataaagagagatatagaaattagtttattctttattatcacacagaata

FIG. 13F

Probe 4 (sense): targeting the region downstream from the 3' end of noncoding transcript bDNA Probe sets 4.2

```
CE is BLUE,LE is RED and BL is green
>gi|83641890|ref|GS00344|(Probeset4.2),
tatagctctctctacactaatcatgaataaatacttaatatcaaagatcaagttttttaaagctatattttaatggcagg
aggttgtatttacctaatcagatgaagtttaatcccatcttataaatgattgaatccaaacaagtagaataactataata
tgcagagatccatgaccagttatttgtgagcaatttggaattcataaagcttaaacaacttaggtactctatgaaaaagc
aaagtattttatgtctgaattatgtcagctacccgtaattatgctgtgatataagaaagcagtatagtaagaatatatg
ctctggagctacaccttctcaatctcatttcaggctgtaccacttgctaactatgtgaccttgcaacatactttcactct
ctgccttagttttcttatctgtaaaatggatataacaatagtacttgtttcataggggttgttataaggatgaaatcagta
taagaaaaataaacttagagcagtgtgtgacatagcaagcactattttggtgtttcatccaaattaagtggcttttttcct
taatacataaatgattaaaggtacaaaagatattaaactttttttttttttttttgagatggagtcttgctctgtcaccc
aggctggagtgcagtggcacgatttcggctcactgcaacctccacttcccgggctcaagcgattctcttgcctcagcctc
ccaagtagctgggactacaggtgtacaccaccaggcccagctaattttttgtattttagtagagacagggtttcaccatg
ttggccaggatggtctcaatctcctgaccttgtgatctgcctgccttggcctcccaaagttctgggattacaggtgtgaa
ccactgcacctggcctaaaacttttatattatataaactagtaaaaataattttaatattttaggtcatgggaaattcag
cagcatagtaattatcaaagtagtaaatttttcagcaaaggaggtcaaggatagactgttacaagtgaaaaaaatagga
tattaatcaacaaaattctcaatctgaatagccacaattttcagtttctgtacctgaaatagtttctgcatgggacaga
ttggactaaccaaatttatctcattttatgactctagcctaactaccctccccattaaataatgttttaagtatatac
aaagggaaaaaaacaactttttgaattatgagatatactgaataaaacaataatgaaaaagctatttataaaatagttaa
gattagattataaatctaaagttg
```

FIG. 13G

Probe 5 (antisense): targeting the region downstream from the 3' end of noncoding transcript bDNA Probe sets 5.2

```
CE is BLUE,LE is RED and BL is green
>gi|83641890|ref|GS00345|(Probeset5.2),
caactttagatttataatctaatcttaactatttataaatagcttttcattattgttttattcagtatatctcataat
tcaaaaagttgttttttttcccctttgtatatacttaaaaacattatttaatggggagggtagttaggctagagtcataaaa
atgagataaatttggttagtccaatctgtcccatgcagaaactatttcaggtacagaaactgaaaaattgtggctattca
gattgagaattttgttgattaatatcctattttttcacttgtaacagtctatccttgacctcctttgctgaaaaaattt
actactttgataattactatgctgctgaatttcccatgacctaaaatattaaaaattattttttactagtttatataatat
aaaagtttaggccaggtgcagtggttcacacctgtaatcccagaactttgggaggccaaggcaggcagatcacaaggtca
ggagattgagaccatcctggccaacatggtgaaaccctgtctctactaaaaatacaaaaattagctgggcctggtggtgt
acacctgtagtcccagctacttgggaggctgaggcaagagaatcgcttgagcccgggaagtggaggttgcagtgagccga
aatcgtgccactgcactccagcctgggtgacagagcaagactccatctcaaaaaaaaaaaaaaaagtttaatatcttt
gtacctttaatcatttatgtattaaggaaaaagccacttaatttggatgaaacaccaaaatagtgcttgctatgtcacac
actgctctaagtttatttttcttatactgatttcatccttataacaaccctatgaaacaagtactattgttatatccatt
ttacagataagaaaactaaggcagagagtgaaagtatgttgcaaggtcacatagttagcaagtggtacagcctgaaatga
gattgagaaggtgtagctccagagcatatattcttactatactgctttcttatatcacagcataattacgggtagctgac
ataattcagacataaaaatacttgctttttcatagagtacctaagttgtttaagctttatgaattccaaattgctcaca
aataactggtcatggatctctgcatattatagttattctacttgtttggattcaatcatttataagatgggattaaactt
catctgattaggtaaatacaacctcctgccattaaaatatagctttaaaaaacttgatctttgatattaagtatttattc
atgattagtgtagagagagctata
```

FIG. 13H

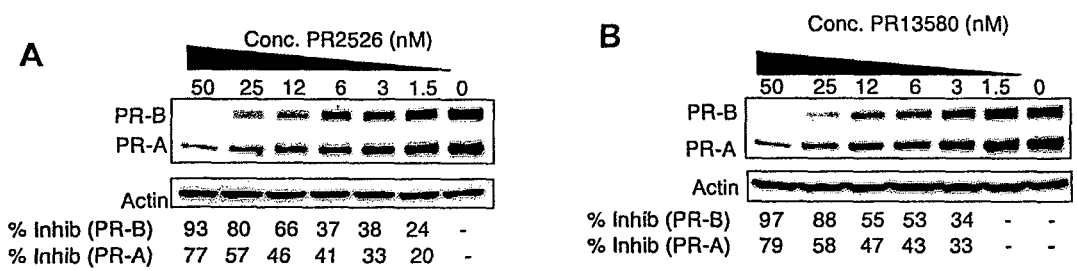
FIG. 14A-B

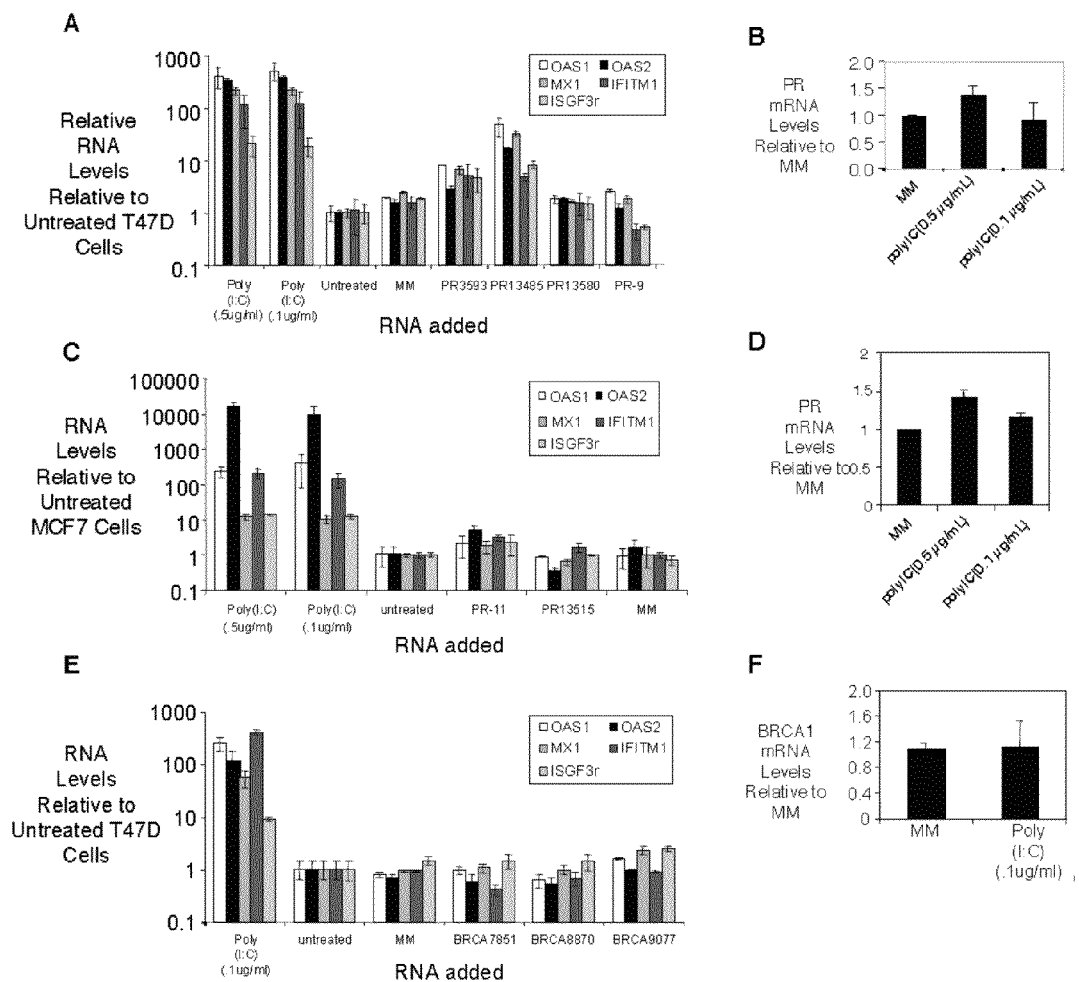
FIG. 15A-F

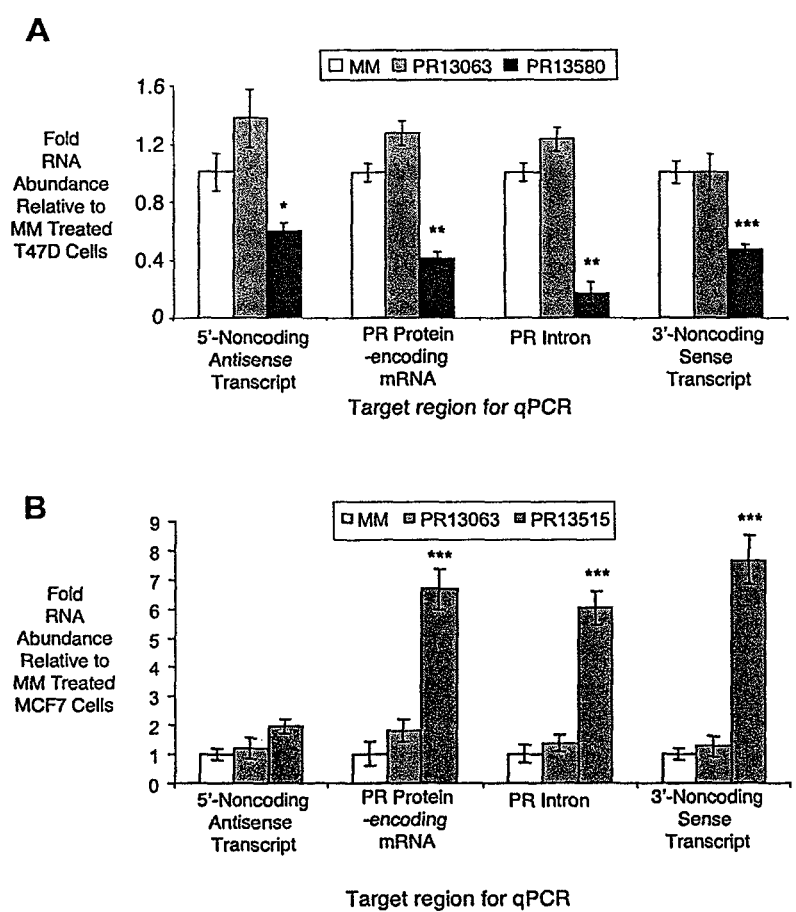
FIG. 16A-B

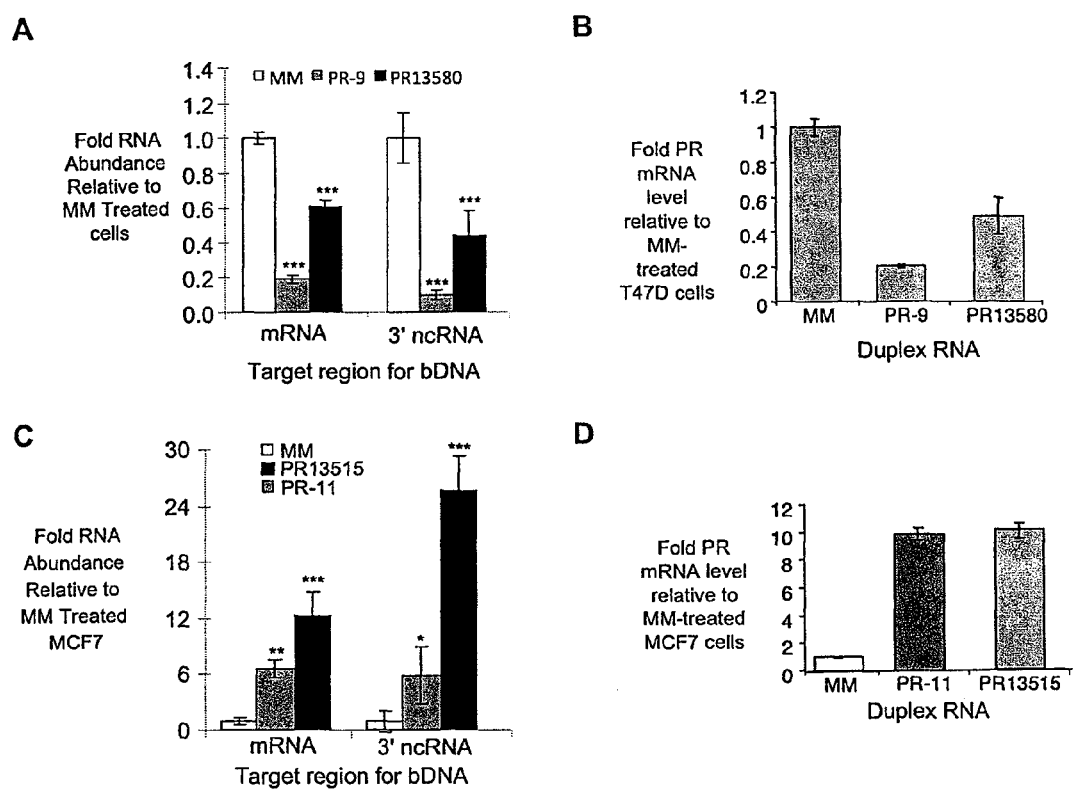
FIG. 17A-D

A  RIP product sequence  taaggaactgatgcaggcaaacnctaaaatgggggctcagnntgggagga
                         |||||||||||||||||||||||| ||||||||||||||||| |||||||
   Chr11:100405025       taaggaactgatgcaggcaaaccctaaaatgggggctcagcttgggagga RIP product sequence  tttttggc
                         ||||||||
   Chr11:100404975       tttttggc B  RIP product sequence  gactacnttggtttcnttactaggaatataatttagtatagctctagaaa
                         |||||| |||||||| ||||||||||||||||||||||||||||||||||
   Chr11:100405122       gactacattggtttcattactaggaatataatttagtatagctctagaaa RIP product sequence  tatacaaatatgctcctttagtaaataaaataaatgc
                         |||||||||||||||||||||||||||||||||||||
   Chr11:100405072       tatacaaatatgctcctttagtaaataaaataaatgc C  RIP product sequence  cctagaggaggaggcgttgttagaangctgtctggccagtccacagctgt
                         |||||||||||||||||||||||| |||||||||||||||||||||||||
   Chr11:100505791       cctagaggaggaggcgttgttagaaagctgtctggccagtccacagctgt RIP product sequence  cactaatcgggnnaagccttgttgtatttgtgngtgtgggtggcattctc
                         |||||||||||  |||||||||||||||||||| ||||||||||||||||
   Chr11:100505741       cactaatcggggtaagccttgttgtatttgtgcgtgtgggtggcattctc RIP product sequence  aat
                         |||
   Chr11:100505691       aat D  RIP product sequence  tagaggaggaggcgttgttannaagctgtctggccagtccacagctgtca
                         |||||||||||||||||||  |||||||||||||||||||||||||||||
   Chr11:100505789       tagaggaggaggcgttgttagaaagctgtctggccagtccacagctgtca RIP product sequence  ctnntcggggtaagccttgttgtatttgtgcgtgtgngtggcattctcaa
                         || |||||||||||||||||||||||||||||||||| ||||||||||||
   Chr11:100505739       ctaatcggggtaagccttgttgtatttgtgcgtgtgggtggcattctcaa RIP product sequence  t
                         |
   Chr11:100505689       t

FIG. 19A–D

```
RIP product sequence  attgagaatgccanncacacgcacaaatacaacaaggcttaccccgatta
                      ||||||||||||    ||||||||||||||||||||||||||||||||||
       Chr11:100505689 attgagaatgccacccacacgcacaaatacaacaaggcttaccccgatta RIP product sequence  gtgacagctgtggactggccagacagnnnnctaacaacgcctcctcctct
                      |||||||||||||||||||||||||||    |||||||||||||||||||
       Chr11:100505739 gtgacagctgtggactggccagacagctttctaacaacgcctcctcctct RIP product sequence  agg
                      |||
       Chr11:100505789 agg
```

*FIG. 19E*

```
RIP product sequence  cctagaggaggaggcnttgttagaaagctgtctggccagnccacagctgt
                      ||||||||||||||| ||||||||||||||||||||||||| ||||||||
       Chr11:100505791 cctagaggaggaggcgttgttagaaagctgtctggccagtccacagctgt RIP product sequence  cactaatcggngtaagccttgttgtanttgtgcgtgtgggtggcattctc
                      |||||||||| ||||||||||||||| |||||||||||||||||||||||
       Chr11:100505741 cactaatcggggtaagccttgttgtatttgtgcgtgtgggtggcattctc
```

*FIG. 19F*

```
RIP product sequence  agcnnaaaatcctcccaagctgagcccccattttagggnttgcctgcatc
                      |||   ||||||||||||||||||||||||||||||||| ||||||||||
       Chr11:100404967 agccaaaaatcctcccaagctgagcccccattttagggtttgcctgcatc RIP product sequence  agttcctta
                      |||||||||
       Chr11:100405017 agttcctta
```

*FIG. 19G*

```
RIP product sequence  ggaactgatgcaggcaaaccctaaaatgggcgctcagcttgnnaggattn
                      |||||||||||||||||||||||||||||||| ||||||||| |||||
       Chr11:100405022 ggaactgatgcaggcaaaccctaaaatggggctcagcttgggaggattt RIP product sequence  ttggct
                      ||||||
       Chr11:100404972 ttggct
```

*FIG. 19H*

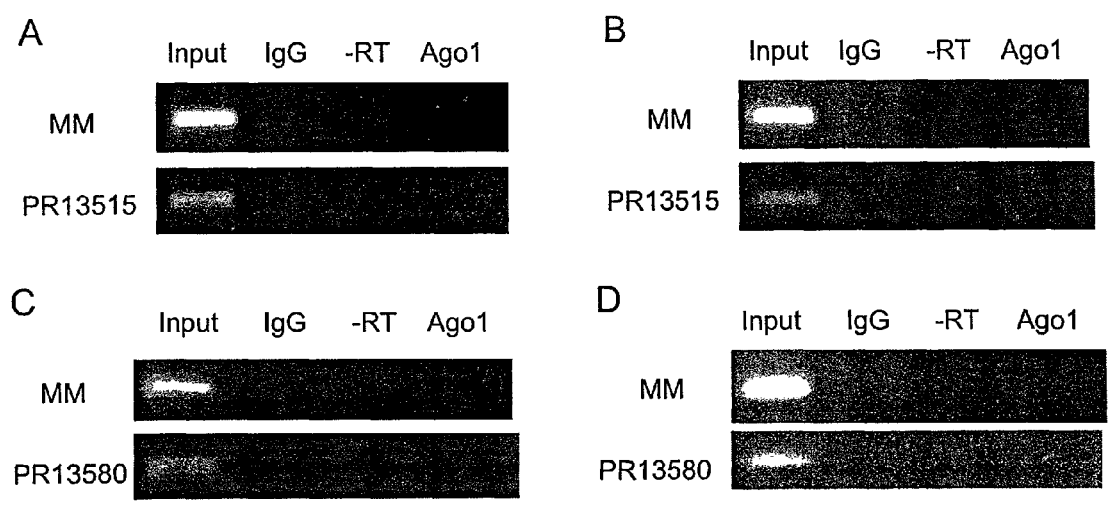
FIG. 20A-D

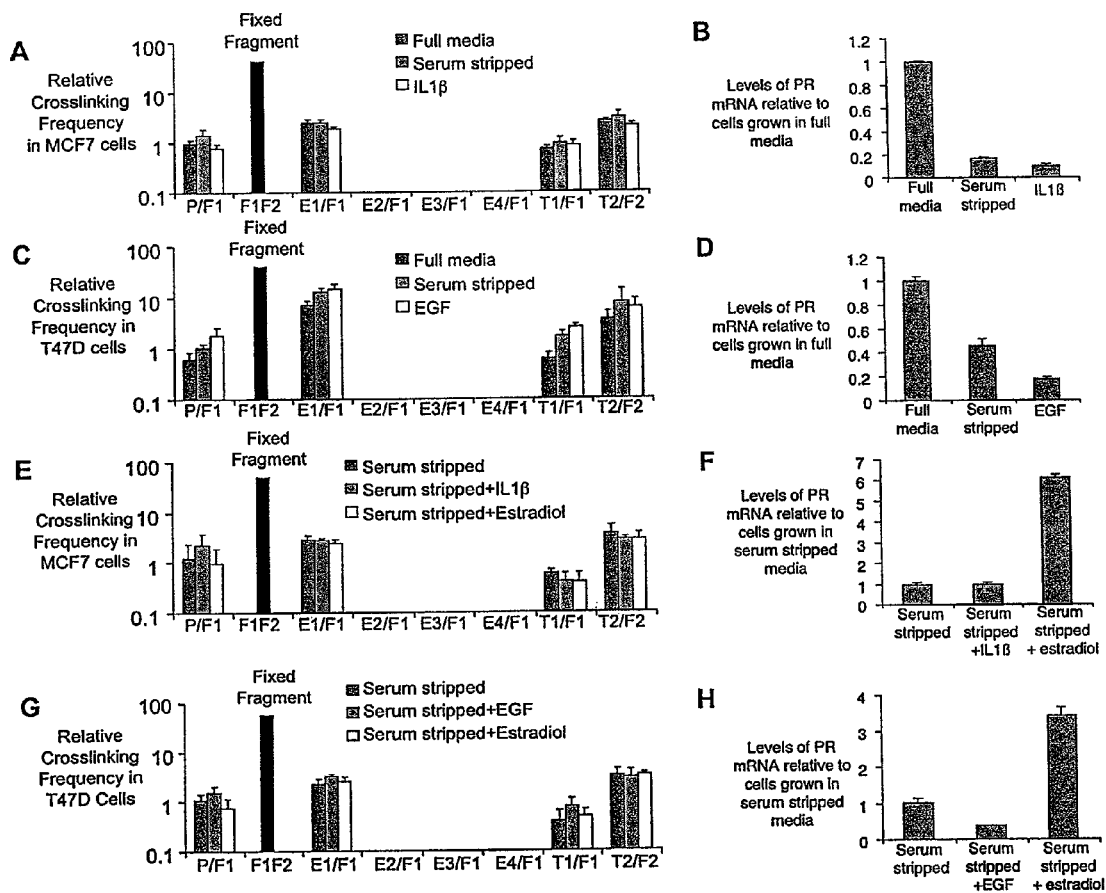
FIG. 27A-H

A

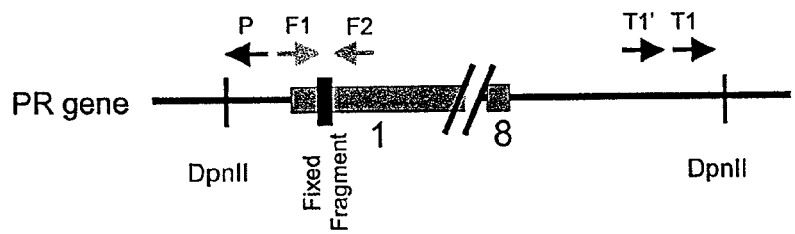

B

T47D - cells

P / T1'
```
TCCNNAAGAA CCTGCTATTG AGAGTAGCAT TCAGAATAAC GGGTGGAAAT  50
GCCAACTCCA GAGTTTCAGA TCAAAAACAG GATGTAGCTA AGAAACTGGC  100
CCAAATCAGC TAGGACTAGA AATTATAATG CATCTGCAGG CTATGAGACA  150
CTGCACCAGC AC
```

F2 / T1
```
           GG NNCGGANTTC TGCTGGCTCC GTACTGCGGG CGACAGTCAT  50
CTCCGAAGAT CAAAAACAGG ATGTAGCTAg GACTGGCCCA AATCAGCTA
```

C

MCF7 - cells

P / T1'
```
TGTGNTGGTG NAGTGTCTCA TAGCCTGCAG ATGCATTATA ATTTCTAGTC  50
CTAGCTGATT TGGGCCAGTT TCTTAGCTAC ATCCTGTTTT TGATCTGAAA  100
CTCTGGAGTT GGCATTTCCA CCCGTTATTC TGAATGCTAC TCTCAATAGC  150
AGGTTCTTTG GGATGGAA
```

F2 / T1'
```
TTGAGGNNCG GANTTCTGCT GGCTCCGTAC TGCGGGCGAC AGTCATCTCC  50
GAAGATCTCA GATCAAAAAC AGGATGTAGC TAAGAAACTG GCCCAAATCA  100
GCTAGGACTA GAAATTATAA TGCATCTGCA GGCTATGAGA CACTGCACCA  150
GCAC
```

F2 / T1
```
CGGANTTCTG CTGGCTCCGT ACTGCGGGCG ACAGTCATCT CCGAAGATCA  50
CCAGGACTTG TTTTCATGAC CCTGCTGATC AAAAACAGGA TGTAGCTAAG  100
AAACTGGCCC AAATCAGCTA
```

F1 / T1
```
TTTACACCCG AGGCGGCTAG TNNTCCCGCA CTACTGGGAT CAAAAACAGG  50
ATGTAGCTAA GAAACTGGCC CAAATCAGCT A
```

FIG. 28A-C

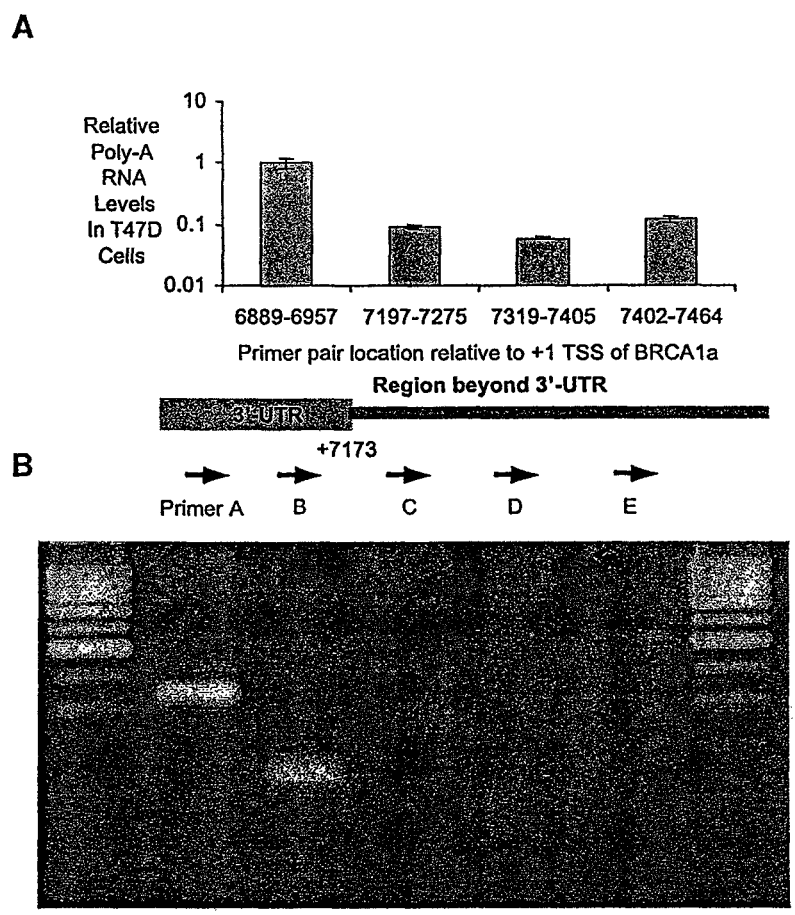
FIG. 29A-B

A
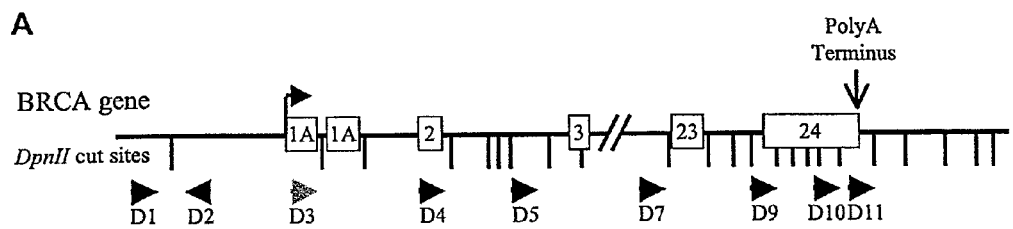
B
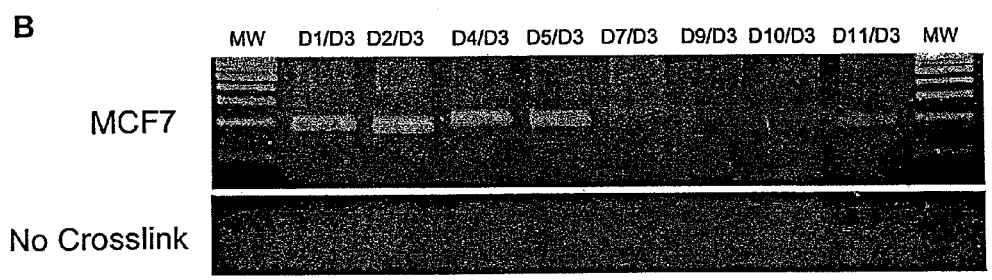
C
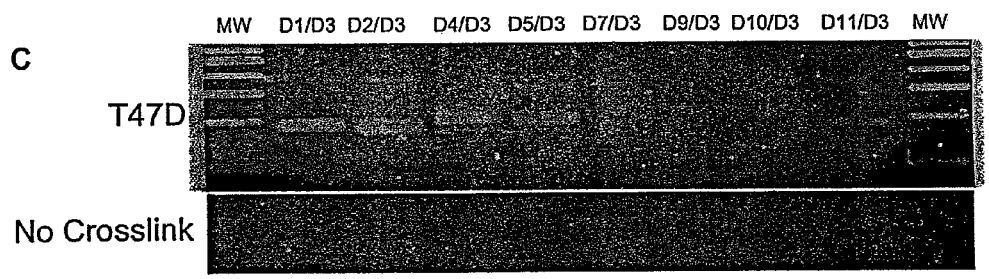
D
```
         tctttgacgggggnagggggcggaacctgagaggcgtaaggcgttgtgaa  50
D3 / D11 ccctggggagggggggcagtttgtaggtcgcgagggaagcgctgaggatct  100
         tagtcctagaactgcaaggacccagagcctctagaagggaacacgccctg  150
         cgaacacctttatttttggcctcatgaa
```
FIG. 30A-D

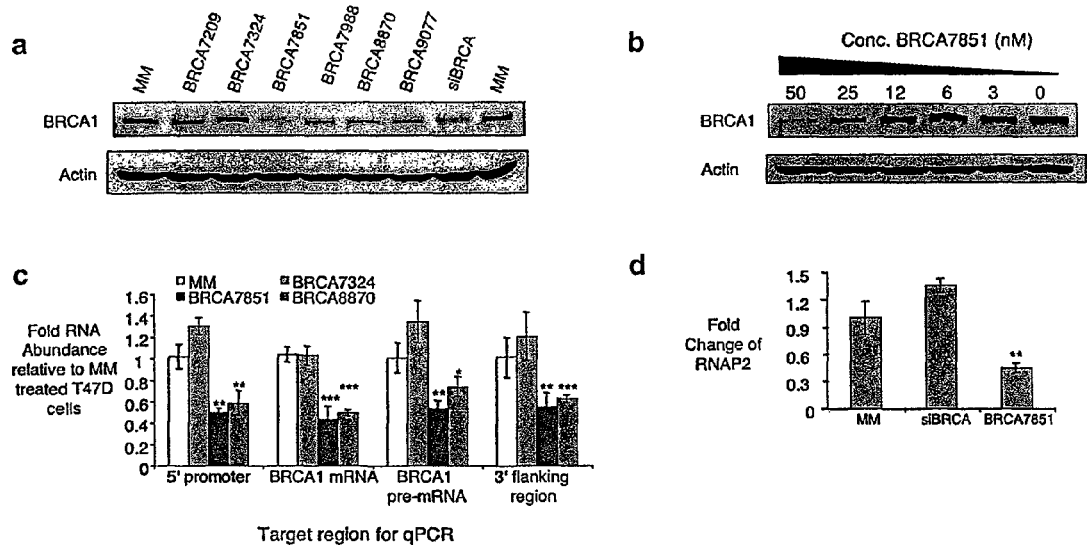
FIG. 31A-D

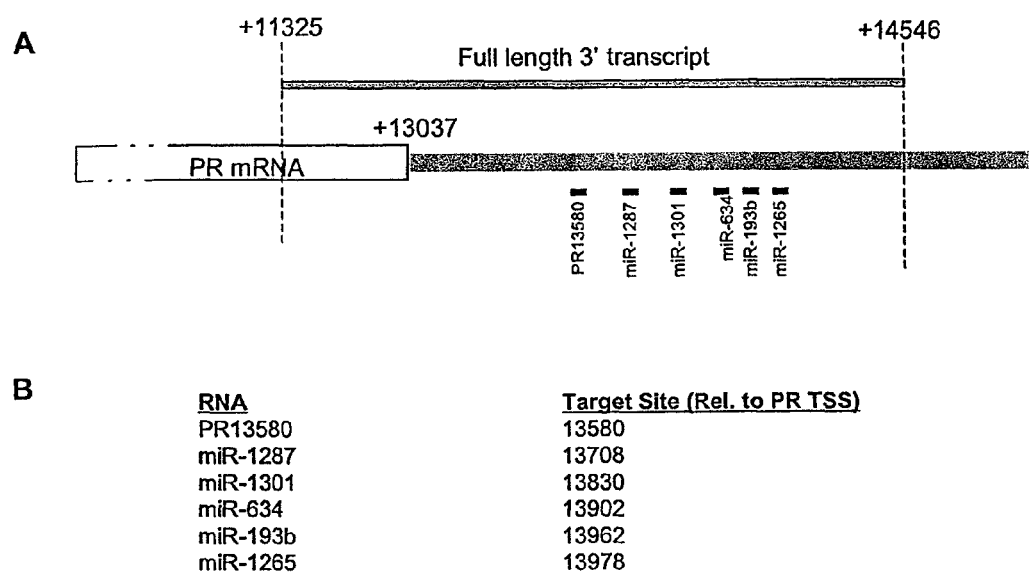
FIG. 32A-B

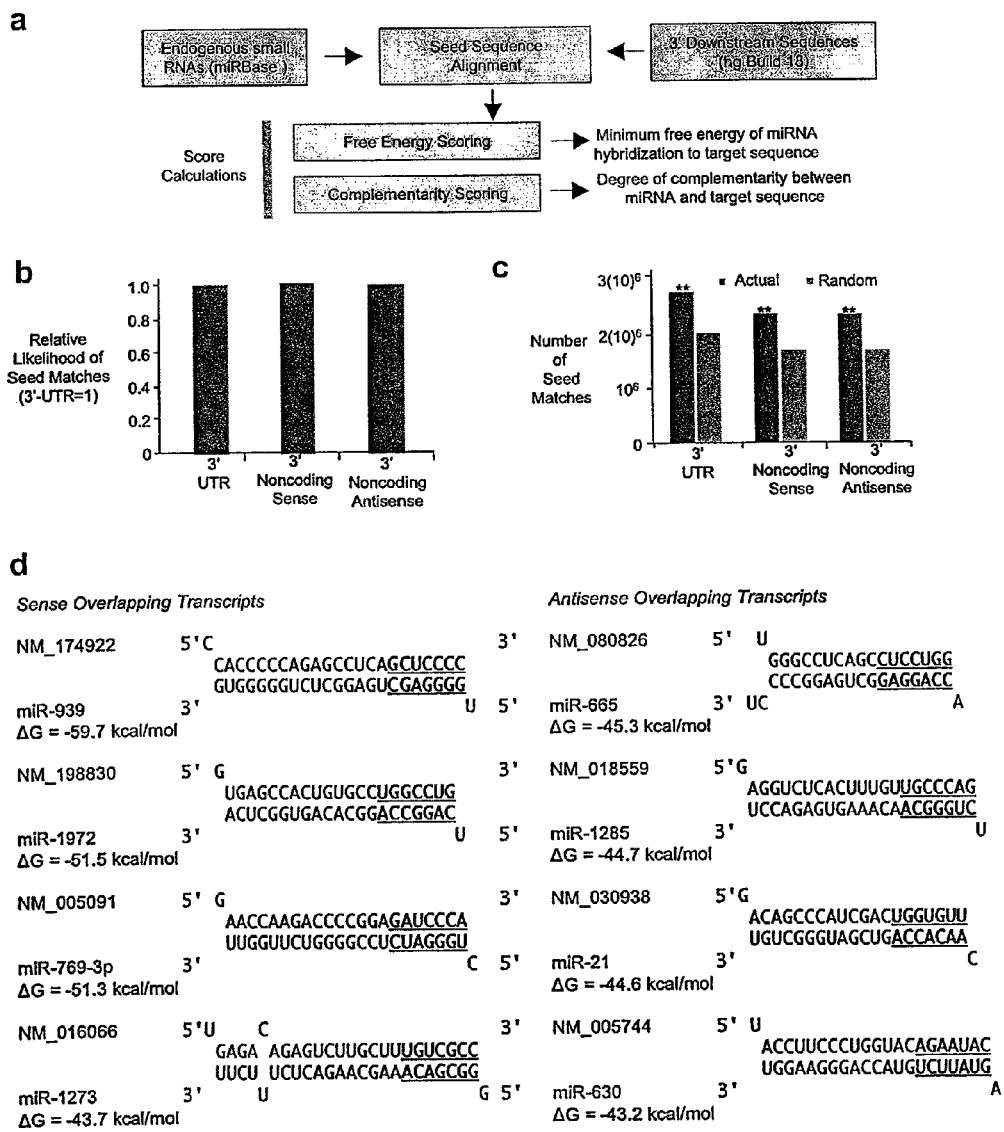
FIG. 33A-D

```
                          SEQUENCE LISTING

<160> NUMBER OF SEQ ID NOS: 202

<210> SEQ ID NO 1
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 1
ugucuggcca guccacagct t                                                   21

<210> SEQ ID NO 2
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 2
gcugucuggc caguccacat t                                                   21

<210> SEQ ID NO 3
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 3
aguugugcug cccuuccaut t                                                   21
```

```
<210> SEQ ID NO 4
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 4
cauaauccug accaaaacat t                                              21

<210> SEQ ID NO 5
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 5
uguauugagg uuuuagaugc tt                                             22

<210> SEQ ID NO 6
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 6
ccuaguaaug aaaccaaugt t                                              21

<210> SEQ ID NO 7
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 7
guauauuucu agagcuauac tt                                             22

<210> SEQ ID NO 8
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 8
guuugccugc aucaguucct t                                              21
```

```
<210> SEQ ID NO 9
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(24)
<223> OTHER INFORMATION: This is combined DNA/RNA sequence.

<400> SEQUENCE: 9
aaccagcacc ccaacuuugg actt                                            24

<210> SEQ ID NO 10
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(24)
<223> OTHER INFORMATION: This is combined DNA/RNA sequence.

<400> SEQUENCE: 10
aacuggcccu caaagucccg cutt                                            24

<210> SEQ ID NO 11
<211> LENGTH: 26
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(26)
<223> OTHER INFORMATION: This is combined DNA/RNA sequence.

<400> SEQUENCE: 11
uugcagcugc cugggaguga cuuctt                                          26

<210> SEQ ID NO 12
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(24)
<223> OTHER INFORMATION: This is combined DNA/RNA sequence.

<400> SEQUENCE: 12
ugcuggauca gugguucgag uctt                                            24

<210> SEQ ID NO 13
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(24)
<223> OTHER INFORMATION: This is combined DNA/RNA sequence.

<400> SEQUENCE: 13
caggaugugg ucaaguguug uutt                                            24
```

```
<210> SEQ ID NO 14
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(23)
<223> OTHER INFORMATION: This is combined DNA/RNA sequence.

<400> SEQUENCE: 14
uacaucagcu acuuggcau utt                                              23

<210> SEQ ID NO 15
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 15
aaaggcucug agaaagucgt t                                               21

<210> SEQ ID NO 16
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 16
uuuguuuugg cagcaacagt t                                               21

<210> SEQ ID NO 17
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 17
caucugugga uuaagcaugt t                                               21

<210> SEQ ID NO 18
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 18
cuccauuuuc ucuaucuucc tt                                              22
```

```
<210> SEQ ID NO 19
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 19
guggaaaagu gggaggacat t                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 20
uguugaugau ucugguugct t                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 21
ucucucgcca gugcacacct t                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 22
ccuaguaauc aaagcauugt t                                              21

<210> SEQ ID NO 23
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 23
guauauuuca agaccuaaac tt                                             22
```

```
<210> SEQ ID NO 24
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 24
guuuauaucu ugagcuauac tt                                              22

<210> SEQ ID NO 25
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(22)
<223> OTHER INFORMATION: This is combined DNA/RNA sequence.

<400> SEQUENCE: 25
guauuuuuca agaccuaaac tt                                              22

<210> SEQ ID NO 26
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 26
gauuggcugg aucaguucct t                                               21

<210> SEQ ID NO 27
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 27
guuuaccucc augaguacct t                                               21

<210> SEQ ID NO 28
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 28
```
ucaagaagcc aaggauaaut t                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 29
caacaucacu uuaaggaagt t                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is combined DNA/RNA sequence.

<400> SEQUENCE: 30
ucucucgcga guccacagct t                                              21

<210> SEQ ID NO 31
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(24)
<223> OTHER INFORMATION: This is combined DNA/RNA sequence.

<400> SEQUENCE: 31
aaacagcccu caaagucccg cutt                                           24

<210> SEQ ID NO 32
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(24)
<223> OTHER INFORMATION: This is combined DNA/RNA sequence.

<400> SEQUENCE: 32
aacuggcccu caacugcccg cutt                                           24

<210> SEQ ID NO 33
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(24)
<223> OTHER INFORMATION: This is combined DNA/RNA sequence.

<400> SEQUENCE: 33

```
aacuggcccu caaaguccca acuu                                          24

<210> SEQ ID NO 34
<211> LENGTH: 21
<212> TYPE: DNA
<213> ORGANISM: Artificial Sequence
<220> FEATURE:
<223> OTHER INFORMATION: Synthetic primer

<400> SEQUENCE: 34
tggtgtttgg tctaggatgg a                                             21

<210> SEQ ID NO 35
<211> LENGTH: 39
<212> TYPE: DNA
<213> ORGANISM: Artificial Sequence
<220> FEATURE:
<223> OTHER INFORMATION: Synthetic primer

<400> SEQUENCE: 35
taatacgact cactataggc accatccctg ccaatatct                          39

<210> SEQ ID NO 36
<211> LENGTH: 21
<212> TYPE: DNA
<213> ORGANISM: Artificial Sequence
<220> FEATURE:
<223> OTHER INFORMATION: Synthetic primer

<400> SEQUENCE: 36
caccttgctc ctcatttctg a                                             21

<210> SEQ ID NO 37
<211> LENGTH: 39
<212> TYPE: DNA
<213> ORGANISM: Artificial Sequence
<220> FEATURE:
<223> OTHER INFORMATION: Synthetic primer

<400> SEQUENCE: 37
taatacgact cactataggt tcaaaccacc agccaattt                          39

<210> SEQ ID NO 38
<211> LENGTH: 21
<212> TYPE: DNA
<213> ORGANISM: Artificial Sequence
<220> FEATURE:
<223> OTHER INFORMATION: Synthetic primer

<400> SEQUENCE: 38
tcaggcaatc aagttgaaac c                                             21

<210> SEQ ID NO 39
<211> LENGTH: 42
<212> TYPE: DNA
<213> ORGANISM: Artificial Sequence
<220> FEATURE:
<223> OTHER INFORMATION: Synthetic primer

<400> SEQUENCE: 39
taatacgact cactataggt tgcctgcatc agttccttat ag                      42

<210> SEQ ID NO 40
<211> LENGTH: 20
<212> TYPE: DNA
```

```
<213> ORGANISM: Artificial Sequence
<220> FEATURE:
<223> OTHER INFORMATION: Synthetic primer

<400> SEQUENCE: 40
caccgtgttc ttcgacattg                                               20

<210> SEQ ID NO 41
<211> LENGTH: 39
<212> TYPE: DNA
<213> ORGANISM: Artificial Sequence
<220> FEATURE:
<223> OTHER INFORMATION: Synthetic primer

<400> SEQUENCE: 41
taatacgact cactataggt cgagttgtcc acagtcagc                          39

<210> SEQ ID NO 42
<211> LENGTH: 20
<212> TYPE: DNA
<213> ORGANISM: Artificial Sequence
<220> FEATURE:
<223> OTHER INFORMATION: Synthetic primer

<400> SEQUENCE: 42
cttgttgtat ttgcgcgtgt                                               20

<210> SEQ ID NO 43
<211> LENGTH: 19
<212> TYPE: DNA
<213> ORGANISM: Artificial Sequence
<220> FEATURE:
<223> OTHER INFORMATION: Synthetic primer

<400> SEQUENCE: 43
gcctcgggtt gtagatttc                                                19

<210> SEQ ID NO 44
<211> LENGTH: 18
<212> TYPE: DNA
<213> ORGANISM: Artificial Sequence
<220> FEATURE:
<223> OTHER INFORMATION: Synthetic primer

<400> SEQUENCE: 44
tacaacccga ggcggcta                                                 18

<210> SEQ ID NO 45
<211> LENGTH: 19
<212> TYPE: DNA
<213> ORGANISM: Artificial Sequence
<220> FEATURE:
<223> OTHER INFORMATION: Synthetic primer

<400> SEQUENCE: 45
gaagggtcgg acttctgct                                                19

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46
gtacggagcc agcagaagtc                                               20
```

```
<210> SEQ ID NO 47
<211> LENGTH: 20
<212> TYPE: DNA
<213> ORGANISM: Artificial Sequence
<220> FEATURE:
<223> OTHER INFORMATION: Synthetic primer

<400> SEQUENCE: 47
tctctggcat caaactcgtg                                          20

<210> SEQ ID NO 48
<211> LENGTH: 20
<212> TYPE: DNA
<213> ORGANISM: Artificial Sequence
<220> FEATURE:
<223> OTHER INFORMATION: Synthetic primer

<400> SEQUENCE: 48
actggatgct gttgctctcc                                          20

<210> SEQ ID NO 49
<211> LENGTH: 20
<212> TYPE: DNA
<213> ORGANISM: Artificial Sequence
<220> FEATURE:
<223> OTHER INFORMATION: Synthetic primer

<400> SEQUENCE: 49
caggttgatc agtggtggaa                                          20

<210> SEQ ID NO 50
<211> LENGTH: 19
<212> TYPE: DNA
<213> ORGANISM: Artificial Sequence
<220> FEATURE:
<223> OTHER INFORMATION: Synthetic primer

<400> SEQUENCE: 50
cgggcactga gtgttgaat                                           19

<210> SEQ ID NO 51
<211> LENGTH: 20
<212> TYPE: DNA
<213> ORGANISM: Artificial Sequence
<220> FEATURE:
<223> OTHER INFORMATION: Synthetic primer

<400> SEQUENCE: 51
caccatccct gccaatatct                                          20

<210> SEQ ID NO 52
<211> LENGTH: 20
<212> TYPE: DNA
<213> ORGANISM: Artificial Sequence
<220> FEATURE:
<223> OTHER INFORMATION: Synthetic primer

<400> SEQUENCE: 52
atattggcag ggatggtgaa                                          20

<210> SEQ ID NO 53
<211> LENGTH: 22
<212> TYPE: DNA
<213> ORGANISM: Artificial Sequence
<220> FEATURE:
```

```
<223> OTHER INFORMATION: Synthetic primer

<400> SEQUENCE: 53
caagacctca taatcctgac ca                                              22

<210> SEQ ID NO 54
<211> LENGTH: 23
<212> TYPE: DNA
<213> ORGANISM: Artificial Sequence
<220> FEATURE:
<223> OTHER INFORMATION: Synthetic primer

<400> SEQUENCE: 54
atgtcttttt gttttggtca gga                                             23

<210> SEQ ID NO 55
<211> LENGTH: 27
<212> TYPE: DNA
<213> ORGANISM: Artificial Sequence
<220> FEATURE:
<223> OTHER INFORMATION: Synthetic primer

<400> SEQUENCE: 55
tgatgttata aatgtaaggc tttcaga                                         27

<210> SEQ ID NO 56
<211> LENGTH: 22
<212> TYPE: DNA
<213> ORGANISM: Artificial Sequence
<220> FEATURE:
<223> OTHER INFORMATION: Synthetic primer

<400> SEQUENCE: 56
tggtcaggat tatgaggtct tg                                              22

<210> SEQ ID NO 57
<211> LENGTH: 26
<212> TYPE: DNA
<213> ORGANISM: Artificial Sequence
<220> FEATURE:
<223> OTHER INFORMATION: Synthetic primer

<400> SEQUENCE: 57
aattagaacc tcacaatttt tctttt                                          26

<210> SEQ ID NO 58
<211> LENGTH: 26
<212> TYPE: DNA
<213> ORGANISM: Artificial Sequence
<220> FEATURE:
<223> OTHER INFORMATION: Synthetic primer

<400> SEQUENCE: 58
tgttttgttt acccatattt tcttga                                          26

<210> SEQ ID NO 59
<211> LENGTH: 22
<212> TYPE: DNA
<213> ORGANISM: Artificial Sequence
<220> FEATURE:
<223> OTHER INFORMATION: Synthetic primer

<400> SEQUENCE: 59
tcctcaccta catggtatga aa                                              22
```

```
<210> SEQ ID NO 60
<211> LENGTH: 25
<212> TYPE: DNA
<213> ORGANISM: Artificial Sequence
<220> FEATURE:
<223> OTHER INFORMATION: Synthetic primer

<400> SEQUENCE: 60
ccctttgtgt caattatatt tccaa                                         25

<210> SEQ ID NO 61
<211> LENGTH: 21
<212> TYPE: DNA
<213> ORGANISM: Artificial Sequence
<220> FEATURE:
<223> OTHER INFORMATION: Synthetic primer

<400> SEQUENCE: 61
tgaatttcct cctcacacaa a                                             21

<210> SEQ ID NO 62
<211> LENGTH: 20
<212> TYPE: DNA
<213> ORGANISM: Artificial Sequence
<220> FEATURE:
<223> OTHER INFORMATION: Synthetic primer

<400> SEQUENCE: 62
tgaggtattg cgagtggaca                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic primer

<400> SEQUENCE: 63
gagcaattgg caggaaagat                                               20

<210> SEQ ID NO 64
<211> LENGTH: 20
<212> TYPE: DNA
<213> ORGANISM: Artificial Sequence
<220> FEATURE:
<223> OTHER INFORMATION: Synthetic primer

<400> SEQUENCE: 64
tgtttcagcc atgcaaatct                                               20

<210> SEQ ID NO 65
<211> LENGTH: 20
<212> TYPE: DNA
<213> ORGANISM: Artificial Sequence
<220> FEATURE:
<223> OTHER INFORMATION: Synthetic primer

<400> SEQUENCE: 65
tttggctgag tctcgaaggt                                               20

<210> SEQ ID NO 66
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 66
ccacaggttt ggcttttgtt                                               20

<210> SEQ ID NO 67
<211> LENGTH: 21
<212> TYPE: DNA
<213> ORGANISM: Artificial Sequence
<220> FEATURE:
<223> OTHER INFORMATION: Synthetic primer

<400> SEQUENCE: 67
ccatttggtg aagccatatt c                                             21

<210> SEQ ID NO 68
<211> LENGTH: 20
<212> TYPE: DNA
<213> ORGANISM: Artificial Sequence
<220> FEATURE:
<223> OTHER INFORMATION: Synthetic primer

<400> SEQUENCE: 68
ccagagccat gtgcataaga                                               20

<210> SEQ ID NO 69
<211> LENGTH: 20
<212> TYPE: DNA
<213> ORGANISM: Artificial Sequence
<220> FEATURE:
<223> OTHER INFORMATION: Synthetic primer

<400> SEQUENCE: 69
atcagtgggg accacagttg                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic primer

<400> SEQUENCE: 70
taagaatttg ggggtgttgg                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic primer

<400> SEQUENCE: 71
aggagaacaa acccttggt                                                20

<210> SEQ ID NO 72
<211> LENGTH: 20
<212> TYPE: DNA
<213> ORGANISM: Artificial Sequence
<220> FEATURE:
<223> OTHER INFORMATION: Synthetic primer

<400> SEQUENCE: 72
gctcagcagc tttcattgat                                               20

<210> SEQ ID NO 73
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 73
ttctcctccc ccagaaaagt                                           20

<210> SEQ ID NO 74
<211> LENGTH: 20
<212> TYPE: DNA
<213> ORGANISM: Artificial Sequence
<220> FEATURE:
<223> OTHER INFORMATION: Synthetic primer

<400> SEQUENCE: 74
tgtgcctgac agttctcctg                                           20

<210> SEQ ID NO 75
<211> LENGTH: 21
<212> TYPE: DNA
<213> ORGANISM: Artificial Sequence
<220> FEATURE:
<223> OTHER INFORMATION: Synthetic primer

<400> SEQUENCE: 75
ccatgtgcaa aacagtcaaa g                                         21

<210> SEQ ID NO 76
<211> LENGTH: 21
<212> TYPE: DNA
<213> ORGANISM: Artificial Sequence
<220> FEATURE:
<223> OTHER INFORMATION: Synthetic primer

<400> SEQUENCE: 76
caccttgctc ctcatttctg a                                         21

<210> SEQ ID NO 77
<211> LENGTH: 20
<212> TYPE: DNA
<213> ORGANISM: Artificial Sequence
<220> FEATURE:
<223> OTHER INFORMATION: Synthetic primer

<400> SEQUENCE: 77
cccaggcata cacagatgaa                                           20

<210> SEQ ID NO 78
<211> LENGTH: 21
<212> TYPE: DNA
<213> ORGANISM: Artificial Sequence
<220> FEATURE:
<223> OTHER INFORMATION: Synthetic primer

<400> SEQUENCE: 78
tcaggcaatc aagttgaaac c                                         21

<210> SEQ ID NO 79
<211> LENGTH: 22
<212> TYPE: DNA
<213> ORGANISM: Artificial Sequence
<220> FEATURE:
<223> OTHER INFORMATION: Synthetic primer

<400> SEQUENCE: 79
```
tcaatgtgaa tagccaaaac ag                                            22

<210> SEQ ID NO 80
<211> LENGTH: 20
<212> TYPE: DNA
<213> ORGANISM: Artificial Sequence
<220> FEATURE:
<223> OTHER INFORMATION: Synthetic primer

<400> SEQUENCE: 80
catgtgcgtt gacattcaca                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic primer

<400> SEQUENCE: 81
tgattctgat ggttggtgga                                               20

<210> SEQ ID NO 82
<211> LENGTH: 20
<212> TYPE: DNA
<213> ORGANISM: Artificial Sequence
<220> FEATURE:
<223> OTHER INFORMATION: Synthetic primer

<400> SEQUENCE: 82
tgcaggacat gacaacacaa                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic primer

<400> SEQUENCE: 83
tacagcatct gcccactgac                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic primer

<400> SEQUENCE: 84
ccttaccatg tggcagatcc                                               20

<210> SEQ ID NO 85
<211> LENGTH: 20
<212> TYPE: DNA
<213> ORGANISM: Artificial Sequence
<220> FEATURE:
<223> OTHER INFORMATION: Synthetic primer

<400> SEQUENCE: 85
tgtgagctcg acacaactcc                                               20

<210> SEQ ID NO 86
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 86
cactgcacct ggcctaaact                                              20

<210> SEQ ID NO 87
<211> LENGTH: 20
<212> TYPE: DNA
<213> ORGANISM: Artificial Sequence
<220> FEATURE:
<223> OTHER INFORMATION: Synthetic primer

<400> SEQUENCE: 87
ccttgacctc ctttgctgaa                                              20

<210> SEQ ID NO 88
<211> LENGTH: 20
<212> TYPE: DNA
<213> ORGANISM: Artificial Sequence
<220> FEATURE:
<223> OTHER INFORMATION: Synthetic primer

<400> SEQUENCE: 88
ttcagcaaag gaggtcaagg                                              20

<210> SEQ ID NO 89
<211> LENGTH: 20
<212> TYPE: DNA
<213> ORGANISM: Artificial Sequence
<220> FEATURE:
<223> OTHER INFORMATION: Synthetic primer

<400> SEQUENCE: 89
caatctgtcc catgcagaaa                                              20

<210> SEQ ID NO 90
<211> LENGTH: 29
<212> TYPE: DNA
<213> ORGANISM: Artificial Sequence
<220> FEATURE:
<223> OTHER INFORMATION: Synthetic primer

<400> SEQUENCE: 90
ggcactggct ggtaacagat gcaaaactg                                    29

<210> SEQ ID NO 91
<211> LENGTH: 30
<212> TYPE: DNA
<213> ORGANISM: Artificial Sequence
<220> FEATURE:
<223> OTHER INFORMATION: Synthetic primer

<400> SEQUENCE: 91
ttggcaagag atgcagggaa tctttctcat                                   30

<210> SEQ ID NO 92
<211> LENGTH: 32
<212> TYPE: DNA
<213> ORGANISM: Artificial Sequence
<220> FEATURE:
<223> OTHER INFORMATION: Synthetic primer

<400> SEQUENCE: 92
gcaaagcaaa gagtgattct caggcaatca ag                                32
```

```
<210> SEQ ID NO 93
<211> LENGTH: 35
<212> TYPE: DNA
<213> ORGANISM: Artificial Sequence
<220> FEATURE:
<223> OTHER INFORMATION: Synthetic primer

<400> SEQUENCE: 93
gcctaaattc tataaggaac tgatgcaggc aaacc                              35

<210> SEQ ID NO 94
<211> LENGTH: 32
<212> TYPE: DNA
<213> ORGANISM: Artificial Sequence
<220> FEATURE:
<223> OTHER INFORMATION: Synthetic primer

<400> SEQUENCE: 94
tgattgcctg agaatcactc tttgctttgc ta                                 32

<210> SEQ ID NO 95
<211> LENGTH: 33
<212> TYPE: DNA
<213> ORGANISM: Artificial Sequence
<220> FEATURE:
<223> OTHER INFORMATION: Synthetic primer

<400> SEQUENCE: 95
cactgtgtag ttggtttcaa cttgattgcc tga                                33

<210> SEQ ID NO 96
<211> LENGTH: 20
<212> TYPE: DNA
<213> ORGANISM: Artificial Sequence
<220> FEATURE:
<223> OTHER INFORMATION: Synthetic primer

<400> SEQUENCE: 96
ggaggaggcg ttgttagaaa                                               20

<210> SEQ ID NO 97
<211> LENGTH: 19
<212> TYPE: DNA
<213> ORGANISM: Artificial Sequence
<220> FEATURE:
<223> OTHER INFORMATION: Synthetic primer

<400> SEQUENCE: 97
gaagggtcgg acttctgct                                                19

<210> SEQ ID NO 98
<211> LENGTH: 20
<212> TYPE: DNA
<213> ORGANISM: Artificial Sequence
<220> FEATURE:
<223> OTHER INFORMATION: Synthetic primer

<400> SEQUENCE: 98
caaaaagggt ccggtgtaga                                               20

<210> SEQ ID NO 99
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 99
aggcactgct ccactgtctt                                              20

<210> SEQ ID NO 100
<211> LENGTH: 28
<212> TYPE: DNA
<213> ORGANISM: Artificial Sequence
<220> FEATURE:
<223> OTHER INFORMATION: Synthetic primer

<400> SEQUENCE: 100
ttcagactac attggtttca ttactagg                                     28

<210> SEQ ID NO 101
<211> LENGTH: 23
<212> TYPE: DNA
<213> ORGANISM: Artificial Sequence
<220> FEATURE:
<223> OTHER INFORMATION: Synthetic primer

<400> SEQUENCE: 101
ttgcctgcat cagttcctta tag                                          23

<210> SEQ ID NO 102
<211> LENGTH: 20
<212> TYPE: DNA
<213> ORGANISM: Artificial Sequence
<220> FEATURE:
<223> OTHER INFORMATION: Synthetic primer

<400> SEQUENCE: 102
gcgcgggaat tacagataaa                                              20

<210> SEQ ID NO 103
<211> LENGTH: 20
<212> TYPE: DNA
<213> ORGANISM: Artificial Sequence
<220> FEATURE:
<223> OTHER INFORMATION: Synthetic primer

<400> SEQUENCE: 103
tacccagagc agagggtgaa                                              20

<210> SEQ ID NO 104
<211> LENGTH: 20
<212> TYPE: DNA
<213> ORGANISM: Artificial Sequence
<220> FEATURE:
<223> OTHER INFORMATION: Synthetic primer

<400> SEQUENCE: 104
acctgcgaaa tccagaacaa                                              20

<210> SEQ ID NO 105
<211> LENGTH: 21
<212> TYPE: DNA
<213> ORGANISM: Artificial Sequence
<220> FEATURE:
<223> OTHER INFORMATION: Synthetic primer

<400> SEQUENCE: 105
tgtgctgagc aaggatcata a                                            21

<210> SEQ ID NO 106
```

```
<210> SEQ ID NO 106
<211> LENGTH: 28
<212> TYPE: DNA
<213> ORGANISM: Artificial Sequence
<220> FEATURE:
<223> OTHER INFORMATION: Synthetic primer

<400> SEQUENCE: 106
ttcagactac attggtttca ttactagg                                    28

<210> SEQ ID NO 107
<211> LENGTH: 23
<212> TYPE: DNA
<213> ORGANISM: Artificial Sequence
<220> FEATURE:
<223> OTHER INFORMATION: Synthetic primer

<400> SEQUENCE: 107
ttgcctgcat cagttcctta tag                                         23

<210> SEQ ID NO 108
<211> LENGTH: 20
<212> TYPE: DNA
<213> ORGANISM: Artificial Sequence
<220> FEATURE:
<223> OTHER INFORMATION: Synthetic primer

<400> SEQUENCE: 108
ggaggaggcg ttgttagaaa                                             20

<210> SEQ ID NO 109
<211> LENGTH: 19
<212> TYPE: DNA
<213> ORGANISM: Artificial Sequence
<220> FEATURE:
<223> OTHER INFORMATION: Synthetic primer

<400> SEQUENCE: 109
gaagggtcgg acttctgct                                              19

<210> SEQ ID NO 110
<211> LENGTH: 20
<212> TYPE: DNA
<213> ORGANISM: Artificial Sequence
<220> FEATURE:
<223> OTHER INFORMATION: Synthetic primer

<400> SEQUENCE: 110
gcgcgggaat tacagataaa                                             20

<210> SEQ ID NO 111
<211> LENGTH: 20
<212> TYPE: DNA
<213> ORGANISM: Artificial Sequence
<220> FEATURE:
<223> OTHER INFORMATION: Synthetic primer

<400> SEQUENCE: 111
tacccagagc agagggtgaa                                             20

<210> SEQ ID NO 112
<211> LENGTH: 20
<212> TYPE: DNA
<213> ORGANISM: Artificial Sequence
<220> FEATURE:
<223> OTHER INFORMATION: Synthetic primer

<400> SEQUENCE: 112
```

```
tgcaggacat gacaacacaa                                              20

<210> SEQ ID NO 113
<211> LENGTH: 20
<212> TYPE: DNA
<213> ORGANISM: Artificial Sequence
<220> FEATURE:
<223> OTHER INFORMATION: Synthetic primer

<400> SEQUENCE: 113
tacagcatct gcccactgac                                              20

<210> SEQ ID NO 114
<211> LENGTH: 21
<212> TYPE: DNA
<213> ORGANISM: Artificial Sequence
<220> FEATURE:
<223> OTHER INFORMATION: Synthetic primer

<400> SEQUENCE: 114
taaggaactg atgcaggcaa a                                            21

<210> SEQ ID NO 115
<211> LENGTH: 20
<212> TYPE: DNA
<213> ORGANISM: Artificial Sequence
<220> FEATURE:
<223> OTHER INFORMATION: Synthetic primer

<400> SEQUENCE: 115
aagccaaaaa tcctcccaag                                              20

<210> SEQ ID NO 116
<211> LENGTH: 20
<212> TYPE: DNA
<213> ORGANISM: Artificial Sequence
<220> FEATURE:
<223> OTHER INFORMATION: Synthetic primer

<400> SEQUENCE: 116
cctagaggag gaggcgttgt                                              20

<210> SEQ ID NO 117
<211> LENGTH: 19
<212> TYPE: DNA
<213> ORGANISM: Artificial Sequence
<220> FEATURE:
<223> OTHER INFORMATION: Synthetic primer

<400> SEQUENCE: 117
attgagaatg ccacccaca                                               19

<210> SEQ ID NO 118
<211> LENGTH: 20
<212> TYPE: DNA
<213> ORGANISM: Artificial Sequence
<220> FEATURE:
<223> OTHER INFORMATION: Synthetic primer

<400> SEQUENCE: 118
ggaggaggcg ttgttagaaa                                              20

<210> SEQ ID NO 119
<211> LENGTH: 19
<212> TYPE: DNA
```

```
<213> ORGANISM: Artificial Sequence
<220> FEATURE:
<223> OTHER INFORMATION: Synthetic primer

<400> SEQUENCE: 119
gaagggtcgg acttctgct                                                    19

<210> SEQ ID NO 120
<211> LENGTH: 26
<212> TYPE: DNA
<213> ORGANISM: Artificial Sequence
<220> FEATURE:
<223> OTHER INFORMATION: Synthetic primer

<400> SEQUENCE: 120
cagactacat tggtttcatt actagg                                            26

<210> SEQ ID NO 121
<211> LENGTH: 27
<212> TYPE: DNA
<213> ORGANISM: Artificial Sequence
<220> FEATURE:
<223> OTHER INFORMATION: Synthetic primer

<400> SEQUENCE: 121
gcatttattt tatttactaa aggagca                                           27

<210> SEQ ID NO 122
<211> LENGTH: 21
<212> TYPE: DNA
<213> ORGANISM: Artificial Sequence
<220> FEATURE:
<223> OTHER INFORMATION: Synthetic primer

<400> SEQUENCE: 122
taaggaactg atgcaggcaa a                                                 21

<210> SEQ ID NO 123
<211> LENGTH: 20
<212> TYPE: DNA
<213> ORGANISM: Artificial Sequence
<220> FEATURE:
<223> OTHER INFORMATION: Synthetic primer

<400> SEQUENCE: 123
aagccaaaaa tcctcccaag                                                   20

<210> SEQ ID NO 124
<211> LENGTH: 28
<212> TYPE: DNA
<213> ORGANISM: Artificial Sequence
<220> FEATURE:
<223> OTHER INFORMATION: Synthetic primer

<400> SEQUENCE: 124
ttcagactac attggtttca ttactagg                                          28

<210> SEQ ID NO 125
<211> LENGTH: 23
<212> TYPE: DNA
<213> ORGANISM: Artificial Sequence
<220> FEATURE:
<223> OTHER INFORMATION: Synthetic primer

<400> SEQUENCE: 125
ttgcctgcat cagttcctta tag                                               23
```

<210> SEQ ID NO 126
<211> LENGTH: 20
<212> TYPE: DNA
<213> ORGANISM: Artificial Sequence
<220> FEATURE:
<223> OTHER INFORMATION: Synthetic primer

<400> SEQUENCE: 126
cctagaggag gaggcgttgt                                               20

<210> SEQ ID NO 127
<211> LENGTH: 19
<212> TYPE: DNA
<213> ORGANISM: Artificial Sequence
<220> FEATURE:
<223> OTHER INFORMATION: Synthetic primer

<400> SEQUENCE: 127
attgagaatg ccacccaca                                                19

<210> SEQ ID NO 128
<211> LENGTH: 20
<212> TYPE: DNA
<213> ORGANISM: Artificial Sequence
<220> FEATURE:
<223> OTHER INFORMATION: Synthetic primer

<400> SEQUENCE: 128
agtttaggcc aggtgcagtg                                               20

<210> SEQ ID NO 129
<211> LENGTH: 20
<212> TYPE: DNA
<213> ORGANISM: Artificial Sequence
<220> FEATURE:
<223> OTHER INFORMATION: Synthetic primer

<400> SEQUENCE: 129
tagctgattt gggccagttt                                               20

<210> SEQ ID NO 130
<211> LENGTH: 22
<212> TYPE: DNA
<213> ORGANISM: Artificial Sequence
<220> FEATURE:
<223> OTHER INFORMATION: Synthetic primer

<400> SEQUENCE: 130
tgttaatgag cattgaacca ga                                            22

<210> SEQ ID NO 131
<211> LENGTH: 20
<212> TYPE: DNA
<213> ORGANISM: Artificial Sequence
<220> FEATURE:
<223> OTHER INFORMATION: Synthetic primer

<400> SEQUENCE: 131
atcatctgcc cctgttgaaa                                               20

<210> SEQ ID NO 132
<211> LENGTH: 20
<212> TYPE: DNA
<213> ORGANISM: Artificial Sequence
<220> FEATURE:

<223> OTHER INFORMATION: Synthetic primer

<400> SEQUENCE: 132
tccttacctg tgggagctgt                                                      20

<210> SEQ ID NO 133
<211> LENGTH: 20
<212> TYPE: DNA
<213> ORGANISM: Artificial Sequence
<220> FEATURE:
<223> OTHER INFORMATION: Synthetic primer

<400> SEQUENCE: 133
ggagaactcc ccgagttagg                                                      20

<210> SEQ ID NO 134
<211> LENGTH: 19
<212> TYPE: DNA
<213> ORGANISM: Artificial Sequence
<220> FEATURE:
<223> OTHER INFORMATION: Synthetic primer

<400> SEQUENCE: 134
gaagggtcgg acttctgct                                                       19

<210> SEQ ID NO 135
<211> LENGTH: 18
<212> TYPE: DNA
<213> ORGANISM: Artificial Sequence
<220> FEATURE:
<223> OTHER INFORMATION: Synthetic primer

<400> SEQUENCE: 135
tacaacccga ggcggcta                                                        18

<210> SEQ ID NO 136
<211> LENGTH: 20
<212> TYPE: DNA
<213> ORGANISM: Artificial Sequence
<220> FEATURE:
<223> OTHER INFORMATION: Synthetic primer

<400> SEQUENCE: 136
tctaacaacg cctcctcctc                                                      20

<210> SEQ ID NO 137
<211> LENGTH: 22
<212> TYPE: DNA
<213> ORGANISM: Artificial Sequence
<220> FEATURE:
<223> OTHER INFORMATION: Synthetic primer

<400> SEQUENCE: 137
ggtgcatata aaatcctcag gc                                                   22

<210> SEQ ID NO 138
<211> LENGTH: 18
<212> TYPE: DNA
<213> ORGANISM: Artificial Sequence
<220> FEATURE:
<223> OTHER INFORMATION: Synthetic primer

<400> SEQUENCE: 138
gctcctcagc gcccggtc                                                        18

```
<210> SEQ ID NO 139
<211> LENGTH: 22
<212> TYPE: DNA
<213> ORGANISM: Artificial Sequence
<220> FEATURE:
<223> OTHER INFORMATION: Synthetic primer

<400> SEQUENCE: 139
gtattctttg acgggggta gg                                                 22

<210> SEQ ID NO 140
<211> LENGTH: 20
<212> TYPE: DNA
<213> ORGANISM: Artificial Sequence
<220> FEATURE:
<223> OTHER INFORMATION: Synthetic primer

<400> SEQUENCE: 140
gctccatcac ttgaaatggc                                                   20

<210> SEQ ID NO 141
<211> LENGTH: 21
<212> TYPE: DNA
<213> ORGANISM: Artificial Sequence
<220> FEATURE:
<223> OTHER INFORMATION: Synthetic primer

<400> SEQUENCE: 141
cactgccctg tgctatgtca a                                                 21

<210> SEQ ID NO 142
<211> LENGTH: 19
<212> TYPE: DNA
<213> ORGANISM: Artificial Sequence
<220> FEATURE:
<223> OTHER INFORMATION: Synthetic primer

<400> SEQUENCE: 142
ccagcctggg tgacagagc                                                    19

<210> SEQ ID NO 143
<211> LENGTH: 24
<212> TYPE: DNA
<213> ORGANISM: Artificial Sequence
<220> FEATURE:
<223> OTHER INFORMATION: Synthetic primer

<400> SEQUENCE: 143
ggcttggcct caagagaata gctg                                              24

<210> SEQ ID NO 144
<211> LENGTH: 19
<212> TYPE: DNA
<213> ORGANISM: Artificial Sequence
<220> FEATURE:
<223> OTHER INFORMATION: Synthetic primer

<400> SEQUENCE: 144
ccggtcatgg tggtggaca                                                    19

<210> SEQ ID NO 145
<211> LENGTH: 25
<212> TYPE: DNA
<213> ORGANISM: Artificial Sequence
<220> FEATURE:
<223> OTHER INFORMATION: Synthetic primer
```

```
<400> SEQUENCE: 145
catgaggcca aaataaaggt gttcg                                     25

<210> SEQ ID NO 146
<211> LENGTH: 20
<212> TYPE: DNA
<213> ORGANISM: Artificial Sequence
<220> FEATURE:
<223> OTHER INFORMATION: Synthetic primer

<400> SEQUENCE: 146
atgacagatc ccaccaggaa                                           20

<210> SEQ ID NO 147
<211> LENGTH: 20
<212> TYPE: DNA
<213> ORGANISM: Artificial Sequence
<220> FEATURE:
<223> OTHER INFORMATION: Synthetic primer

<400> SEQUENCE: 147
caacagggag caaaggaaaa                                           20

<210> SEQ ID NO 148
<211> LENGTH: 19
<212> TYPE: DNA
<213> ORGANISM: Artificial Sequence
<220> FEATURE:
<223> OTHER INFORMATION: Synthetic primer

<400> SEQUENCE: 148
acttaggcca gcgactttc                                            19

<210> SEQ ID NO 149
<211> LENGTH: 20
<212> TYPE: DNA
<213> ORGANISM: Artificial Sequence
<220> FEATURE:
<223> OTHER INFORMATION: Synthetic primer

<400> SEQUENCE: 149
tactatcatt accccattt                                            20

<210> SEQ ID NO 150
<211> LENGTH: 20
<212> TYPE: DNA
<213> ORGANISM: Artificial Sequence
<220> FEATURE:
<223> OTHER INFORMATION: Synthetic primer

<400> SEQUENCE: 150
atttcctgtt gctgccaaaa                                           20

<210> SEQ ID NO 151
<211> LENGTH: 20
<212> TYPE: DNA
<213> ORGANISM: Artificial Sequence
<220> FEATURE:
<223> OTHER INFORMATION: Synthetic primer

<400> SEQUENCE: 151
ggcctcatga aacctgaaac                                           20

<210> SEQ ID NO 152
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 152
ggccaaaata aaggtgttcg                                              20

<210> SEQ ID NO 153
<211> LENGTH: 20
<212> TYPE: DNA
<213> ORGANISM: Artificial Sequence
<220> FEATURE:
<223> OTHER INFORMATION: Synthetic primer

<400> SEQUENCE: 153
agaactgcaa ggacccagag                                              20

<210> SEQ ID NO 154
<211> LENGTH: 33
<212> TYPE: DNA
<213> ORGANISM: Artificial Sequence
<220> FEATURE:
<223> OTHER INFORMATION: Synthetic primer

<400> SEQUENCE: 154
cactgtgtag ttggtttcaa cttgattgcc tga                               33

<210> SEQ ID NO 155
<211> LENGTH: 32
<212> TYPE: DNA
<213> ORGANISM: Artificial Sequence
<220> FEATURE:
<223> OTHER INFORMATION: Synthetic primer

<400> SEQUENCE: 155
tgattgcctg agaatcactc tttgctttgc ta                                32

<210> SEQ ID NO 156
<211> LENGTH: 32
<212> TYPE: DNA
<213> ORGANISM: Artificial Sequence
<220> FEATURE:
<223> OTHER INFORMATION: Synthetic primer

<400> SEQUENCE: 156
gcaaagcaaa gagtgattct caggcaatca ag                                32

<210> SEQ ID NO 157
<211> LENGTH: 35
<212> TYPE: DNA
<213> ORGANISM: Artificial Sequence
<220> FEATURE:
<223> OTHER INFORMATION: Synthetic primer

<400> SEQUENCE: 157
gcctaaattc tataaggaac tgatgcaggc aaacc                             35

<210> SEQ ID NO 158
<211> LENGTH: 30
<212> TYPE: DNA
<213> ORGANISM: Artificial Sequence
<220> FEATURE:
<223> OTHER INFORMATION: Synthetic primer

<400> SEQUENCE: 158
```
ccatttcttg ctggcttagc acattcctca                                  30

<210> SEQ ID NO 159
<211> LENGTH: 34
<212> TYPE: DNA
<213> ORGANISM: Artificial Sequence
<220> FEATURE:
<223> OTHER INFORMATION: Synthetic primer

<400> SEQUENCE: 159
cagtgacata tagtgacaca agggaaaagt ctca                             34

<210> SEQ ID NO 160
<211> LENGTH: 30
<212> TYPE: DNA
<213> ORGANISM: Artificial Sequence
<220> FEATURE:
<223> OTHER INFORMATION: Synthetic primer

<400> SEQUENCE: 160
agggagcact ggtgagcagt aggttgaaga                                  30

<210> SEQ ID NO 161
<211> LENGTH: 31
<212> TYPE: DNA
<213> ORGANISM: Artificial Sequence
<220> FEATURE:
<223> OTHER INFORMATION: Synthetic primer

<400> SEQUENCE: 161
tccaaattgc tcacaaataa ctggtcatgg a                                31

<210> SEQ ID NO 162
<211> LENGTH: 36
<212> TYPE: DNA
<213> ORGANISM: Artificial Sequence
<220> FEATURE:
<223> OTHER INFORMATION: Synthetic primer

<400> SEQUENCE: 162
tcaactcaaa cttacagcaa gaatcctgtt ccactc                           36

<210> SEQ ID NO 163
<211> LENGTH: 28
<212> TYPE: DNA
<213> ORGANISM: Artificial Sequence
<220> FEATURE:
<223> OTHER INFORMATION: Synthetic primer

<400> SEQUENCE: 163
agaaacgctg tgagctcgac acaactcc                                    28

<210> SEQ ID NO 164
<211> LENGTH: 32
<212> TYPE: RNA
<213> ORGANISM: Artificial Sequence
<220> FEATURE:
<223> OTHER INFORMATION: Synthetic primer

<400> SEQUENCE: 164
uuaaaguggu gcugguaguu ucaccacgac ca                               32

<210> SEQ ID NO 165
<211> LENGTH: 32
<212> TYPE: RNA
<213> ORGANISM: Artificial Sequence

```
<220> FEATURE:
<223> OTHER INFORMATION: Synthetic primer

<400> SEQUENCE: 165
agcgauuugg gccaguucgc ugaacccggu ca                                32

<210> SEQ ID NO 166
<211> LENGTH: 34
<212> TYPE: RNA
<213> ORGANISM: Artificial Sequence
<220> FEATURE:
<223> OTHER INFORMATION: Synthetic primer

<400> SEQUENCE: 166
ucacuuucgg agcugcaagu gagggccucg acgu                              34

<210> SEQ ID NO 167
<211> LENGTH: 34
<212> TYPE: RNA
<213> ORGANISM: Artificial Sequence
<220> FEATURE:
<223> OTHER INFORMATION: Synthetic primer

<400> SEQUENCE: 167
auugagcacg auccagcuga cuugugcuag gucg                              34

<210> SEQ ID NO 168
<211> LENGTH: 32
<212> TYPE: RNA
<213> ORGANISM: Artificial Sequence
<220> FEATURE:
<223> OTHER INFORMATION: Synthetic primer

<400> SEQUENCE: 168
cagcuugcua cauccuguug aaugguguag ga                                32

<210> SEQ ID NO 169
<211> LENGTH: 3247
<212> TYPE: DNA
<213> ORGANISM: Artificial Sequence
<220> FEATURE:
<223> OTHER INFORMATION: Synthetic primer

<400> SEQUENCE: 169
gtttctttct ccaggtcctc actggccata caccagtccc ttgttagtta tgcctggtca    60 tagaccccccc gttgctatca tctcatattt aagtctttgg cttgtgaatt tatctattct  120
ttcagcttca gcactgcaga gtgctgggac tttgctaact tccatttctt gctggcttag  180
cacattcctc ataggcccag ctctttctc atctggccct gctgtggagt caccttgccc   240
cttcaggaga gccatggctt accactgcct gctaagcctc cactcagctg ccaccacact   300
aaatccaagc ttctctaaga tgttgcagac tttacaggca agcataaaag gcttgatctt   360
cctggacttc cctttacttg tctgaatctc acctccttca actttcagtc tcagaatgta   420
ggcatttgtc ctctttgccc tacatcttcc ttcttctgaa tcatgaaagc ctctcacttc   480
ctcttgctat gtgctggagg cttctgtcag gtttttagaat gagttctcat ctagtcctag  540
tagcttttga tgcttaagtc caccttttaa ggatacctttt gagatttaga ccatgttttt   600
cgcttgagaa agccctaatc tccagacttg cctttctgtg gatttcaaag accaactgag   660
gaagtcaaaa gctgaatgtt gactttcttt gaacatttcc gctataacaa ttccaattct   720
cctcagagca atatgcctgc ctccaactga ccaggagaaa ggtccagtgc caaagagaaa   780
```

```
aacacaaaga ttaattattt cagttgagca catactttca aagtggtttg ggtattcata      840
tgaggttttc tgtcaagagg gtgagactct tcatctatcc atgtgtgcct gacagttctc      900
ctggcactgg ctggtaacag atgcaaaact gtaaaaatta agtgatcatg tattttaacg      960
atatcatcac atacttattt tctatgtaat gttttaaatt tcccctaaca tactttgact     1020
gttttgcaca tggtagatat tcacattttt ttgtgttgaa gttgatgcaa tcttcaaagt     1080
tatctacccc gttgcttatt agtaaaacta gtgttaatac ttggcaagag atgcagggaa     1140
tctttctcat gactcacgcc ctatttagtt attaatgcta ctaccctatt ttgagtaagt     1200
agtaggtccc taagtacatt gtccagagtt atacttttaa agatatttag ccccatatac     1260
ttcttgaatc taaagtcata caccttgctc ctcatttctg agtgggaaag acatttgaga     1320
gtatgttgac aattgttctg aaggttttg ccaagaaggt gaaactgtcc tttcatctgt      1380
gtatgcctgg ggctgggtcc ctggcagtga tggggtgaca atgcaaagct gtaaaaacta     1440
ggtgctagtg ggcacctaat atcatcatca tatacttatt ttcaagctaa tatgcaaaat     1500
cccatctctg ttttaaact aagtgtagat ttcagagaaa atattttgtg gttcacataa      1560
gaaaacagtc tactcagctt gacaagtgtt ttatgttaaa ttggctggtg gtttgaaatg     1620
aatcatcttc acataatgtt ttcttttaaaa atattgtgaa tttaactcta attcttgtta    1680
ttctgtgtga taataaagaa taaactaatt tctatatctc tctttattaa tgaattatag     1740
catctaaaac ctcaatacaa ttacatacaa gacacacact aatcatcagt agtacattct     1800
ttaccagtca tttaaaattt ataaccaaca tttcaatttg tacaatactg tatgtggcat     1860
aaggtgagat atttatatgg aagatttggc attatagaga aaatatcctt gactgggtat     1920
gcattttagc aaagcaaaga gtgattctca ggcaatcaag ttgaaaccaa ctacacagtg     1980
tttcaatcag aaagacaaaa tacaatcaac tgacatctag tgagattcaa taatatactg     2040
ttttggctat tcacattgat taaaaagttt ggtattatac aagaattttc atatgaaatt     2100
taatgcattt cacattaagg tgaatgatat tctacttgta ataacaaagt atttcagact     2160
acattggttt cattactagg aatataattt agtatagctc tagaaatata caaatatgct     2220
cctttagtaa ataaaataaa tgcctaaatt ctataaggaa ctgatgcagg caaaccctaa     2280
aatgggggct cagcttggga ggattttttgg cttaattcag aaaagaattc aagagggaac    2340
ccacagtgaa agaagccaag tttattggag caacagcatc cagcaaaatg gctactccac     2400
aggcagagta gccctcgtgg gttgctggct agctatatgt ataccaactc ttaattatat     2460
gctaaatatg aggtctgtta ttcacagatt ttctggaaaa gctgcaggga gttcttggaa     2520
ctatataact taatttctgg gtgttcccat ggcatttgta aagtgtcatg gtgctggtgc     2580
agtgtctcat agcctgcaga tgcattataa tttctagtcc tagctgattt gggccagttt     2640
cttagctaca tcctgttttt gatcagcagg gtcatgaaaa caagtcctgg tgatctttta     2700
cctcagaacc atgttaggtc ttggagacac aaagataaat gagtggaaca ggattcttgc     2760
tgtaagtttg agttgataca atgccacata ttattgtttg aaatgtcaaa atacttgttt     2820
cttattgaat caactagatt tggaatagac tggaaaatct ggaaagcttt attggatcat     2880
ttttcctatc acttaaacac tattttttcc tggttaatac catgttttcg gttttttaaaa    2940 catgccacca tattcagatt tacaaatgta aatacggttg agaaacttcg tatttaccta    3000
tgaaacaaca tgctgttttt tataaatact tgattctgat ggttggtgga gttttttccaa   3060 tcaaagttaa ctaatgaata aagagaaaat gtggcaagtg gctgtgaatg tcaacgcaca    3120
tgagactttt cccttgtgtc actatatgtc actgtatgga gtcactataa caaactaaga    3180
```

```
gtatagctct ctctacacta atcatgaata aatacttaat atcaaaaaaa aaaaaaaaa    3240 aaaaaaa                                                              3247

<210> SEQ ID NO 170
<211> LENGTH: 20
<212> TYPE: DNA
<213> ORGANISM: Artificial Sequence
<220> FEATURE:
<223> OTHER INFORMATION: Synthetic primer

<400> SEQUENCE: 170
gtatagctct agaaatatac                                                  20

<210> SEQ ID NO 171
<211> LENGTH: 19
<212> TYPE: DNA
<213> ORGANISM: Artificial Sequence
<220> FEATURE:
<223> OTHER INFORMATION: Synthetic primer

<400> SEQUENCE: 171
ggaactgatg caggcaaac                                                   19

<210> SEQ ID NO 172
<211> LENGTH: 162
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (4)..(5)
<223> OTHER INFORMATION: n is a, c, g, or t

<400> SEQUENCE: 172
tccnnaagaa cctgctattg agagtagcat tcagaataac gggtggaaat gccaactcca     60
gagtttcaga tcaaaaacag gatgtagcta agaaactggc ccaaatcagc taggactaga   120
aattataatg catctgcagg ctatgagaca ctgcaccagc ac                      162

<210> SEQ ID NO 173
<211> LENGTH: 91
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 173
ggnncggant tctgctggct ccgtactgcg ggcgacagtc atctccgaag atcaaaaaca     60
ggatgtagct aggactggcc caaatcagct a                                    91

<210> SEQ ID NO 174
<211> LENGTH: 168
<212> TYPE: DNA
<213> ORGANISM: Artificial Sequence
<220> FEATURE:
<223> OTHER INFORMATION: Synthetic primer
<220> FEATURE:
```

```
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 174
tgtgntggtg nagtgtctca tagcctgcag atgcattata atttctagtc ctagctgatt     60
tgggccagtt tcttagctac atcctgtttt tgatctgaaa ctctggagtt ggcatttcca    120
cccgttattc tgaatgctac tctcaatagc aggttctttg ggatggaa                  168

<210> SEQ ID NO 175
<211> LENGTH: 154
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 175
ttgaggnncg ganttctgct ggctccgtac tgcgggcgac agtcatctcc gaagatctca     60
gatcaaaaac aggatgtagc taagaaactg gcccaaatca gctaggacta gaaattataa    120
tgcatctgca ggctatgaga cactgcacca gcac                                 154

<210> SEQ ID NO 176
<211> LENGTH: 120
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or t

<400> SEQUENCE: 176
cgganttctg ctggctccgt actgcgggcg acagtcatct ccgaagatca ccaggacttg     60
ttttcatgac cctgctgatc aaaaacagga tgtagctaag aaactggccc aaatcagcta    120

<210> SEQ ID NO 177
<211> LENGTH: 81
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (22)..(23)
<223> OTHER INFORMATION: n is a, c, g, or t

<400> SEQUENCE: 177
tttacacccg aggcggctag tnntcccgca ctactgggat caaaaacacg atgtagctaa     60
gaaactggcc caaatcagct a                                                81

<210> SEQ ID NO 178
<211> LENGTH: 177
```

-continued

```
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(15)
<223> OTHER INFORMATION: n is a, c, g, or t

<400> SEQUENCE: 178
tctttgacgg ggggnagggg cggaacctga gaggcgtaag gcgttgtgaa ccctggggag    60
gggggcagtt tgtaggtcgc gagggaagcg ctgaggatct tagtcctaga actgcaagga   120
cccagagcct ctagaaggga acacgccctg cgaacacctt tattttggcc tcatgaa     177

<210> SEQ ID NO 179
<211> LENGTH: 47
<212> TYPE: RNA
<213> ORGANISM: Artificial Sequence
<220> FEATURE:
<223> OTHER INFORMATION: Synthetic primer

<400> SEQUENCE: 179 ccaccccag accucagcuc cccgugggggu ucucggaguc gagggu                   47

<210> SEQ ID NO 180
<211> LENGTH: 44
<212> TYPE: RNA
<213> ORGANISM: Artificial Sequence
<220> FEATURE:
<223> OTHER INFORMATION: Synthetic primer

<400> SEQUENCE: 180
gugagccacu gugccuggcc ugacucggug acacggaccg gacu                     44

<210> SEQ ID NO 181
<211> LENGTH: 46
<212> TYPE: RNA
<213> ORGANISM: Artificial Sequence
<220> FEATURE:
<223> OTHER INFORMATION: Synthetic primer

<400> SEQUENCE: 181
gaaccaagac cccggagauc ccauugguuc uggggccucu aggguc                   46

<210> SEQ ID NO 182
<211> LENGTH: 49
<212> TYPE: RNA
<213> ORGANISM: Artificial Sequence
<220> FEATURE:
<223> OTHER INFORMATION: Synthetic primer

<400> SEQUENCE: 182
ucgagaagag ucuugcuuug ucgccuucuu cucagaacga aacagcggu                49

<210> SEQ ID NO 183
<211> LENGTH: 38
<212> TYPE: RNA
<213> ORGANISM: Artificial Sequence
<220> FEATURE:
<223> OTHER INFORMATION: Synthetic primer

<400> SEQUENCE: 183
ugggccucag ccuccuggcc cggagucgga ggaccuca                            38

<210> SEQ ID NO 184
```

```
<211> LENGTH: 44
<212> TYPE: RNA
<213> ORGANISM: Artificial Sequence
<220> FEATURE:
<223> OTHER INFORMATION: Synthetic primer

<400> SEQUENCE: 184
gaggucucac uuuguugccc aguccagagu gaaacaacgg gucu          44

<210> SEQ ID NO 185
<211> LENGTH: 42
<212> TYPE: RNA
<213> ORGANISM: Artificial Sequence
<220> FEATURE:
<223> OTHER INFORMATION: Synthetic primer

<400> SEQUENCE: 185
gacagcccau cgacuggugu uugucgggua gcugaccaca ac            42

<210> SEQ ID NO 186
<211> LENGTH: 44
<212> TYPE: RNA
<213> ORGANISM: Artificial Sequence
<220> FEATURE:
<223> OTHER INFORMATION: Synthetic primer

<400> SEQUENCE: 186
uaccuucccu gguacagaau acuggaaggg accaugucuu auga          44

<210> SEQ ID NO 187
<211> LENGTH: 665
<212> TYPE: DNA
<213> ORGANISM: Homo sapiens

<400> SEQUENCE: 187
agtccacagc tgtcactaat cggggtaagc cttgttgtat tgtgcgtgt gggtggcatt    60 ctcaatgaga actagcttca cttgtcattt gagtgaaatc tacaacccga ggcggctagt   120
gctcccgcac tactgggatc tgagatcttc ggagatgact gtcgcccgca gtacggagcc   180
agcagaagtc cgaccettcc tgggaatggg ctgtaccgag aggtccgact agccccaggg   240
ttttagtgag ggggcagtgg aactcagcga gggactgaga gcttcacagc atgcacgagt   300
ttgatgccag agaaaaagtc gggagataaa ggagccgcgt gtcactaaat tgccgtcgca   360
gccgcagcca ctcaagtgcc ggacttgtga gtactctgcg tctccagtcc tcggacagaa   420
gttggagaac tctcttggag aactccccga gttaggagac gagatctcct aacaattact   480
actttttctt gcgctcccca cttgccgctc gctgggacaa acgacagcca cagttcccct   540
gacgacagga tggaggccaa gggcaggagc tgaccagcgc cgcccteccc cgccccgac    600 ccaggaggtg gagatccctc cggtccagcc acattcaaca cccactttct cctccctctg   660
cccct                                                               665

<210> SEQ ID NO 188
<211> LENGTH: 701
<212> TYPE: DNA
<213> ORGANISM: Homo sapiens

<400> SEQUENCE: 188
tattctgtgt gataataaag aataaactaa tttctatatc tctcttttatt aatgaattat   60 agcatctaaa acctcaatac aattacatac aagcacacac ctaatcatca gtagtacatt   120
ctttaccagt catttaaaat ttataaccaa catttcaatt tgtacaatac tgtatgtggc   180
```

```
ataaggtgag atatttatat ggaagatttg gcattataga gaaaatatcc ttgactgggt    240
atgcatttta gcaaagcaaa gagtgattct caggcaatca agttgaaacc aactacacag    300
tgtttcaatc agaaagacaa aatacaatca actgacatct agtgagattc aataatatac    360
tgttttggct attcacattg attaaaaagt ttggtattat acaagaattt tcatatgaaa    420
tttaatgcat ttcacattaa ggtgaatgat attctacttg taataacaaa gtatttcaga    480
ctacattggt ttcattacta ggaatataat ttagtatagc tctagaaata tacaaatatg    540
ctcctttagt aaataaaata aatgcctaaa ttctataagg aactgatgca ggcaaaccct    600
aaaatggggg ctcagcttgg gaggattttt ggcttaattc agaaaagaat tcaagaggga    660
acccacagtg aaagaagcca agtttattgg agcaacagca t                       701

<210> SEQ ID NO 189
<211> LENGTH: 701
<212> TYPE: DNA
<213> ORGANISM: Homo sapiens

<400> SEQUENCE: 189
atgctgttgc tccaataaac ttggcttctt tcactgtggg ttccctcttg aattcttttc     60
tgaattaagc caaaaatcct cccaagctga gcccccattt tagggtttgc ctgcatcagt    120
tccttataga atttaggcat ttatttatt tactaaagga gcatatttgt atatttctag    180
agctatacta aattatattc ctagtaatga accaatgta gtctgaaata ctttgttatt    240
acaagtagaa tatcattcac cttaatgtga aatgcattaa atttcatatg aaaattcttg    300
tataatacca aacttttttaa tcaatgtgaa tagccaaaac agtatattat tgaatctcac    360
tagatgtcag ttgattgtat tttgtctttc tgattgaaac actgtgtagt tggtttcaac    420
ttgattgcct gagaatcact ctttgctttg ctaaaatgca tacccagtca aggatatttt    480
ctctataatg ccaaatcttc catataaata tctcacctta tgccacatac agtattgtac    540
aaattgaaat gttggttata aattttaaat gactggtaaa gaatgtacta ctgatgatta    600
gtgtgtgtct tgtatgtaat tgtattgagg ttttagatgc tataattcat taataaagag    660
agatatagaa attagtttat tctttattat cacacagaat a                       701

<210> SEQ ID NO 190
<211> LENGTH: 1304
<212> TYPE: DNA
<213> ORGANISM: Homo sapiens

<400> SEQUENCE: 190
tatagctctc tctacactaa tcatgaataa atacttaata tcaaagatca agtttttaa      60 agctatattt taatggcagg aggttgtatt tacctaatca gatgaagttt aatcccatct    120
tataaatgat tgaatccaaa caagtagaat aactataata tgcagagatc catgaccagt    180
tatttgtgag caatttggaa ttcataaagc ttaaacaact taggtactct atgaaaaagc    240
aaagtatttt tatgtctgaa ttatgtcagc tacccgtaat tatgctgtga tataagaaag    300
cagtatagta agaatatatg ctctggagct acaccttctc aatctcattt caggctgtac    360
cacttgctaa ctatgtgacc ttgcaacata ctttcactct ctgccttagt tttcttatct    420
gtaaaatgga tataacaata gtacttgttt cataggggttg ttataaggat gaaatcagta    480
taagaaaaat aaacttagag cagtgtgtga catagcaagc actatttggg tgtttcatcc    540
aaattaagtg gctttttcct taatacataa atgattaaag gtacaaaaga tattaaactt    600 ttttttttt ttttgagat ggagtcttgc tctgtcaccc aggctggagt gcagtggcac    660
```

```
gatttcggct cactgcaacc tccacttccc gggctcaagc gattctcttg cctcagcctc    720
ccaagtagct gggactacag gtgtacacca ccaggcccag ctaattttg tattttagt      780 agagacaggg tttcaccatg ttggccagga tggtctcaat ctcctgacct tgtgatctgc    840
ctgccttggc ctcccaaagt tctgggatta caggtgtgaa ccactgcacc tggcctaaac    900
ttttatatta tataaactag taaaaataat ttttaatatt ttaggtcatg ggaaattcag    960
cagcatagta attatcaaag tagtaaattt tttcagcaaa ggaggtcaag gatagactgt    1020
tacaagtgaa aaaatagga tattaatcaa caaaattctc aatctgaata gccacaattt     1080
ttcagtttct gtacctgaaa tagtttctgc atgggacaga ttggactaac caaatttatc    1140
tcatttttat gactctagcc taactaccct ccccattaaa taatgttttt aagtatatac    1200
aaagggaaaa aaacaacttt ttgaattatg agatatactg aataaaacaa taatgaaaaa    1260
gctatttata aaatagttaa gattagatta taaatctaaa gttg                    1304
```

<210> SEQ ID NO 191
<211> LENGTH: 1304
<212> TYPE: DNA
<213> ORGANISM: Homo sapiens

<400> SEQUENCE: 191

```
caactttaga tttataatct aatcttaact attttataaa tagcttttc attattgttt     60 tattcagtat atctcataat tcaaaaagtt gttttttcc ctttgtatat acttaaaaac     120
attatttaat ggggagggta gttaggctag agtcataaaa atgagataaa tttggttagt    180
ccaatctgtc ccatgcagaa actatttcag gtacagaaac tgaaaaattg tggctattca    240
gattgagaat tttgttgatt aatatcctat tttttcact tgtaacagtc tatccttgac     300
ctcctttgct gaaaaaattt actactttga taattactat gctgctgaat ttcccatgac    360
ctaaaatatt aaaaattatt tttactagtt tatataatat aaaagtttag gccaggtgca    420
gtggttcaca cctgtaatcc cagaactttg ggaggccaag gcaggcagat cacaaggtca    480
ggagattgag accatcctgg ccaacatggt gaaaccctgt ctctactaaa aatacaaaaa    540
ttagctgggc ctggtggtgt acacctgtag tcccagctac ttgggaggct gaggcaagag    600
aatcgcttga gcccgggaag tggaggttgc agtgagccga atcgtgcca ctgcactcca     660 gcctgggtga cagagcaaga ctccatctca aaaaaaaaa aaaaagttt aatatctttt      720 gtaccttta tcatttatgt attaaggaaa aagccactta atttggatga acaccaaaa      780 tagtgcttgc tatgtcacac actgctctaa gttatttttt cttatactga tttcatcctt    840
ataacaaccc tatgaaacaa gtactattgt tatatccatt ttacagataa gaaaactaag    900
gcagagagtg aaagtatgtt gcaaggtcac atagttagca agtggtacag cctgaaatga    960
gattgagaag gtgtagctcc agagcatata ttcttactat actgctttct tatatcacag    1020
cataattacg ggtagctgac ataattcaga cataaaaata ctttgctttt tcatagagta    1080
cctaagttgt ttaagcttta tgaattccaa attgctcaca ataactggt catggatctc      1140 tgcatattat agttattcta cttgtttgga ttcaatcatt tataagatgg gattaaactt     1200
catctgatta ggtaaataca acctcctgcc attaaaatat agctttaaaa aacttgatct    1260
ttgatattaa gtatttattc atgattagtg tagagagagc tata                    1304
```

<210> SEQ ID NO 192
<211> LENGTH: 58
<212> TYPE: DNA
<213> ORGANISM: Artificial Sequence

```
<220> FEATURE:
<223> OTHER INFORMATION: Synthetic primer
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t

<400> SEQUENCE: 192
taaggaactg atgcaggcaa acnctaaaat gggggctcag nntgggagga tttttggc        58

<210> SEQ ID NO 193
<211> LENGTH: 87
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 193
gactacnttg gtttcnttac taggaatata atttagtata gctctagaaa tatacaaata       60
tgctccttta gtaaataaaa taaatgc                                          87

<210> SEQ ID NO 194
<211> LENGTH: 103
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t

<400> SEQUENCE: 194
cctagaggag gaggcgttgt tagaangctg tctggccagt ccacagctgt cactaatcgg       60
gnnaagcctt gttgtatttg tgngtgtggg tggcattctc aat                       103

<210> SEQ ID NO 195

<400> SEQUENCE: 195

000

<210> SEQ ID NO 196
<211> LENGTH: 101
<212> TYPE: DNA
<213> ORGANISM: Artificial Sequence
<220> FEATURE:
<223> OTHER INFORMATION: Synthetic primer
```

-continued

```
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t

<400> SEQUENCE: 196
tagaggagga ggcgttgtta nnaagctgtc tggccagtcc acagctgtca ctnntcgggg      60
taagccttgt tgtatttgtg cgtgtgngtg gcattctcaa t                        101

<210> SEQ ID NO 197
<211> LENGTH: 103
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (77)..(80)
<223> OTHER INFORMATION: n is a, c, g, or t

<400> SEQUENCE: 197
attgagaatg ccanncacac gcacaaatac aacaaggctt accccgatta gtgacagctg      60
tggactggcc agacagnnnn ctaacaacgc ctcctcctct agg                      103

<210> SEQ ID NO 198
<211> LENGTH: 100
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t

<400> SEQUENCE: 198
cctagaggag gaggcnttgt tagaaagctg tctggccagn ccacagctgt cactaatcgg      60
ngtaagcctt gttgtanttg tgcgtgtggg tggcattctc                          100

<210> SEQ ID NO 199
<211> LENGTH: 59
<212> TYPE: DNA
<213> ORGANISM: Artificial Sequence
<220> FEATURE:
<223> OTHER INFORMATION: Synthetic primer
```

```
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 199
agcnnaaaat cctcccaagc tgagccccca ttttagggnt tgcctgcatc agttcctta      59

<210> SEQ ID NO 200
<211> LENGTH: 56
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 200
ggaactgatg caggcaaacc ctaaaatggg cgctcagctt gnnaggattn ttggct         56

<210> SEQ ID NO 201
<211> LENGTH: 32
<212> TYPE: DNA
<213> ORGANISM: Artificial Sequence
<220> FEATURE:
<223> OTHER INFORMATION: Synthetic primer

<400> SEQUENCE: 201
ggtttctttc tccaggtcct cactggccat ac                                  32

<210> SEQ ID NO 202
<211> LENGTH: 43
<212> TYPE: DNA
<213> ORGANISM: Artificial Sequence
<220> FEATURE:
<223> OTHER INFORMATION: Synthetic primer

<400> SEQUENCE: 202
ggatccggga gagctatact cttagtttgt tatagtgact cca                      43
```

US 8,815,586 B2

MODULATION OF GENE EXPRESSION USING OLIGOMERS THAT TARGET GENE REGIONS DOWNSTREAM OF 3' UNTRANSLATED REGIONS

This application claims benefit of priority to U.S. Provisional Application Ser. No. 61/172,528, filed Apr. 24, 2009, and 61/227,952, filed Jul. 23, 2009, the entire contents of both applications hereby being specifically incorporated by reference.

This work was made with government support under grants NIH GM 77253 and NIH NIBIB EB05556 from the National Institutes of Health. The government has certain rights in this invention.

FIELD OF THE INVENTION

The invention relates to method of modulating gene expression using oligomers complementary to gene regions downstream of 3' untranslated regions (3'UTRs) of target genes.

BACKGROUND ART

Modulation of gene expression in mammalian cells by small duplex RNAs is typically associated with recognition of mRNA (Siomi and Siomi, 2009). Duplex RNAs complementary to gene promoters have been reported to either silence or activate gene expression in mammalian cells (Morris et al., 2004; Ting et al., 2005; Janowski et al., 2005; Li et al., 2006; janowski et al., 2007). Argonaute 2 (AGO2), a key protein involved in RNAi (Liu et al., 2004), is required for the action of promoter-targeted RNAs5,8, and a related protein, AGO1, has also been implicated in the mechanism (Kim et al., 2006). Recent reports have suggested that the mechanism of promoter-targeted RNAs involves recognition of noncoding transcripts that overlap gene promoters (Han et al., 2007; Schwartz et al., 2008). Over 70% of all genes have noncoding transcripts that overlap their promoters and these transcripts provide potential target sites for small RNA duplexes (He et al., 2008; Kapranov et al., 2007; Sun et al., 2005; Gingeras, 2007; Wahlstedt, 2006; Amaral and Mattick 2008)).

Promoter-targeted RNAs are robust modulators of progesterone receptor (PR) transcription in T47D and MCF7 breast cancer cells (Janowski et al., 2005; Janowski et al., 2007; Janowski et al., 2006; Schwartz et al., 2008). The inventors term these small RNAs antigene RNAs (agRNAs) to distinguish them from duplex RNAs that target mRNA. The main difference between activation or inhibition of gene expression by closely related agRNAs is the basal expression of PR. Gene silencing is observed in T47D cells that constitutively express PR at high basal levels, while activation of PR expression is observed in MCF7 cells that express PR at low levels (Janowski et al., 2007).

Both activating and inhibitory agRNAs modulate PR expression through binding to complementary target sequences within an antisense transcript that originates from inside the PR gene and is transcribed through the promoter region. agRNAs recruit AGO protein to the antisense transcript, affect levels of RNA polymerase II (RNAP2) at the promoter, and alter the mix of regulatory proteins that bind the antisense transcript and the PR promoter (Schwartz et al., 2008).

Noncoding RNAs also overlap the 3'-untranslated region (3'-UTR) of many genes (Gingeras, 2007; wahlstedt, 2006; Amaral and Mattick, 2008). The 3'-UTR plays a major role in cellular regulation and disease pathology (Chen et al., 2006) and is involved in a variety of post-transcriptional processes, including mRNA transport, localization, and stability. The function of 3' noncoding transcripts is unclear, but their proximity to the 3'-UTR suggests that they may affect gene regulation.

The abundance of transcripts that overlap the 3'-UTR, coupled with the ability of agRNAs to modulate gene expression by targeting overlapping 5' transcripts, suggested that small RNAs might also influence gene expression by recognizing sequences beyond the 3' end of genes. However, there has been little investigation into the potential function of overlapping noncoding transcripts at the 3'-region of genes, and no examination of whether these noncoding transcripts might be targets for modulating gene expression by duplex RNAs.

SUMMARY OF THE INVENTION

Thus, in accordance with the present invention, there is provided a method of modulating expression of a target gene in a cell comprising contacting the cell with an oligomer complementary to a region downstream of a 3'-UTR of the target gene, thereby modulating expression of the target gene. The region beyond or downstream of the '3-UTR region is defined as any region 3' to the 3'-terminus of the normal, protein-encoding transcript for the target gene. This region may be non-coding, or it may overlap part of a unrelated (not the target gene) transcript. The oligomer may be a duplex, such as duplex RNA. The oligomer may also single-stranded. The oligomer may comprise at least one peptide nucleic acid (PNA) base, locked nucleic acid (LNA) base or 2'-O-methyl (2'-O-me) 2'-deoxy, 2'-deoxy-2'-fluoro, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA) base.

The oligomer may be 90%, 95% or 100% complementary to the region downstream of the 3'-UTR. The oligomer may be 10-30 bases in length, 15-25 bases in length, or 18-23 bases in length. The target gene may be the progesterone receptor, BRCA-1, liver X receptor or the androgen receptor. The oligomer may target, i.e., be complementary to or mimic, an miRNA seed region in the region downstream of the 3'-UTR. The cell may be an isolated cell. The cell may also be located in situ in a host, and contacting comprises administering to the host an amount of the oligomer effective to modulate expression of the target gene. The expression of the target gene may be increased or decreased.

The method may further comprise detecting a change in the expression of the target gene, such as by inferring a change in the expression of the target gene from a physiologic change in the cell, or where the cell is located in situ in a host, by inferring a change in the expression of the target gene from a physiologic change in the host. Detecting may comprise one or more of Northern blot, PCR, immunohistochemistry, Western blot or ELISA. The change in expression may be due to a change in transcription.

The method of claim 1, wherein said region may lie between 1 to 10,000 bases 3' to the end of the 3'-UTR of the target gene, between 1 and 5000 bases 3' to the end of the 3'-UTR of the target gene, between 1 and 2500 bases 3' to the end of the 3'-UTR of the target gene, or between 1 and 1000 bases 3' to the end of the 3'-UTR of the target gene.

Also provided is a method of recruiting argonaute (AGO) to a region downstream of 3'-UTR of a target gene in a cell comprising contacting the cell with an oligomer complementary to a region downstream of a 3'-UTR of the target gene, thereby recruiting AGO to the region downstream of the 3'-UTR of the target gene. The AGO may be AGO1, AGO2, AGO3 or AGO4. The 3'-UTR may be in physical proximity of a promoter region for the target gene, thereby further recruiting AGO to the promoter region of the target gene.

The invention provides compositions such as reagents and formulations tailored to the subject methods.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIGS. 1A-F. Characterization of PR mRNA. (FIG. 1A) Differing annotations of PR mRNA. Top: pre-2008 GenBank (NM_000926.3); Middle: Predicted largest transcript based on Northern analysis in published reports; Bottom: Current GenBank (NM_000926.4). (FIG. 1B) Schematic of PR mRNA predicted by GenBank and locations of probes for Northern analysis. (FIG. 1C) Northern analysis of PR mRNA comparing results using probes that detect PR mRNA (probe 1) or targeting the 3' termini of PR mRNA (probe 2), (FIG. 1D) Northern analysis of PR mRNA using probe 2 or a probe immediately downstream of the potential mRNA terminus (probe 3). (FIG. 1E) qPCR showing levels of poly-A RNA in T47D cells detected from the PR transcription start site (+1) past the most downstream annotated terminus of PR mRNA. Notation indicates target region for PCR primers. Data is the resultant of triplicate independent experiments. (FIG. 1F) Location of target sequences for duplex RNAs relative to PR mRNA. The 5' and 3' noncoding transcripts that overlap the transcription start site and polyadenylation site are shown.

FIGS. 2A-E. Characterization of the PR 3' noncoding transcript. (FIG. 2A) Location of RACE (A, B, C, and D) or RT-PCR (E, F, G, and H) primers relative to PR mRNA and the 3' noncoding transcript. (FIG. 2B) Agarose gel analysis of RACE products. Total RNA used in RACE was treated with DNase prior to reverse transcription. (FIG. 2C) Agarose gel analysis of RT-PCR amplification using primers E, F, G, and H as shown. Poly(A) RNA was DNase-treated prior to reverse transcription. Amplification of genomic DNA was included as a positive control for primer function. Complete data including sequencing of amplified products is shown in FIG. 12. qPCR of relative RNA levels in (FIG. 2D) T47D cells and (FIG. 2E) MCF7 cells using primer sets upstream or downstream of the predicted +14,546 termini of the 3' noncoding transcript (FIG. 10). −RT: RNA samples that were not treated with reverse transcriptase (−RT) were used as negative control. +RT: Reverse transcriptase added. Data is the result of triplicate independent experiments.

FIGS. 3A-E. Inhibition of PR expression in T47D cells by agRNAs complementary to sequences downstream from the terminus of PR mRNA. (FIG. 3A) Western analysis showing inhibition of protein expression by duplex RNAs (50 nM). (FIG. 3B) Dose response for PR13580. (FIG. 3C) qPCR showing reduction of PR mRNA levels by duplex RNAs (25 nM). Four different primer sets were used, each complementary to different regions of the PR gene (Supplementary Table 4). (FIG. 3D) Presence of RNAP2 at the PR transcription start site (25 nM duplex RNA) evaluated by ChIP. (FIG. 3E) Chromatin immunoprecipitation for the H3K27 trimethylation (H3K27me3) marker within the PR gene locus in T47D cells. *$p<0.005$, $p<0.01$, and *$p<0.05$ as compared to cells treated with a mismatch RNA. p-values were calculated using the two-tailed unpaired Student's T-test with equal variances. All error bars represent standard deviation. Data in FIGS. 3A, 3C and 3D are the result of triplicate independent experiments. Data in FIG. 3B are representative of duplicate experiments.

FIGS. 4A-F. Enhanced PR expression in MCF7 cells by an RNA complementary to a sequence downstream from the terminus of the PR 3'-UTR. (FIG. 4A) Western analysis showing activation of protein expression by duplex RNAs. (FIG. 4B) Dose response for RNA PR13515. (FIG. 4C) qPCR showing effect on RNA levels. Four different primer sets were used, each complementary to different regions near the PR gene. (FIG. 4D) Recruitment of RNAP2 to the PR promoter upon addition of PR13515 or PR-11 evaluated by ChIP. (FIG. 4E) Chromatin immunoprecipitation for the H3K27 trimethylation (H3K27me3) marker within the PR gene locus in MCF7 cells. (FIG. 4F) MCF7 cells were transfected with either PR-11 or PR13515. After two days, actinomycin D (act D, 1 μg/ml) or vehicle was added to the media. Cells were harvested at the indicated timepoints (hours) after actinomycin D or vehicle treatment. Data were normalized to levels of 18S rRNA that did not significantly change for the duration of the experiment. Standard deviation was calculated from 4-6 samples per treatment group. *$p<0.005$, $p<0.01$, and *$p<0.05$ as compared to cells treated with RNA MM. p-values were calculated using the two-tailed unpaired Student's T-test with equal variances. All error bars represent standard deviation. Duplex RNAs were added to cells at 25 nM unless otherwise noted. Data in FIGS. 4A-D are the result of triplicate experiments. Data in FIG. 4F are the result of 4-6 independent experiments.

FIG. 5A-D. Effect of physiologic stimuli or effect of combining physiologic stimuli with addition of agRNAs on expression of PR mRNA, the 3' noncoding RNA, and the 5' noncoding RNA. qPCR analysis showing the effect of physiologic stimuli on transcript expression in (FIG. 5A) T47D cells and (FIG. 5B) MCF7 cells. For the sample labeled "serum stripped followed by full media" cells were grown in serum stripped media. The media was replaced by full media for one day prior to harvesting. qPCR analysis of the effect of physiologic stimuli and agRNA (25 nM) addition on transcript expression in (FIG. 5C) T47D cells and (FIG. 5D) MCF7 cells. PR 3'NCR: 3' noncoding PR RNA. PR 5'NCR: 5' noncoding PR RNA. SS: Serum-stripped media. FM: full media. E2: 17β estradiol treatment (100 nM). IL1β: interleukin 1β treatment (10 ng/mL). EGF: epidermal growth factor treatment (100 ng/mL). Results are from 3-6 independent replicates.

FIGS. 6A-H. Effect of 3' or 5' agRNAs on recruitment of AGO2 protein to the 3' or 5' noncoding transcripts at the PR locus. RNA immunoprecipitation (RIP) of 3' noncoding RNA using an anti-AGO2 antibody after treatment with (FIG. 6A) inhibitory RNA PR13580 in T47D cells or (FIG. 6B) activating RNA PR13515 in MCF7 cells on recruitment of AGO2 protein to the 3' noncoding transcript. Effect of adding (FIG. 6C) inhibitory RNA PR-9 to T47D cells or (FIG. 6D) activating RNA PR-11 to MCF7 cells on recruitment of AGO2 protein to the 5' noncoding transcript. Effect of adding (FIG. 6E) inhibitory RNA PR13580 to T47D cells or (FIG. 6F) activating RNA PR13515 to MCF7 cells on co-immunoprecipitation of AGO2 protein with the 5' noncoding transcript. Effect of adding (FIG. 6G) inhibitory RNA PR-9 to T47D cells or (FIG. 6H) activating RNA PR-11 to MCF7 cells on co-immunoprecipitation of AGO2 protein with the 3' noncoding transcript. The scheme above each gel depicts PR mRNA, the 3' and/or 5' noncoding transcripts, and AGO2 bound agRNA. The heaviest line represents the transcript being amplified. Duplex RNAs were added to cells at 25 nM. Experiments are representative of two independent determinations.

FIGS. 7A-E. 3C analysis of the PR locus. (FIG. 7A) Schematic of the PR gene showing DpnII cleavage sites, exon boundaries, and locations of primers used for 3C analysis. The primer pairs used for 3C amplification are shown on the x axes of parts (FIG. 7B) and (FIG. 7D). (FIG. 7B) Top, qPCR showing the relative levels of detection of crosslinked product after treatment with a mismatch-containing RNA duplex or inhibitory duplexes PR-9 or PR13580. (FIG. 7C) qPCR showing reduced RNA levels in samples used for part (FIG. 7C). (FIG. 7D) Top, qPCR showing the relative levels of crosslinked product after treatment with a mismatch-containing RNA duplex or activating duplexes PR-11 or PR13515. (FIG. 7E) qPCR showing increased RNA levels in the samples used for part (FIG. 7D). Primer P amplifies a sequence at the PR promoter. Primers E1, E2, E3, and E4 amplify sequences within PR exons 1-4. Primers T1 and T2 amplify sequences beyond the terminus of PR mRNA. F1/F2=Fixed fragment. The fixed fragment is a normalization control derived from genomic DNA by primers complementary to sequences within exon 135. The bar represents performance of the normalization control, not its absolute value. Values in parts (FIG. 7D) and (FIG. 7?) are relative to amplification of sequence at the PR promoter using primer P. Duplex RNAs were added to cells at 25 nM. Two bands are observed in the T2/F2 analysis because of an alternative DpnII cleavage site. The positive control shows amplification of a synthetic DNA. Data are from three independent experiments.

FIGS. 8A-G. Inhibition of PR expression by a miRNA complementary to the PR 3' noncoding RNA. (FIG. 8A) Sequences for five computational matches between miRNAs and the region of PR 3' noncoding RNA beyond +13,037 (Supplementary FIG. S27) (SEQ ID NOS:164-168). Potential seed sequence matches (bases 2-8) are in boldface and underlined. (FIG. 8B) qPCR using four different primer sets showing the effects of adding miRNA mimics on PR expression. (FIG. 8C) Western analysis showing the effects of adding miRNA mimics on PR protein expression. (FIG. 8D) Dose response analysis showing effects of inhibitory miRNA miR-193b. (FIG. 8E) Western analysis showing inhibition of PR expression by MiR-193b and mismatch-containing analogs. (FIG. 8F) qPCR comparing the effects of inhibitor agRNA PR13580 or miR-193b on levels of the 5' noncoding transcript, PR mRNA, PR pre-mRNA, and the 3' noncoding transcript. (FIG. 8G) ChIP showing the effect of addition of miR-193b or inhibitory agRNA PR13580 on the presence of RNAP2 at the PR promoter. Experiments were performed in T47D cells. *$p<0.005$, $p<0.01$, and *$p<0.05$ as compared to cells treated with RNA MM. p-values were calculated using the two-tailed unpaired Student's T-test with equal variances. All error bars represent standard deviation. Duplex RNAs were added at 25 nM unless otherwise noted. Data are from triplicate independent experiments.

FIGS. 9A-B. Model for modulation of transcription by 3'-agRNAs. (FIG. 9A) 100,000 bases separates the genomic locations of the promoter and 3' terminal regions of the PR gene. (FIG. 9B). Gene looping juxtaposes the 5' promoter and 3' terminator, bringing DNA sequences into close proximity. Addition of the 3' agRNA recruits AGO2 to the 3' noncoding transcript. The arrival of AGO2 may affect other proteins (here shown as unlabeled circles) at the gene promoter and alter regulation of transcription. The proximity of 3' and 5' noncoding transcripts allows them to co-immunoprecipitate during RIP with anti-AGO antibodies.

FIGS. 10A-B. Measurement of poly-A RNA levels. Poly A RNA levels were measured in (FIG. 10A) T47D and (FIG. 10B) MCF7 cells using multiple primer sets that recognize regions before the 3' terminus (+13,037) of PR mRNA, after the 3' end of PR mRNA, and downstream from the 3' terminus of the 3' noncoding transcript (FIGS. 1E-F). qPCR demonstrates that levels of poly-A RNA drop sharply past the 3' end of PR mRNA. RNA levels then drop sharply again for primers complementary to targets past the 3' end of noncoding RNA. Primer set Exon4/5 targets the boundary of exon 4 and 5 in PR mRNA. Primer set Exon6/7 targets the boundary of exon 6 and 7 in PR mRNA.

FIGS. 11A-E. Characterization of a noncoding transcript that overlap the 3'-termini of PR mRNA. The RACE assay was used to detect the transcription start site and polyadenylation sites of 3' noncoding transcripts. The inventors used primers recognizing sequences close to the complementary sequences of 3' inhibitory and activating agRNAs. RACE products were analyzed on a 2% agarose gel and sequenced. (FIG. 11A) Location of primers (A, B, C, and D) relative to PR mRNA. Data is the representative of triplicate independent determinations. (FIG. 11B) Agarose gel analysis of RACE products. For 5' RACE use of primer A (5'-CACTGT-GTAGTTGGTTTCAACTTGATTGCCTGA-3' (SEQ ID NO:154)) and nested primer B (5'-TGATTGCCTGAGAAT-CACTCTTTGCTTTGCTA-3' (SEQ ID NO:155)) detects a transcription start site 11325 nucleotides downstream from the PR mRNA+1 start site. For 3' RACE use of primer C (5'-GCAAAGCAAAGAGTGATTCTCAGGCAATCAAG-3' (SEQ ID NO:156)) and nested primer D (5'-GCCTAAAT-TCTATAAGGAACTGATGCAGGCAAACC-3' (SEQ ID NO:157)) detects multiple polyadenylationsites 1400-1500 nucleotides downstream from the 3' end of PR mRNA. RACE experiments did not detect antisense transcripts. Total RNA used in RACE was treated with DNase prior to reverse transcription. +RT: Reverse transcriptase added. −RT: No reverse transcriptase added. The results from sequencing RACE products are shown in FIG. 11E (SEQ ID NO:169). (FIG. 11C) Locations of primers for RT-PCR. (FIG. 11D) RT-PCR with primer F (5'-CCATTTCTTGCTGGCTTAGCACATTC-CTCA-3' (SEQ ID NO:158)) and primer G (5'-CAGTGA-CATATAGTGACACAAGGGAAAAGTCTCA-3' (SEQ ID NO:159)) on poly(A) RNA from T47D cells revealed an unspliced transcript from +11325 transcription start site to +14546 polyadenylation site detected by RACE in FIG. 11A.

No transcript was detected from primers E to G or from primers F to H, even though these primer sets could amplify genomic DNA efficiently. Primer E (5'-AGGGAGCACTG-GTGAGCAGTAGGTTGAAGA-3' (SEQ ID NO:160)) recognizes sequences 200 nt upstream of +11325 transcription start site. Primer H (5'-TCCAAATTGCTCA-CAAATAACTGGTCATGGA-3' (SEQ ID NO:161)) recognizes sequences 150 nt downstream from +14546 polyadenylation site. Poly(A) RNA was DNase-treated prior to reverse transcription. +RT: Reverse transcriptase added. −RT: No reverse transcriptase added. (FIG. 11E) (SEQ ID NO:169) Sequence of the noncoding transcript that overlaps the 3' end of PR mRNA was deduced on the basis of sequencing results from FIGS. 11A and 11B (SEQ ID NO:170).

FIGS. 13A-H. bDNA assay of transcript levels at the PR locus. Transcript levels in (FIG. 13A) T47D cells and (FIG. 13B) MCF7 cells measured by using bDNA prove sets complementary to the 3'+11325/+14546 noncoding transcript (sense orientation and antisense orientation) or complementary to the region beyond the +11325/+145463' 3' noncoding transcript (sense orientation and antisense orientation). (FIG. 13C) (next page) Schematic of target locations for bDNA probe sets (SEQ ID NOS:170 and 171). (FIGS. 13D-H) (next pages) Probe sets for bDNA assay. CE: Capture extender. LE: Label extender. BL: Blockers. Data is an average of four experiments (SEQ ID NOS:187 to 191).

FIGS. 14A-B. Data for IC50 values for siRNA PR2526 and 3' agRNA PR13580. Western analysis of protein levels. (FIG. 14A) Inhibition of PR expression upon addition of increasing concentrations of PR2526, a duplex RNA complementary to PR mRNA (the gel is representative of three replicates). (FIG. 14B) Inhibition of PR expression upon addition of increasing concentrations of 3' agRNA PR13580 (the gel is representative of two replicates). Data was quantified and used to calculate IC50 values. Data from the dose response experiments was fit to the following model equation, y=100*xm/(nm+xm), where y is percent inhibition of PR and x is concentration of RNA duplex. m and n are fitting parameters, where n is taken as the $IC_{50}$ value.

FIGS. 15A-F. PR or BRCA1 gene expression is not altered through the interferon response. All data are from transfections of T47D or MCF7 breast cancer cells. (FIG. 15A) qPCR measurement of mRNA levels of various interferon-responsive genes in T47D cells upon addition of poly (I:C) RNA or duplex RNAs after a 72-hour incubation with transfected nucleic acid. (FIG. 15B) qPCR measurement of PR mRNA levels 72 hours after addition of poly (I:C) RNA. (FIG. 15C) qPCR measurement of mRNA levels of various interferon responsive genes in MCF7 cells upon addition of poly (I:C) RNA or duplex RNAs after a 72-hour incubation with transfected nucleic acid. (FIG. 15D) qPCR measurement of PR mRNA levels in MCF7 cells upon addition of poly (I:C) RNA for 72 hours. (FIG. 15E) qPCR measurement of mRNA levels of various interferon-responsive genes in T47D cells upon addition of poly (I:C) RNA or duplex RNAs after a 72-hour incubation with transfected nucleic acid. (FIG. 15F) qPCR measurement of BRCA1 in T47D cells upon addition of poly (I:C) RNA for 72 hours. Triplicate independent experiments.

FIGS. 16A-B. Measurement of transcript levels at the PR locus in T47D or MCF7 cells upon treatment with inactive RNA PR13063, inhibitory 3' agRNA PR13580, or activating 3' agRNA PR13515. PR13063 is a duplex RNA that does not modulate PR expression when tested in MCF7 or T47D cells (FIGS. 2 and 3). PR13580 inhibits PR expression in T47D cells (FIG. 2) and PR13515 activates PR expression in MCF7 cells (FIG. 3). qPCR showing levels of transcripts are unaffected by inactive 3' agRNA PR13063 in (FIG. 16A) T47D cells and (FIG. 16B) MCF7 cells. T47D cells were transfected at 50 nM. MCF7 cells were transfected at 25 nM. All error bars are standard deviation. p-values were calculated using the two tailed unpaired Student's T-test with equal variances. *$p<0.005$, $p<0.01$, *$p<0.05$ as compared to cells treated with duplex RNA MM (mismatch control). Data is from triplicate independent experiments.

FIGS. 17A-D. Effect of agRNAs on transcript levels measured by the bDNA assay. bDNA assay showing effects of adding inhibitory agRNAs PR-9 or PR13580 on levels of (FIG. 17A) PR mRNA or the 3' noncoding transcript in T47D cells. (FIG. 17B) qPCR performed in parallel showing effects of adding inhibitory agRNAs PR-9 or PR13580 on levels of PR mRNA in T47D cells. (FIG. 17C) bDNA assay showing effects of adding activating agRNAs PR-11 or PR13515 on levels of PR mRNA or the 3' noncoding transcript in MCF7 cells. (FIG. 17D) qPCR performed in parallel showing effects of adding activating agRNAs PR-11 or PR13515 on levels of PR mRNA in T47D cell. agRNAs were transfected at 25 nM. All error bars are standard deviation. p-values were calculated using two way ANOVA (Graphpad Prism 4 software). *$p<0.005$, $p<0.01$, *$p<0.05$ as compared to cells treated with duplex RNA MM. Data is an average of four experiments.

FIGS. 19A-H. Characterization of RIP products. Sequences of the amplified products from Q-PCR after RIP using anti-AGO2 antibody from T47D or MCF7 cells treated with inhibitory or activating agRNAs. FIGS. 19A-H correspond to FIGS. 6A-H (SEQ ID NOS:192, 193, 194, 196, 197, 198, 199,200).

FIGS. 20A-D. RIP examining the association of Ago1 with PR 3' noncoding transcripts in nuclear lysates from T47D or MCF cells. Association of AGO1 with (FIG. 20A) PR 3' noncoding transcript or (FIG. 20B) 5' noncoding transcript after addition of PR13515 MCF7 cells. Association of AGO1 with (FIG. 20C) PR 3' noncoding transcript or (FIG. 20D) 5' PR noncoding transcript after addition of PR13580 to T47D cells. MM: negative control RNA duplex. IgG: negative control antibody. −RT: no reverse transcriptase added.

(FIG. 23B) T47D cells. "Input" samples are the crude samples after DNase treatment and prior to immunoprecipitation and are analyzed here. The inventors chose to analyze input samples as a stringent test because the input samples contain much more genomic DNA than the corresponding sample after immunoprecipitation. If DNA can be amplified, the input samples would be much more likely to reveal that fact. The primer set covering PR promoter from −37 to +66 (relative to TSS) was used. The PCR product identities have been confirmed by sequencing. RT: Reverse transcriptase added. No RT: No reverse transcriptase added. The Input sample was 5% of a 100 µL nuclear fraction (~250, 000 cell equivalents). The inventors also examined amplification of samples after immunoprecipitation using anti-AGO2 antibody. Data corresponds with data shown in FIGS. 4A-H. When no reverse transcriptase (−RT) is added, no amplified product is detected. T47D or MCF7 cells were transfected with (FIG. 23C) PR-9, (FIG. 23D) PR13580, (FIG. 23E) PR-11 or (FIG. 23F) PR13515, and immunoprecipitated with anti-Ago2 antibody. The primer set identifying 5' noncoding antisense transcript (5' NCR) or 3' noncoding sense transcript (3' NCR) was used.

(FIG. 24A) Location of primers for 3' and 5' RACE and location of duplex RNAs PR2526, PR13515, and PR13580. (FIG. 24B) Results of 5'-RACE with primer B (5'-TCAACT-CAAACTTACAGCAAGAATCCTGTTCCACTC-3' (SEQ ID NO:162)) downstream from the recognition sites of PR13515 and PR13580 on 3' noncoding sense transcript didn't detect any cleavage site. As a positive control, the cleavage site by PR2526, an siRNA targeting PR mRNA, was detected with the downstream primer A (5'-AGAAACGCT-GTGAGCTCGACACAACTCC-3' (SEQ ID NO:163)).

(FIG. 25A) qPCR analysis showing the effect of the 3' noncoding transcript on PR mRNA and the 5' antisense noncoding transcript. (FIG. 25B) Relative expression levels of PR in MCF7, T47D, and MDA-MB-231 cells. 3'NCR: 3' noncoding RNA. 5'NCR: 5' noncoding RNA. All experiments were done in triplicate except for the T47D and MDA-MB-231 empty vector transfections which were done in duplicate.

FIGS. 27A-H. 3C analysis of MCF7 and T47D cells using primers sets as described in FIG. 7A. 3C analysis for MCF7 (FIG. 27A) or T47D (FIG. 27C) cells upon treatment with full media, serum-stripped media, IL1β (MCF7, 10 ng/mL), or epithelial growth factor (EGF, T47D 100 ng/mL). 3C analysis for MCF7 (E) or T47D (FIG. 27G) cells upon treatment with serum-stripped media or serum-stripped media supplemented with IL1β (MCF7, 10 ng/mL), or epithelial growth factor (EGF, T47D, 100 ng/mL), or estradiol (both T47D or MCF7, 100 nM). FIGS. 27B, 27D, 27F, and 27H show the effects of treatments on PR mRNA levels as monitored by qPCR. FF=Fixed Fragment. As described by Baylin and coworkers, the "Fixed Fragment" is a normalization control derived from genomic DNA by primers complementary to sequences within exon 1. The bar represents performance of the normalization control (a demonstration that genomic DNA can be amplified by primers F1 and F2), not an absolute value. Primer combinations are those shown in FIG. 7A. Data are from 3-4 independent experiments.

FIGS. 28A-C. PCR product was sequenced for some combinations of primers detecting gene loops between the 5' and 3' ends of PR. (FIG. 28A) Product was obtained using four possible combinations of primers between two cut sites at the PR 5' end and one cut site and the PR 3' end. (FIG. 28B) Two PCR products were obtained in T47D cells and correctly aligned with their genomic targets at the 5' and 3' ends of PR. Blue text aligned with the 5' end and red text aligned with the 3' end. The DpnII cut site used is bold and underlined (SEQ ID NOS: 173 and 174). (FIG. 28C) Four PCR products were obtained in MCF7 cells and correctly aligned with their genomic targets at the 5' and 3' ends of PR. Coloring is as in part B (SEQ ID NOS:175-178). Note for F2/T1 the use of a nearby DpnII cut site for ligation. The alternative site is underlined but not bold. The use of alternative cut sites explains additional bands seen by gel electrophoresis of PCR product (see FIGS. 7B and 7D). Alignments were made using BLAT from UCSC genome brower at genome.ucsc.edu.

FIGS. 29A-B. Measurement of poly-A RNA levels in T47D cells using different primer sets surrounding the 3' terminus of BRCA1 mRNA. (FIG. 29A) qPCR showing levels of poly-A RNA detected from the BRCA1 transcription start site past the most downstream annotated terminus of PR BRCA1. (FIG. 29B) 3' RACE using primers upstream and downstream of the termination site for BRCA1 revealed no evidence for a longer BRCA1 messenger RNA transcript. Primers A and B detected the known BRCA1 termination and primers C, D, and E downstream of that site did not detect amplified product. Primer sequences are shown in Supplementary Table S11. The additional faint bands derived from use of primers C could not be amplified in sufficient quantities to enable cloning, sequencing, and identification. They are either nonspecific products or are at too low an abundance to be detected by RACE. Data in FIG. 29A are from triplicate independent experiments.

FIGS. 30A-D. 3C analysis of the BRCA1 gene. (FIG. 30A) Primer sets used as described by Brown and coworkers (Tan-Wong et al., 2008). Primer D3 was a fixed reverse primer. (FIG. 30B) Agarose gel analysis of 3C products in MCF7 cells. In contrast to previous results (Tan-Wong et al., 2008), the inventors observed product when using primer D4 but not with primer D9. (FIG. 30C) 3C analysis for T47D cells. (FIG. 30D) 3C product D11/D3 was cloned and sequenced. The product aligns with sequences at the 5' and 3' termini of the BRCA1 gene (SEQ ID NO:179). Control experiments using non-crosslinked samples produced no PCR product. No Crosslink: no crosslinker added to sample prior to ligation and amplification. Primer sequences are shown in Supplementary Table S12. Data are representative of duplicate independent experiments.

FIGS. 31A-D. Inhibition of BRCA1 expression by agRNAs targeting sequences beyond the 3'-UTR. Western analysis showing levels of BRCA1 protein after addition of (FIG. 31A) six agRNAs complementary to sequences beyond the 3' polyadenylation site for BRCA1 mRNA and siBRCA1 complementary to BRCA1 mRNA. (FIG. 31B) increasing concentrations of BRCA7851. (FIG. 31C) qPCR analysis of RNA levels using primer sets designed to detect noncoding RNA at the BRCA1 promoter, BRCA1 mRNA, BRCA1 pre-mRNA, and noncoding RNA beyond the 3' terminus of BRCA1 mRNA. (FIG. 31D) Presence of RNAP2 at the BRCA1 transcription start site evaluated by ChIP. All error bars are standard deviation. *p<0.005, p<0.01, and *p<0.05 as compared to cells treated with RNA MM. p-values were calculated using the two tailed unpaired Student's T-test with equal variances. All error bars represent standard deviation. Duplex RNAs were added to cells at 25 nM unless otherwise noted. Data are from duplicate or triplicate independent experiments.

FIGS. 32A-B. Location of miRNAs complementary to PR 3' ncRNA. (FIG. 32A) Schematic of miRNA target sites relative to inhibitory agRNA PR13580. (FIG. 32B) Listing of miRNAs and exact target sites relative to the PR+1 site (miRNA target sites annotated as the base complementary to the first base of the miRNA seed sequence).

FIGS. 33A-D. Potential for recognition of sequences downstream from the 3'-UTR by miRNAs. (FIG. 33A) Schematic of algorithm used to predict miRNA targets within sequences downstream from 3'-UTRs. (FIG. 33B) Genome-wide comparison of the relative frequencies of seed matches between miRNAs and 3'-UTRs or sequences downstream from 3'-UTRs. (FIG. 33C) Number of seed sequence matches within 1000 bases of the termini of 3'-UTRs compared to matches within the same sequences after randomization. Data is separated into matches in either the sense or antisense orientation. Similar data for matches within 3'-UTRs is included for comparison. (FIG. 33D) Examples of high scoring predicted miRNA targets within sequences beyond 3'-UTRs. **p<0.01 compared to randomized sequences (SEQ ID NOS:180-187).

DETAILED DESCRIPTION OF SPECIFIC EMBODIMENTS OF THE INVENTION

Figure 12:
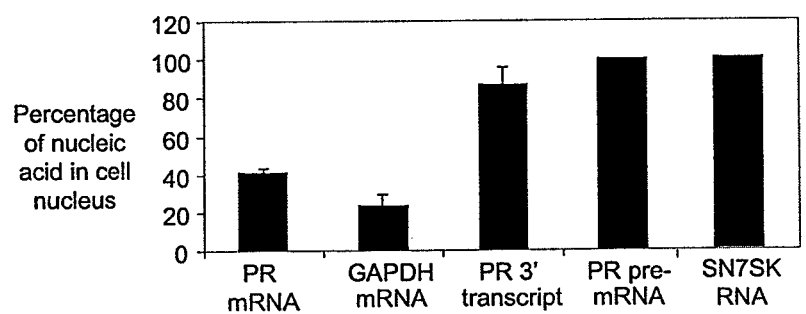
FIG. 12. qPCR measurement of nuclear localization of 3' noncoding transcript. SN7SK RNA is a nuclear RNA and is used as a standard.

There has been little investigation into the potential function of overlapping non-coding transcripts at the 3'-region, and no examination or whether these non-coding transcripts might be targets for modulating gene expression by small duplex RNAs. The ability of agRNAs to modulate gene expression by targeting overlapping 5' transcripts and the abundance of transcripts that overlap the 3'-UTR present the possibility that small RNAs might also be able to influence gene expression by recognizing sequences beyond the 3' termini of genes.

To examine the potential for small RNAs to recognize and act on 3' regions, the inventors characterized the 3'-UTR of endogenously expressed PR and targeted small duplex RNAs to key sequences within the 3'-UTR or downstream from its terminus. As discussed below, they found that RNAs complementary to sequences downstream from the characterized terminus of the 3'-UTR can also modulate gene transcription and recruit argonaute protein to a non-coding transcript. Small RNAs complementary to the 3'-UTR of a second well characterized gene in breast cancer cells, BRCA1, also modulation gene expression. These results extend the boundaries of RNA-mediated gene regulation and suggest that non-coding transcripts at the 3' termini of genes may play a role in controlling gene expression.

Thus, the present invention provides a general method of selectively modulating (increasing or decreasing) expression (i.e., transcription) of a target gene by contacting a cell with an oligomer that hybridizes to a region downstream of a 3'-UTR, thereby modulating expression of the target gene. In a particular embodiment, the target gene is a native gene, may be located in a cell, which may be in situ in a host. The modulated expression may be observed directly or inferred from a correlated physiologic change in the target cell or host.

As disclosed and exemplified herein, by exploiting this hitherto unappreciated endogenous mechanism for selective regulation of gene expression, these methods are generally applicable across a wide variety of target genes, 3'-UTR regions, oligomer, cell types and delivery conditions. While conditions whereby a given oligomer selectively modulates expression of a given target gene may be confirmed empirically (e.g., pursuant to the protocols described herein), these data indicate that mammalian cells are generally amenable to target gene selective modulation of target gene expression using these methods.

Various aspects of the invention, as set forth above, are described in greater detail in the following paragraphs.

I. Definitions

For ease of exposition the term "nucleotide" or "ribonucleotide" is sometimes used herein in reference to one or more monomeric subunits of an RNA agent. It will be understood that the usage of the term "ribonucleotide" or "nucleotide" herein can, in the case of a modified RNA or nucleotide surrogate, also refer to a modified nucleotide, or surrogate replacement moiety, as further described below, at one or more positions. It is also appreciated that the term "nucleotide" may refer to deoxynucleotides (DNA) or DNA-like monomers.

An "oligomer" as used herein is an agent, whether single- or double-stranded, that hybridizes in intracellular conditions to a target molecule, e.g., an RNA (sense or antisense).

An "RNA oligomer" as used herein is an unmodified RNA, modified RNA, or nucleoside surrogate, all of which are described herein. While numerous modified RNAs and nucleoside surrogates are described, particular examples include those which have greater resistance to nuclease degradation than do unmodified RNAs, including those having a 2' sugar modification, a modification in a single strand overhang, including a 3' single-strand overhang, or, particularly if single-stranded, a 5'-modification which includes one or more phosphate groups or one or more analogs of a phosphate group.

An "iRNA agent" (abbreviation for "interfering RNA agent") as used herein, is an agent which can down-regulate the expression of a target gene. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can be a single-stranded or double-stranded iRNA agent.

A "double-stranded" or "duplex" agent, as used herein, is an agent which includes more than one, and preferably two, strands in which interstrand hybridization can form a region of duplex structure. A "strand" herein refers to a contigouous sequence of nucleotides, including non-naturally occurring or modified nucleotides. The two or more strands may be, or each form a part of, separate molecules, or they may be covalently interconnected, e.g., by a linker, e.g., a polyethyleneglycol linker, to form but one molecule. At least one strand can include a region which is sufficiently complementary to a target RNA. Such strand is termed the "antisense" strand. A second strand comprised in the agent which comprises a region complementary to the antisense strand is termed the "sense" strand. However, a duplex agent can also be formed from a single molecule which is, at least partly, self-complementary, thereby forming a hairpin or panhandle structure, including a duplex region. In such case, the term "strand" refers to one of the regions of the oligomer that is complementary to another region of the same oligomer.

As used herein, the term "complementary" is used to indicate a sufficient degree of complementarity such that stable and specific binding occurs between a compound featured in the invention (e.g., an oliogomer) and a target RNA molecule. Specific binding requires a sufficient degree of complementarity to avoid non-specific binding of the oligomeric compound to non-target sequences under conditions in which specific binding is desired, e.g., under physiological conditions in the case of in vivo assays or therapeutic treatment, or in the case of in vitro assays, under conditions in which the assays are performed. The non-target sequences typically differ by at least four nucleotides.

As used herein, an agent is "sufficiently complementary" to a target RNA if the agent alters the production of a protein related to (e.g., either transcribed from or known to be in a biological pathway associated with the target gene) the target RNA in a cell. The agent may also be "exactly complementary" to the target RNA, e.g., the target RNA and the agent anneal to form a hybrid made exclusively of Watson-Crick basepairs in the region of exact complementarity. A "sufficiently complementary" agent can include an internal region (e.g., of at least 10 nucleotides) that is exactly complementary to a target RNA. Moreover, in some embodiments, the agent specifically discriminates a single-nucleotide difference. In this case, the agent only mediates RNAi if exact complementary is found in the region (e.g., within 7 nucleotides of) the single-nucleotide difference.

As used herein, "essentially identical" when used referring to a first nucleotide sequence in comparison to a second nucleotide sequence means that the first nucleotide sequence is identical to the second nucleotide sequence except for up to one, two or three nucleotide substitutions.

As used herein, a "subject" refers to a mammalian organism. The subject can be any mammal, such as a cow, horse, mouse, rat, dog, pig, goat, or a primate. In the preferred embodiment, the subject is a human.

II. Oligomers

Oligomers of the present invention comprise nucleic acids or modified nucleic acids/analogs. These oligomers target one or more regions beyond the '3 terminus (downstream) of 3'-UTRs from target genes, and as such, constitute a previously unknown class of reagents for modulation of gene expression.

In general, design will start using previous published/deposited data to predict the 3' termini of the target gene. Such data is a useful starting point, but it is important that the 3' termini of these genes be characterized in the experimental cell lines used in these studies.

In this characterization, to establish the approximate end of the mRNAs, the inventors use multiple primer sets complementary to sequences throughout the predicted mRNAs and beyond the predicted terminus. RNA levels detected using the primer sets complementary to mRNA should be much higher than RNA levels for primer sets complementary to sequences downstream from the termini. To establish the identities of the 3' termini of these genes, 3'-RACE (Scotto-Lavino et al., 2006) can be used.

Once the mRNA termini are defined according the methods herein, six to ten RNAs are designed to target sequences downstream. These sequences will be chosen to have 30%-70% C/G content and have minimal complementarity to other sequences in the genome as verified by BLAST (Altschul et al., 1990). Sequences will be examined for conservation across species. Absolute conservation is not necessary, but highly conserved sequences would be high priority targets for investigation.

For the initial studies in cell culture, all duplex RNAs can use standard RNA bases (no chemical modifications) and will be obtained from commercial sources. For studies in animals, duplex RNAs may have chemical modifications to enhance biostability or to improve other properties. Particular oliogonucleotides for use according to the present invention include SEQ ID NOS: 9-41 (REVISE—THIS APPLN HAS 1-33).

A. agRNAs

Antigene RNAs, or "agRNAs," are short nucleic acids, or oligonucleotides, that exhibit both inhibitory and stimulatory effects on the expression of various target genes. Though structurally similar to siRNAs, agRNAs are believed to target chromosomal DNA and not RNA, or at least not the coding mRNAs (Tang et al., 2004; Janowski et al., 2005a; 2005b).

Oligonucleotides of the present invention are nucleic acid segments of 12-30 bases in length that are designed to regions downstream of 3'UTRs in target cells. In particular, ranges of 12-23, 15-30, 15-23, 18-23, 19-23, 20-23 and 21-23 bases are contemplated, as are specific lengths of 12, 13, 14, 15, 16, 17, 18, 19, 20, 21, 22, 23, 24 and 25 bases. In general, oligomers of the present invention are oligonucleotides that target a region downstream of a 3'UTR. These oliomers may be single-stranded, double-stranded (duplex), partially double-stranded (partially duplex), hairpin or structured.

Oligonucleotides are chemically synthesized using nucleoside phosphoramidites. A phosphoramidite is a derivative of natural or synthetic nucleoside with protection groups added to its reactive exocyclic amine and hydroxy groups. The naturally occurring nucleotides (nucleoside-3'-phosphates) are insufficiently reactive to afford the synthetic preparation of oligonucleotides. A dramatically more reactive (2-cyanoethyl) N,N-diisopropyl phosphoramidite group is therefore attached to the 3'-hydroxy group of a nucleoside to form nucleoside phosphoramidite. The protection groups prevent unwanted side reactions or facilitate the formation of the desired product during synthesis. The 5'-hydroxyl group is protected by DMT (dimethoxytrityl) group, the phosphite group by a diisopropylamino (iPr2N) group and a 2-cyanoethyl ($OCH_2CH_2CN$) group. The nucleic bases also have protecting groups on the exocyclic amine groups (benzoyl, acetyl, isobutyryl, or many other groups). In RNA synthesis, the 2' group is protected with a TBDMS (t-butyldimethylsilyl) group or with a TOM (t-butyldimethylsilyloxymethyl)

group. With the completion of the synthesis process, all the protection groups are removed.

Whereas enzymes synthesize DNA in a 5' to 3' direction, chemical DNA synthesis is performed "backwards" in a 3' to 5' reaction. Based on the desired nucleotide sequence of the product, the phosphoramidites of nucleosides A, C, G, and T are added sequentially to react with the growing chain in a repeating cycle until the sequence is complete. In each cycle, the product's 5'-hydroxy group is deprotected and a new base is added for extension. In solid-phase synthesis, the oligonucleotide being assembled is bound, via its 3'-terminal hydroxy group, to a solid support material on which all reactions take place. The 3' group of the first base is immobilized via a linker onto a solid support (most often, controlled pore glass particles or macroporouspolystyrene beads). This allows for easy addition and removal of reactants. In each cycle, several solutions containing reagents required for the elongation of the oligonucleotide chain by one nucleotide residue are sequentually pumped through the column from an attached reagent delivery system and removed by washing with an inert solvent.

Oligomers can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism. Modifications can also increase sequence specificity, and consequently decrease off-site targeting. In one embodiment, the oligomer includes a non-nucleotide moiety, e.g., a cholesterol moiety. The non-nucleotide moiety can be attached to the 3' or 5' end of the oligonucleotide agent.

A wide variety of well-known, alternative oligonucleotide chemistries may be used (see, e.g., U.S. Patent Publications 2007/0213292, 2008/0032945, 2007/0287831, etc.), particularly single-stranded complementary oligonucleotides comprising 2' methoxyethyl, 2'-fluoro, and morpholino bases (see e.g., Summerton and Weller, 1997). The oligonucleotide may include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). Also contemplated are locked nucleic acid (LNA) and peptide nucleic acids (PNA).

B. Nucleic Acid Mimics

Peptide nucleic acids (PNAs) are nonionic DNA mimics that have outstanding potential for recognizing duplex DNA (Kaihatsu et al., 2004; Nielsen et al., 1991). PNAs can be readily synthesized and bind to complementary sequences by standard Watson-Crick base-pairing (Egholm et al., 1993), allowing them to target any sequence within the genome without the need for complex synthetic protocols or design considerations. Strand invasion of duplex DNA by PNAs is not hindered by phosphate-phosphate repulsion and is both rapid and stable (Kaihatsu et al., 2004; Nielsen et al., 1991). Applications for strand invasion by PNAs include creation of artificial primosomes (Demidov et al., 2001), inhibition of transcription (Larsen and Nielsen, 1996), activation of transcription (Mollegaard et al., 1994), and directed mutagenesis (Faruqi et al., 1998). PNAs would provide a general and potent strategy for probing the structure and function of chromosomal DNA in living systems if their remarkable strand invasion abilities could be efficiently applied inside cells.

Strand invasion by PNAs in cell-free systems is most potent at sequences that are partially single-stranded (Bentin and Nielsen, 1996; Zhang et al., 2000). Assembly of RNA polymerase and transcription factors into the pre-initiation complex on DNA induces the formation of a structure known as the open complex that contains several bases of single-stranded DNA (Holstege et al., 1997; Kahl et al., 2000). The exceptional ability of PNAs to recognize duplex DNA allows them to intercept the open complex of an actively transcribed gene without a requirement for preincubation. The open complex is formed during transcription of all genes and PNAs can be synthesized to target any transcription initiation site. Therefore, antigene PNAs that target an open complex at a promoter region within chromosomal DNA would have the potential to be general tools for controlling transcription initiation inside cells.

A locked nucleic acid (LNA), often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. Such oligomers are commercially available. The locked ribose conformation enhances base stacking and backbone pre-organization. This significantly increases the thermal stability (melting temperature) of oligonucleotides (Kaur et al., 2006). LNA bases may be included in a DNA backbone, by they can also be in a backbone of LNA, 2'-O-methyl RNA, 2'-methoxyethyl RNA, or 2'-fluoro RNA. These molecules may utilize either a phosphodiester or phosphorothioate backbone.

Other oligonucleotide modifications can be made to produce oligomers of the present invention. For example, stability against nuclease degradation has been achieved by introducing a phosphorothioate (P=S) backbone linkage at the 3' end for exonuclease resistance and 2' modifications (2'-OMe, 2'-F and related) for endonuclease resistance (WO 2005115481; Li et al., 2005; Choung et al., 2006). A motif having entirely of 2'-O-methyl and 2'-fluoro nucleotides has shown enhanced plasma stability and increased in vitro potency (Allerson et al., 2005). The incorporation of 2'-O-Me and 2'-O-MOE does not have a notable effect on activity (Prakash et al., 2005).

Sequences containing a 4'-thioribose modification have been shown to have a stability 600 times greater than that of natural RNA (Hoshika et al, 2004). Crystal structure studies reveal that 4'-thioriboses adopt conformations very similar to the C3'-endo pucker observed for unmodified sugars in the native duplex (Haeberli et al., 2005). Stretches of 4'-thio-RNA were well tolerated in both the guide and nonguide strands. However, optimization of both the number and the placement of 4'-thioribonucleosides is necessary for maximal potency.

In the boranophosphate linkage, a non-bridging phosphodiester oxygen is replaced by an isoelectronic borane (BH3—) moiety. Boranophosphate siRNAs (BNAs) have been synthesized by enzymatic routes using T7 RNA polymerase and a boranophosphate ribonucleoside triphosphate in the transcription reaction. Boranophosphate siRNAs are more active than native siRNAs if the center of the guide strand is not modified, and they may be at least ten times more nuclease resistant than unmodified siRNAs (Hall et al., 2004; Hall et al., 2006).

Certain terminal conjugates have been reported to improve or direct cellular uptake. For example, NAAs conjugated with cholesterol improve in vitro and in vivo cell permeation in liver cells (Rand et al., 2005). Soutschek et al. (2004) have reported on the use of chemically-stabilized and cholesterol-conjugated siRNAs have markedly improved pharmacological properties in vitro and in vivo. Chemically-stabilized siRNAs with partial phosphorothioate backbone and 2'-O-methyl sugar modifications on the sense and antisense strands (discussed above) showed significantly enhanced resistance towards degradation by exo- and endonucleases in serum and in tissue homogenates, and the conjugation of cholesterol to the 3' end of the sense strand of an oligonucleotides by means of a pyrrolidine linker does not result in a significant loss of gene-silencing activity in cell culture. These study demonstrates that cholesterol conjugation significantly improves in vivo pharmacological properties of oligonucleotides.

U.S. Patent Publication No. 2008/0015162, incorporated herein by reference, provide additional examples of nucleic acid analogs useful in the present invention. The following excerpts are derived from that document and are exemplary in nature only.

In certain embodiments, oligomeric compounds comprise one or more modified monomers, including 2'-modified sugars, such as BNA's and monomers (e.g., nucleosides and nucleotides) with 2'-substituents such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl.

In certain embodiments, the oligomeric compounds including, but no limited to short antisense compounds of the present invention, comprise one or more high affinity monomers provided that the oligomeric compound does not comprise a nucleotide comprising a 2'-O$(CH_2)_n$H, wherein n is one to six. In certain embodiments, the oligomeric compounds including, but no limited to short antisense compounds of the present invention, comprise one or more high affinity monomer provided that the oligomeric compound does not comprise a nucleotide comprising a 2'-$OCH_3$ or a 2'-O$(CH_2)_2OCH_3$. In certain embodiments, the oligomeric compounds including, but no limited to short antisense compounds of the present invention, comprise one or more high affinity monomer provided that the oligomeric compound does not comprise a α-L-methyleneoxy (4'-$CH_2$—O-2') BNA. In certain embodiments, the oligomeric compounds comprise one or more high affinity monomer provided that the oligomeric compound does not comprise a β-D-methyleneoxy (4'-$CH_2$—O-2') BNA and/or a β-D-methyleneoxy (4'-$CH_2$—O-2') BNA.

Certain BNA's have been prepared and disclosed in the patent literature as well as in scientific literature (Singh et al., 1998; Koshkin et al., 1998; Wahlestedt et al., 2000; Kumar et al., 1998; WO 94/14226; WO 2005/021570; Singh et al., 1998). Examples of issued US patents and published applications that disclose BNA's include, for example, U.S. Pat. Nos. 7,053,207; 6,268,490; 6,770,748; 6,794,499; 7,034,133; and 6,525,191; and U.S. Patent Publication Nos. 2004/0171570; 2004/0219565; 2004/0014959; 2003/0207841; 2004/0143114; and 2003/0082807.

Also provided herein are BNAs in which the 2'-hydroxyl group of the ribosyl sugar ring is linked to the 4' carbon atom of the sugar ring thereby forming a methyleneoxy (4'-$CH_2$—O-2') linkage to form the bicyclic sugar moiety (reviewed in Elayadi et al., 2001; Braasch et al., 2001, and Orum et al., 2001; see also U.S. Pat. Nos. 6,268,490 and 6,670,461). The linkage can be a methylene (—$CH_2$—) group bridging the 2' oxygen atom and the 4' carbon atom, for which the term methyleneoxy (4'-$CH_2$—O-2') BNA is used for the bicyclic moiety; in the case of an ethylene group in this position, the term ethyleneoxy (4'-$CH_2CH_2$—O-2') BNA is used (Singh et al., 1998; Morita et al., 2002). Methyleneoxy (4'-$CH_2$—O-2') BNA and other bicyclic sugar analogs display very high duplex thermal stabilities with complementary DNA and RNA ($T_m$=+3 to +10° C.), stability towards 3'-exonucleolytic degradation and good solubility properties. Potent and non-toxic antisense oligonucleotides comprising BNAs have been described (Wahlestedt et al., 2000).

An isomer of methyleneoxy (4'-$CH_2$—O-2') BNA that has also been discussed is α-L-methyleneoxy (4'-$CH_2$—O-2') BNA which has been shown to have superior stability against a 3'-exonuclease. The α-L-methyleneoxy (4'-$CH_2$—O-2') BNA's were incorporated into antisense gapmers and chimeras that showed potent antisense activity (Frieden et al., 2003).

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., 1998). BNAs and preparation thereof are also described in WO 98/39352 and WO 99/14226.

Analogs of methyleneoxy (4'-$CH_2$—O-2') BNA, phosphorothioate-methyleneoxy (4'-$CH_2$—O-2') BNA and 2'-thio-BNAs, have also been prepared (Kumar et al., 1998). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., 1998). In addition, 2'-amino- and 2'-methylamino-BNA's have been prepared and the thermal stability of their duplexes with complementary RNA and DNA strands has been previously reported.

Modified sugar moieties are well known and can be used to alter, typically increase, the affinity of oligomers for its target and/or increase nuclease resistance. A representative list of modified sugars includes, but is not limited to, bicyclic modified sugars (BNA's), including methyleneoxy (4'-$CH_2$—O-2') BNA and ethyleneoxy (4'-$(CH_2)_2$—O-2' bridge) BNA; sugars, especially 2'-substituted sugars having a 2'-F, 2'-$OCH_3$ or a 2'-O$(CH_2)_2$—$OCH_3$ substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; and 6,600,032; and WO 2005/121371.

The naturally-occurring base portion of a nucleoside is typically a heterocyclic base. The two most common classes of such heterocyclic bases are the purines and the pyrimidines. For those nucleosides that include a pentofuranosyl sugar, a phosphate group can be linked to the 2', 3' or 5' hydroxyl moiety of the sugar. In forming oligonucleotides, those phosphate groups covalently link adjacent nucleosides to one another to form a linear polymeric compound. Within oligonucleotides, the phosphate groups are commonly referred to as forming the internucleotide backbone of the oligonucleotide. The naturally occurring linkage or backbone of RNA and of DNA is a 3' to 5' phosphodiester linkage.

In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

Described herein are linking groups that link monomers (including, but not limited to, modified and unmodified nucleosides and nucleotides) together, thereby forming an oligomeric compound. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino ($-CH_2-N(CH_3)-O-CH_2-$), thiodiester ($-O-C(O)-S-$), thionocarbamate ($-O-C(O)(NH)-S-$); siloxane ($-O-Si(H)_2-O-$); and N,N'-dimethylhydrazine ($-CH_2-N(CH_3)-N(CH_3)-$). Oligomeric compounds having non-phosphorus linking groups are referred to as oligonucleosides. Modified linkages, compared to natural phosphodiester linkages, can be used to alter, typically increase, nuclease resistance of the oligomeric compound. In certain embodiments, linkages having a chiral atom can be prepared a racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

III. Target Genes/Cells/Hosts, Formulations and Delivery of Oligonucleotides A. Targets A target gene is generally native to a cell, such as a mammalian or human cell, and which may be in vitro (e.g., a cultured cell), or in situ in a host. Examples of cultured cells include primary cells, cancer cells (e.g., from cell lines), adult or embryonic stem cells, neural cells, fibroblasts, myocytes, etc. Cultured human cells commonly used to test putative therapeutics for human diseases or disorders can be used to screen subject oligomers for activity, especially therapeutic affect (e.g., induction of apoptosis, cessation of proliferation in cancer cells, etc.). When the cell is in situ, the host may be any mammal, such as a human, or an animal model used in the study of human diseases or disorders (e.g., rodent, canine, porcine, etc., animal models).

The mammalian cell may be determined to be in need of modulated expression of the target gene using routine methods. For example, reduced or increased levels of a target gene expression and/or protein relative to desired levels may be directly measured (see below). Alternatively, increased or decreased expression of a target gene may be inferred from a phenotype or physiologic status associated with reduced or increased levels of a target gene product.

B. Cell Delivery

A variety of methods may be used to deliver oligonucleotides, including oligomers, into a target cell. For cells in vitro embodiments, delivery can often be accomplished by direct injection into cells, and delivery can often be enhanced using hydrophobic or cationic carriers. Alternatively, the cells can be permeabilized with a permeabilization and then contacted with the oligonucleotide. The oligomer can be administered to the subject either as a naked oligonucleotide agent, in conjunction with a delivery reagent, or as a recombinant plasmid or viral vector which expresses the oligonucleotide agent.

For cells in situ, several applicable delivery methods are well-established, e.g., Elmen et al. (2008), Akinc et al. (2008); Esau et al. (2006), Krützfeldt et al. (2005). In particular, cationic lipids (see e.g., Hassani et al., 2005) and polymers such as polyethylenimine (see e.g., Urban-Klein, 2005) have been used to facilitate oligonucleotide delivery. Compositions consisting essentially of the oligomer (i.e., the oligomer in a carrier solution without any other active ingredients) can be directly injected into the host (see e.g., Tyler et al., 1999; McMahon et al., 2002). In vivo applications of duplex RNAs are reviewed in Paroo and Corey (2004).

When microinjection is not an option, delivery can be enhanced in some cases by using Lipofectamine™ (Invitrogen, Carlsbad, Calif.). PNA oligomers can be introduced into cells in vitro by complexing them with partially complementary DNA oligonucleotides and cationic lipid. The lipid promotes internalization of the DNA, while the PNA enters as cargo and is subsequently released. Peptides such as penetratin, transportan, Tat peptide, nuclear localization signal (NLS), and others, can be attached to the oligomer to promote cellular uptake (see e.g., Kaihatsu et al., 2003; Kaihatsu et al., 2004). Alternatively, the cells can be permeabilized with a permeabilization agent such as lysolecithin, and then contacted with the oligomer.

Alternatively, certain oligonucleotide agents featured in the instant invention can be expressed within cells from eukaryotic promoters (e.g., Izant and Weintraub, 1985; McGarry and Lindquist, 1986; Scanlon et al., 1991; Kashani-Sabet et al., 1992; Weerasinghe et al., 1991; Ojwang et al., 1992; Chen et al., 1992; Sarver et al., 1990; Thompson et al., 1995). Those skilled in the art realize that any nucleic acid can be expressed in eukaryotic cells from the appropriate DNA/RNA vector. The activity of such nucleic acids can be augmented by their release from the primary transcript by a enzymatic nucleic acid (PCT WO 93/23569; PCT WO 94/02595; Ohkawa et al., 1992; Taira et al., 1991; Ventura et al., 1993; Chowrira et al., 1994).

The recombinant vectors can be DNA plasmids or viral vectors. Oligonucleotide agent-expressing viral vectors can be constructed based on, but not limited to, adeno-associated virus, retrovirus, adenovirus, or alphavirus. In another embodiment, pol III based constructs are used to express nucleic acid molecules of the invention (see for example Morris et al., 2004; U.S. Pat. Nos. 5,902,880 and 6,146,886). The recombinant vectors capable of expressing the oligonucleotide agents can be delivered as described above, and can persist in target cells. Alternatively, viral vectors can be used that provide for transient expression of nucleic acid molecules. Such vectors can be repeatedly administered as necessary. Once expressed, the oligomer interacts with the target sequence. In a particular embodiment, the oligomer forms a duplex with target mRNA. Delivery of oligonucleotide agent-expressing vectors can be systemic, such as by intravenous or intra-muscular administration, by administration to target cells explanted from a subject followed by reintroduction into the subject, or by any other means that would allow for introduction into the desired target cell (see Couture et al., 1996).

Methods for the delivery of nucleic acid molecules are also described in Akhtar (1995), Akhtar et al. (1992), Maurer et al.

(1999), Hofland and Huang (1999), Lee et al. (2000), all of which are incorporated herein by reference. U.S. Pat. No. 6,395,713 and PCT WO 94/02595 and WO 00/53722 further describe general methods for delivery of nucleic acid molecules.

C. Routes of Administration

A composition that includes an oligomer can be delivered to a subject by a variety of routes. Exemplary routes include inhalation, parenchymal, subcutaneous, nasal, buccal and oral delivery. Also contemplated are delivery is through local administration directly to a disease site, or by systemic administration, e.g., parental administration. Parenteral administration includes intravenous (drip), subcutaneous, intraperitoneal or intramuscular injection, or intrathecal or intraventricular administration.

An oligomer featured in the invention can be administered to the subject by any means suitable for delivering the agent to the cells of the tissue at or near the area of unwanted target nucleic acid expression. Exemplary delivery methods include administration by gene gun, electroporation, or other suitable parenteral administration route.

Suitable parenteral administration routes include intravascular administration (e.g., intravenous bolus injection, intravenous infusion, intra-arterial bolus injection, intra-arterial infusion and catheter instillation into the vasculature); peri- and intra-tissue injection (e.g., intraocular injection); subcutaneous injection or deposition including subcutaneous infusion (such as by osmotic pumps); direct application to the area at or near the site of disease, for example by a catheter or other placement device.

D. Formulations

An oligomer can be incorporated into pharmaceutical compositions suitable for administration. For example, compositions can include one or more oligonucleotide agents and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Formulations for direct injection and parenteral administration are well known in the art. Such formulations may include sterile aqueous solutions which may also contain buffers, diluents and other suitable additives. For intravenous use, the total concentration of solutes should be controlled to render the preparation isotonic. An oligomer featured in the invention may be provided in sustained release compositions, such as those described in, for example, U.S. Pat. Nos. 5,672,659 and 5,595,760. The use of immediate or sustained release compositions depends on the nature of the condition being treated. If the condition consists of an acute or over-acute disorder, treatment with an immediate release form will be utilized versus a prolonged release composition. Alternatively, for certain preventative or long-term treatments, a sustained release composition may be appropriate. An oligomer can include a delivery vehicle, such as liposomes, for administration to a subject, carriers and diluents and their salts, and/or can be present in pharmaceutically acceptable formulations.

The oligonucleotide agents featured by the invention may be formulated as pharmaceutical compositions prior to administering to a subject, according to techniques known in the art. Pharmaceutical compositions featured in the present invention are characterized as being at least sterile and pyrogen-free. As used herein, "pharmaceutical formulations" include formulations for human and veterinary use. Methods for preparing pharmaceutical compositions are within the skill in the art, for example as described in Remington's Pharmaceutical Science, 18th ed., Mack Publishing Company, Easton, Pa. (1990), and The Science and Practice of Pharmacy, 2003, Gennaro et al., the entire disclosures of which are herein incorporated by reference.

The present pharmaceutical formulations include an oligomer featured in the invention (e.g., 0.1 to 90% by weight), or a physiologically acceptable salt thereof, mixed with a physiologically acceptable carrier medium. Particular physiologically acceptable carrier media are water, buffered water, normal saline, 0.4% saline, 0.3% glycine, hyaluronic acid and the like.

Pharmaceutical compositions featured in the invention can also include conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions can be packaged for use in liquid form, or can be lyophilized.

For solid compositions, conventional non-toxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can include any of the carriers and excipients listed above and 10-95%, in particular 25%-75%, of one or more single-stranded oligonucleotide agents featured in the invention.

Non-limiting examples of agents suitable for formulation with the nucleic acid molecules of the instant invention include: P-glycoprotein inhibitors (such as PluronicP85), which can enhance entry of drugs into the CNS (Jolliet-Riant and Tillement, 1999); biodegradable polymers, such as poly (DL-lactide-coglycolide) microspheres for sustained release delivery. Other non-limiting examples of delivery strategies for the nucleic acid molecules featured in the instant invention include material described in Boado et al. (1998, Tyler et al. (1999a; b); Pardridge et al. (1995); Boado (1995); Aldrian-Herrada et al. (1998).

The invention also features the use of a composition that includes surface-modified liposomes containing poly(ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al., 1995; Ishiwata et al., 1995).

Such liposomes have been shown to accumulate selectively in tumors, presumably by extravasation and capture in the neovascularized target tissues (Lasic et al., 1995; Oku et al., 1995). The long-circulating liposomes enhance the pharmacokinetics and pharmacodynamics of DNA and RNA, particularly compared to conventional cationic liposomes which are known to accumulate in tissues of the MPS (Liu et al., 1995; PCT Publication No. WO 96/10391; PCT Publication No. WO 96/10390; PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

The present invention also features compositions prepared for storage or administration that include a pharmaceutically effective amount of the desired oligonucleotides in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-β-cyclodextrin; and polysaccharides, such as raffinose, maltodextrins, dextrans, and the like; alditols, such as mannitol, xylitol, and the like. A particular group of carbohydrates includes lactose, threhalose, raffinose maltodextrins, and mannitol. Suitable polypeptides include aspartame. Amino acids include alanine and glycine, with glycine being specifically contemplated.

Suitable pH adjusters or buffers include organic salts prepared from organic acids and bases, such as sodium citrate, sodium ascorbate, and the like.

E. Dosage

An oligomer can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of oligomer (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of oligomer per kg of bodyweight. The unit dose, for example, can be administered by injection (e.g., intravenous or intramuscular, intrathecally, or directly into an organ), inhalation, or a topical application.

Delivery of an oligomer directly to an organ can be at a dosage on the order of about 0.00001 mg to about 3 mg per organ, or particularly about 0.0001-0.001 mg per organ, about 0.03-3.0 mg per organ, about 0.1-3.0 mg per organ or about 0.3-3.0 mg per organ.

Significant modulation of target gene expression may be achieved using nanomolar/submicromolar or picomolar/subnanomolar concentrations of the oligonucleotide, and it is typical to use the lowest concentration possible to achieve the desired resultant increased synthesis, e.g., oligonucleotide concentrations in the 1-100 nM range are contemplated; more particularly, the concentration is in the 1-50 nM, 1-25 nM, 1-10 nM, or picomolar range. In particular embodiments, the contacting step is implemented by contacting the cell with a composition consisting essentially of the oligonucleotide.

In one embodiment, the unit dose is administered once a day, e.g., or less frequently less than or at about every 2, 4, 8 or 30 days. In another embodiment, the unit dose is not administered with a frequency (e.g., not a regular frequency). For example, the unit dose may be administered a single time. Because oligonucleotide agent can persist for several days after administering, in many instances, it is possible to administer the composition with a frequency of less than once per day, or, for some instances, only once for the entire therapeutic regimen.

An oligomer featured in the invention can be administered in a single dose or in multiple doses. Where the administration of the oligomer is by infusion, the infusion can be a single sustained dose or can be delivered by multiple infusions. Multiple injections of the agent can be made into the tissue at or near the site.

In a particular dosage regimen, the oligomer is injected at or near a site of unwanted target nucleic acid expression once a day for seven days. Where a dosage regimen comprises multiple administrations, it is understood that the effective amount of oligomer administered to the subject can include the total amount of oligomer administered over the entire dosage regimen. One skilled in the art will appreciate that the exact individual dosages may be adjusted somewhat depending on a variety of factors, including the specific oligomer being administered, the time of administration, the route of administration, the nature of the formulation, the rate of excretion, the particular disorder being treated, the severity of the disorder, the pharmacodynamics of the oligonucleotide agent, and the age, sex, weight, and general health of the patient. Wide variations in the necessary dosage level are to be expected in view of the differing efficiencies of the various routes of administration. Variations in these dosage levels can be adjusted using standard empirical routines of optimization, which are well-known in the art. The precise therapeutically effective dosage levels and patterns can be determined by the attending physician in consideration of the above-identified factors.

In one embodiment, a subject is administered an initial dose, and one or more maintenance doses of an oligomer. The maintenance dose or doses are generally lower than the initial dose, e.g., one-half less of the initial dose. The maintenance doses are generally administered no more than once every 5, 10, or 30 days. Further, the treatment regimen may last for a period of time which will vary depending upon the nature of the particular disease, its severity and the overall condition of the patient. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

Certain factors may influence the dosage required to effectively treat a subject, including but not limited to the severity of the disease or disorder, previous treatments, the general health and/or age of the subject, and other diseases present. It will also be appreciated that the effective dosage of the oligomer used for treatment may increase or decrease over the course of a particular treatment. Changes in dosage may result and become apparent from the results of diagnostic assays. For example, the subject can be monitored after administering an oligomer composition. Based on information from the monitoring, an additional amount of the oligomer composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on $EC_{50}$'s found to be effective in in vitro and in vivo animal models.

IV. Targets and Disease States

A. Progesterone Receptor

The progesterone receptor (PR) also known as NR3C3 (nuclear receptor subfamily 3, group C, member 3), is an intracellular steroid receptor that specifically binds progesterone. PR is encoded by a single gene PGR residing on chromosome 11q22, it has two main forms, A and B, that differ in their molecular weight. Like all steroid receptors, the progesterone receptor has an amino and a carboxyl terminus, and between them the regulatory domain, a DNA binding domain, the hinge section, and the hormone binding domain. A special transcription activation function (TAF), called TAF-3, is present in the progesterone receptor-B, in a B-upstream segment (BUS) at the amino acid terminal. This segment is not present in the receptor-A.

As demonstrated in progesterone receptor-deficient mice, the physiological effects of progesterone depend completely on the presence of the human progesterone receptor (hPR), a member of the steroid-receptor superfamily of nuclear receptors. The single-copy human (hPR) gene uses separate promoters and translational start sites to produce two isoforms, hPR-A and -B, which are identical except for an additional 165 amino acids present only in the N terminus of hPR-B. Although hPR-B shares many important structural domains as hPR-A, they are in fact two functionally distinct transcription factors, mediating their own response genes and physiological effects with little overlap. Selective ablation of PR-A in a mouse model, resulting in exclusive production of PR-B, unexpectedly revealed that PR-B contributes to, rather than inhibits, epithelial cell proliferation both in response to estrogen alone and in the presence of progesterone and estrogen. These results suggest that in the uterus, the PR-A isoform is necessary to oppose estrogen-induced proliferation as well as PR-B-dependent proliferation.

Six variable sites, including four polymorphisms and five common haplotypes have been identified in the human PR gene. One promoter region polymorphism, +331G/A, creates a unique transcription start site. Biochemical assays showed that the +331G/A polymorphism increases transcription of the PR gene, favoring production of hPR-B in an Ishikawa endometrial cancer cell line.

Estrogen is necessary to induce the progesterone receptors. When no binding hormone is present, the carboxyl-terminus inhibits transcription. Binding to a hormone induces a structural change that removes the inhibitory action. Progesterone antagonists prevent the structural reconfiguration. After progesterone binds to the receptor, restructuring with dimerization follows and the complex enters the nucleus and binds to DNA. There transcription takes place, resulting in formation of messenger RNA that is translated by ribosomes to produce specific proteins.

The present invention contemplates regulation of PR expression using oligomers directed at regions beyond the 3'-UTR of the PR gene.

B. BRCA1

BRCA1 (breast cancer 1, early onset) is a human gene, some mutations of which are associated with a significant increase in the risk of breast cancer, as well as other cancers. BRCA1 belongs to a class of genes known as tumor suppressors, which maintains genomic integrity to prevent uncontrolled proliferation. The multifactorial BRCA1 protein product is involved in DNA damage repair, ubiquitination, transcriptional regulation as well as other functions. The BRCA1 gene is located on the long (q) arm of chromosome 17 at band 21, from base pair 38,449,843 to base pair 38,530,933 (map).

The BRCA1 protein is directly involved in the repair of damaged DNA. In the nucleus of many types of normal cells, the BRCA1 protein is thought to interact with RAD51 during repair of DNA double-strand breaks, though the details and significance of this interaction is the subject of debate. These breaks can be caused by natural radiation or other exposures, but also occur when chromosomes exchange genetic material (homologous recombination, e.g., "crossing over" during meiosis). The BRCA2 protein, which has a function similar to that of BRCA1, also interacts with the RAD51 protein. By influencing DNA damage repair, these three proteins play a role in maintaining the stability of the human genome.

BRCA1 directly binds to DNA, with higher affinity for branched DNA structures. This ability to bind to DNA contributes to its ability to inhibit the nuclease activity of the MRN complex as well as the nuclease activity of Mre11 alone. This may explain a role for BRCA1 to promote higher fidelity DNA repair by NHEJ. BRCA1 also colocalizes with γ-H2AX (histone H2AX phosphorylated on serine-139) in DNA double-strand break repair foci, indicating it may play a role in recruiting repair factors.

Certain variations of the BRCA1 gene lead to an increased risk for breast cancer. Researchers have identified more than 600 mutations in the BRCA1 gene, many of which are associated with an increased risk of cancer. Women who have an abnormal BRCA1 or BRCA2 gene have up to an 85% risk of developing breast cancer by age 70; increased risk of developing ovarian cancer is about 55% for women with BRCA1 mutations and about 25% for women with BRCA2 mutations. These mutations can be changes in one or a small number of DNA base pairs (the building blocks of DNA). Those mutations can be identified with PCR and DNA sequencing. In some cases, large segments of DNA are rearranged. Those large segments, also called large rearrangements, can be a deletion or a duplication of one or several exons in the gene. A mutated BRCA1 gene usually makes a protein that does not function properly because it is abnormally short. Researchers believe that the defective BRCA1 protein is unable to help fix mutations that occur in other genes. These defects accumulate and may allow cells to grow and divide uncontrollably to form a tumor.

The participation of BRCA1 in the development of breast cancer has been proposed in several studies where hypermethylation of its promoter. Some results suggest that hypermethylation could be considered as an inactivating mechanism for BRCA1 expression, which has been reported in some cancers. In addition to breast cancer, mutations in the BRCA1 gene also increase the risk on ovarian, fallopian tube and prostate cancers. Moreover, precancerous lesions (dysplasia) within the Fallopian tube have been linked to BRCA1 gene mutations. Thus, the present invention contemplates regulation of BRCA1 expression using oligomers directed at regions beyond the 3'-UTR of the BRCA1 gene.

C. LXR

The liver X receptor (LXR) is a member of the nuclear receptor family of transcription factors and is closely related to nuclear receptors such as PPAR, FXR and RXR. Liver X receptors (LXRs) are important regulators of cholesterol, fatty acid, and glucose homeostasis. Since there is no clear consensus on what the endogenous ligand of LXR is, LXR is referred to as an orphan receptor. Two isoforms of LXR have been identified and are referred to as LXRα and LXRβ. The liver X receptors are classified into subfamily 1 (thyroid hormone receptor-like) of the nuclear receptor superfamily, and are given the nuclear receptor nomenclature symbols NR1H3 (LXRα) and NR1H2 (LXRβ) respectively.

LXRα and LXRβ were discovered separately between 1994-1995. LXRα isoform was independently identified by two groups and initially named RLD-1 and LXR, whereas four groups identified the LXRβ isoform and called it UR, NER, OR-1, and RIP-15. The human LXRα gene is located on chromosome 11p11.2, while the LXRβ gene is located on chromosome 19q13.3. While the expression of LXRα and LXRβ in various tissues somewhat overlap, the tissue distribution pattern of these two isoforms overall differ considerably. LXRα expression is restricted to liver, kidney, intestine, fat tissue, macrophages, lung, and spleen and is highest in liver, hence the name liver X receptor α (LXRα). LXRβ is expressed in almost all tissues and organs, hence the early name UR (ubiquitous receptor). The different pattern of expression suggests that LXRα and LXRβ have different roles in regulating physiological function.

LXRα and LXRβ form heterodimers with the obligate partner 9-cis retinoic acid receptor (RXR). The LXR/RXR heterodimer can be activated with either an LXR agonist (oxysterols) or a RXR agonist (9-cis-retinoic acid). Oxysterols, the oxygenated derivatives of cholesterol, such as 22(R)-hydroxycholesterol, 24(S)-hydroxycholesterol, 27-hydroxycholesterol, and cholestenoic acid, are the natural ligands for LXR. After activation, LXR translocates to the nucleus and binds to LXR response element (LXRE), usually a variant of the idealized sequence AGGTCAN4AGGTCA, in the promoters of LXRs' target genes. Some synthetic LXR agonists have been developed, including nonsteroidal LXR agonists T0901317 and GW3965. Target genes of LXRs are involved in cholesterol and lipid metabolism regulation, including:

ABC—ATP Binding Cassette transporter isoforms A1, G1, G5, and G8
ApoE—Apolipoprotein E
CETP—Cholesterylester Transfer Protein
CYP7A1—Cytochrome P450 isoform 7A1—cholesterol 7α-hydroxylase
FAS—Fatty acid aynthase
LPL—Lipoprotein lipase
LXR-α—Liver X Receptor-α (receptor auto-upregulation)
SREBP-1c—Sterol Regulatory Element Binding Protein 1c The importance of LXRs in physiological lipid and cholesterol metabolism suggests that they may influence the development of metabolic disorders such as hyper lipidemia and atherosclerosis. Evidence for this idea has been observed by recent studies that linked LXR activity to the pathogenesis of atherosclerosis. LXRα knockout mice are healthy when fed with a low-cholesterol diet. However, LXRα knockout mice develop enlarged fatty livers, degeneration of liver cells, high cholesterol levels in liver, and impaired liver function when fed a high-cholesterol diet. LXRβ knockout mice are unaffected by a high-cholesterol diet, suggesting that LXRα and LXRβ have separate roles. LXRs regulate fatty acid synthesis by modulating the expression of sterol regulatory element binding protein-1c (SREBP-1c). LXRs also regulate lipid homeostasis in the brain. LXRα and LXRβ double-knockout mice develop neurodegenerative changes in brain tissue. LXRβ knockout mice results in adult-onset motor neuron degeneration in male mice.

LXR agonists are effective for treatment of murine models of atherosclerosis, diabetes, anti-inflammation, and Alzheimer's disease. Treatment with LXR agonists (hypocholamide, T0901317, or GW3965) lowers the cholesterol level in serum and liver and inhibits the development of atherosclerosis in murine disease models. Synthetic LXR agonist GW3965 improves glucose tolerance in a murine model of diet-induced obesity and insulin resistance by regulating genes involved in glucose metabolism in liver and adipose tissue. GW3965 inhibits the expression of inflammatory mediators in cultured macrophage and inflammation in mice. LXR agonists (T0901317, 22(R)-hydroxycholesterol, and 24(S)-hydroxycholesterol) were also shown to suppress the proliferation of prostate cancer and breast cancer cells as well as delay progression of prostate cancer from androgen-dependent status to androgen-independent status. Treatment with T0901317 decreases amyloidal β production in an Alzheimer's disease mouse model. However, both T0901317 and GW3965 have been reported to increase plasma and liver triglycerides in some mice models, indicating that T0901317 and GW3965 may not be a good candidate for a therapeutic agent. Developing new potent and effective LXR agonists without the undesirable side effects may be beneficial for clinical usage. When lipogenesis is increased by pharmacological activation of the liver X receptor, hepatic VLDL production is increased 2.5-fold, and the liver produces large TG-rich VLDL particles. Interestingly, glucose induces expression of LXR target genes involved in cholesterol homeostasis like ABCA1 which is defective in Tangier disease. A common feature of many metabolic pathways is their control by retinoid X receptor (RXR) heterodimers. It is interesting to note that LXR heterodimerizes with RXR. Promiscuous RXR also heterodimerises with PPAR members. PPAR-α plays a pivotal role in fatty acid catabolism in liver by upregulating the expression of numerous genes involved in mitochondrial fatty acid oxidation. Thus, RXR is a common partner of two nuclear receptors acting in opposite directions with regard to fatty acid metabolism. So both LXR and PPAR-α compete for the limited pool of RXR and this dynamic equilibrium determines the direction of lipid metabolism. The hexacyclic aromatic ketones (−)anthrabenzoxocinone and (−) bischloroanthrabenzoxocinone ((−)-BABX), derived from a *Streptomyces* sp., have micromolar affinity for LXRα.

There are a variety of conditions under which it would be beneficial to increase LXRα gene expression, including (i) an overall anti-atherosclerotic effect by increasing hepatic cholesterol catabolism, (ii) increase of ATP-binding cassette transporters, resulting in cholesterol efflux and blockade of intestinal cholesterol absorption, (iii) promoting reverse cholesterol transport by up-regulating apolipoproteins E, C-1, C-IV C-11, and (iv) ATP-binding cassette transporters in macrophages Inhibition of macrophage inflammatory responses and affect on microcrobial responses also could be achieved.

Conditions under which it would be beneficial to lower LXRα gene expression include in the potential drug-hormone interactions in patients undergoing hormone replacement therapies, with the goal to exploit maximum benefits of activated LXRα, but to avoid sustained activation of LXRα in these patients. In addition, in patients with type II diabetes, elevated insulin levels drives lipogenesis (process by which simple sugars such as glucose are converted to fatty acids, which are subsequently esterified with glycerol to form the triacylglycerols that are packaged in VLDL and secreted from the liver). The goal would be to decrease LXRα activation because it also drives lipogenesis in these patients.

V. Detecting Expression

The detecting step is implemented by detecting a significant change in the expression of the target gene, for example, by detecting at least a 10%, 25%, 50%, 200% or 500% increase in expression of the target gene, or at least a 10%, 25%, 50%, 75%, or 90% decrease in expression of the target gene, relative to a negative control, such as basal expression levels.

Detection may be effected by a variety of routine methods, such as directly measuring a change in the level of the target gene mRNA transcript, or indirectly detecting increased or decreased levels of the corresponding encoded protein compared to a negative control. Alternatively, resultant selective modulation of target gene expression may be inferred from phenotypic or physiologic changes that are indicative of increased or decreased expression of the target gene.

A. Nucleic Acid Detection

Assessing expression may involve quantitating mRNA. Northern blotting techniques are well known to those of skill in the art. Northern blotting involves the use of RNA as a target. Briefly, a probe is used to target an RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished.

Nucleic acids may be quantitated following gel separation and staining with ethidium bromide and visualization under UV light. Alternatively, if the nucleic acid results from a synthesis or amplification using integral radio- or fluorometrically-labeled nucleotides, the products can then be exposed to x-ray film or visualized under the appropriate stimulating spectra, following separation.

In one embodiment, visualization is achieved indirectly. Following separation of nucleic acids, a labeled nucleic acid is brought into contact with the target sequence. The probe is conjugated to a chromophore or a radiolabel. In another embodiment, the probe is conjugated to a binding partner, such as an antibody or biotin, and the other member of the binding pair carries a detectable moiety.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the Killin gene that may then be analyzed by direct sequencing.

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

B. Protein Detection

Antibodies can be used in characterizing protein expression in cells through techniques such as ELISAs and Western blotting. For example, antibodies may be immobilized onto a selected surface, such as a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for the target that differs the first antibody. Appropriate conditions include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2-4 hrs, at temperatures on the order of about 25°-27° C. Following incubation, the antisera-contacted surface is washed so as to remove non-immunocomplexed material. A particular washing procedure includes washing with a solution such as PBS/Tween®, or borate buffer.

To provide a detecting means, the second antibody may have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will also find use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel- or fluorescently-tagged secondary antibodies against the toxin moiety are considered to be of particular use in this regard.

C. Mass Spectrometry

By exploiting the intrinsic properties of mass and charge, mass spectrometry (MS) can resolve and confidently identify a wide variety of complex compounds, including nucleic acids and proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000).

ESI. ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 μL/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer, is delivered to the tip through an internal passage from a suitable source (such as from a chromatograph or directly from a sample solution via a liquid flow controller). By applying pressure to the sample in the capillary, the liquid leaves the capillary tip as small highly electrically charged droplets and further undergoes desolvation and breakdown to form single or multicharged gas phase ions in the form of an ion beam. The ions are then collected by the grounded (or negatively charged) interface plate and led through an the orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; and 5,986,258.

ESI/MS/MS. In ESI tandem mass spectroscopy (ESI/MS/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991). Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances, sample clean up is required (Nelson et al., 1994; Gobom et al., 2000).

SIMS. Secondary ion mass spectroscopy, or SIMS, is an analytical method that uses ionized particles emitted from a surface for mass spectroscopy at a sensitivity of detection of a few parts per billion. The sample surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analyzed by the mass spectrometer in this method.

LD-MS and LDLPMS. Laser desorption mass spectroscopy (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectroscopy). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and separation of fragments are due to different size causing different velocity. Each ion mass will thus have a different flight-time to the detector.

One can either form positive ions or negative ions for analysis. Positive ions are made from regular direct photoionization, but negative ion formation requires a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectra.

Other advantages with the LDLPMS method include the possibility of constructing the system to give a quiet baseline of the spectra because one can prevent coevolved neutrals from entering the flight tube by operating the instrument in a linear mode.

MALDI-TOF-MS.

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998). peptide and protein analysis (Roepstorff, 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Desiderio et al., 2000). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Jiang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al., 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers.

VI. Examples

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Maintenance and Treatment of Cultured Cells with Physiologic Stimuli.

T47D, MCF7, and MDA-MB-2231 cells were cultured at 5% $CO_2$ in RPMI media (Sigma) supplemented with 10% FBS (Atlanta Biologicals), 10 mM HEPES, 0.5% NEAA, 10 μg/mL insulin, and 1 mM sodium pyruvate (Sigma). For some experiments, T47D or MCF7 cells were cultured in media containing 5% dextran/charcoal-stripped FBS (Atlanta Biologicals) three days prior to treatment with either 17β-estradiol (E2) (Steraloids), epidermal growth factor (EGF) (Sigma), or interleukin-1β (Sigma). All cells were harvested for RNA following exposure to compound for 24 hours.

Cellular Delivery of Duplex RNAs and Expression Assays.

The inventors used RNAi-max (Invitrogen) to deliver duplex RNAs (Supplementary Table S1) into MCF7 or T47D cells as described (Janowski et al., 2006b). Cells were seeded at 150,000 cells per well in a six-well plates and were transfected with duplex RNAs two days later. Cells were harvested for RNA three days after transfection for RNA measurements and five days after transfection when measuring protein levels.

Total RNA was isolated using TRI reagent (Sigma).

For purification of poly(A) RNA total RNA was isolated from T47D or MCF7 cell pellets with GenElute™ Mammalian Total RNA Miniprep Kit (Sigma), and poly(A) RNA was purified from total RNA with Poly(A) Purist™ mRNA Purification Kit (Applied Biostystems). cDNA was synthesized using Applied Biosystem's High Capacity Reverse Transcription kit. qPCR was performed on a CFX-96 Real Time System (BioRad) using iTaq SYBR Supermix (BioRad) or the TaqMan Universal PCR Master Mix (Applied Biosystems). Primers were designed using primer3 software with the exception of primers for GAPDH, PR, and BRCA1 mRNA which were supplied by Applied Biosystems. Only those primer sets that show linear amplification over several orders of magnitude were used. RNA was treated with DNaseI (Worthington) prior to cDNA synthesis. cDNA was synthesized using Applied Biosystem's High Capacity Reverse Transcription kit. For analysis of protein levels, cell pellets were lysed and protein concentrations were quantified using the BCA assay (Pierce). Westerns were performed on protein lysates (30 μg per well for PR and 60 μg per well for BRCA1). Primary antibodies (Ab) included PR-Ab (6A1, Cell Signaling) and BRCA1-Ab (MS110, Calbiochem). β-actin-Ab (Sigma) was used as an internal control and for quantitation. Protein was visualized using HRP-tagged secondary anti-mouse antibody (Jackson Immunolabs) and Super Signal developing solution (Pierce). For experiments evaluating the effects of physiologic stimuli, T47D or MCF7 cells were cultured in media containing 5% dextran/charcoal-stripped FBS (serum-stripped media) (Atlanta Biologicals) the day after transfection (day-1). The next day (day-2) the cells were either switched to full media or maintained in stripped media supplemented with 17β-estradiol, EGF, or IL1β. Cells were harvested for RNA on day-3 and incubated overnight at 37° C. with shaking. Next day, SDS was added to 1.6% and samples were incubated at 65° C. for 30 min to inactivate restriction enzyme. 150 μL of sample was saved to check restriction enzyme efficiency. Samples were diluted to 2 mL volume with 1.2× final gene regions were adapted from the inventors' previously described protocol (Younger). RNA sequences were obtained from miRBase (Release 13.0) and gene sequences were obtained from Genome Browser (March 2006 genome assembly). Sequences overlapping gene termini were defined as the 1000 bases downstream of the annotated 3' end of the gene.

Northern Blot Analysis.

All reagents were purchased from Applied Biosystems unless otherwise noted. Poly(A) RNA (5 μg per lane) was denatured with formaldehyde and separated on 1% agarose gels containing formaldehyde. The gel was soaked in 0.05 M NaOH/1.5 M NaCl for 30 min with gentle shaking, rinsed with several changes of DEPC-treated water and soaked in 10×SSC buffer (1.5 M NaCl and 0.15 M sodium citrate) for 40 min. The separated RNA species in the gel were transferred to BrightStar®-Plus positively charged nylon membrane by vacuum transfer apparatus in 10×SSC buffer for 1.5 h and fixed to the membrane by cross-linking with UV light. After that, the blot was prehybridized in ULTRAhyb™ ultrasensitive hybridization buffer for at least 30 min and then hybridized overnight in ULTRAhyb™ buffer containing 0.1 nM psoralen-biotin labeled RNA probe at 68° C. Stringent washings were performed at 68° C. with NorthernMax low/high stringency wash buffers. RNA species were visualized by BrightStar® BioDetect™ nonisotopic detection kit following the manufacturer's instruction manual and subsequent exposure to film. Sizes of the mRNA species were determined by comparison with two RNA ladders (0.5-9 kb RNA Millenium Markers from Applied Biosystems & 0.5-10 kb RNA ladder from Invitrogen) that were run on adjacent gel lanes and stained with ethidium bromide. For synthesis of RNA probes (300-500 bases long), DNA template was generated by PCR with an antisense primer tailed by a T7-RNA-polymerase recognition sequence. After purification, the product was in vitro transcribed by MAXIscript® T7 kit, and then labeled by BrightStar® Psoralen-Biotin nonisotopic labeling kit according to the manufacturer's instructions.

Chromatin Immunoprecipitation (ChIP).

Transfections were performed as described above, and cells were crosslinked with formaldehyde (1%) three days after transfection. Before crosslinking, a small sample was collected for qPCR to confirm either silencing or activation. Cells were recovered by scraping and nuclei isolated. Nuclei were lysed in 1 mL lysis buffer (1% SDS, 10 mM EDTA, 50 mM Tris-HCl pH 8.1, 1× Roche protease inhibitor cocktail) and sonicated (2 pulses, 40% power, 30 sec). 100 μL of lysate was incubated overnight with 4 μg of monoclonal anti-RNAP2 antibody (Millipore 05-623) or mouse IgG negative control antibody (Millipore 12-371) diluted in 900 μL of immunoprecipitation buffer (0.01% SDS, 1.1% Triton-X, 1.2 mM EDTA, 16.7 mM Tris pH 8.1, 167 mM NaCl, and 1× Roche protease inhibitor cocktail). Antibody was recovered with 60 μL of Protein A/G beads (Calbiochem EMD IP05). Beads were washed with low salt (0.1% SDS, 1% Triton-X, 2 mM EDTA, 20 mM Tris-HCl pH 8.1, 150 mM NaCl), high salt (see low salt but with 500 mM NaCl), LiCl solution (0.25 M LiCl, 1% NP40, 1% deoxycholate, 1 mM EDTA, and 10 mM Tris-HCl pH 8.1), and Tris-EDTA pH 8 (Ambion AM9863) washes. Protein was eluted with 500 μL of 1% SDS, 0.1 M NaHCO3 for 30 min at room temperature. Crosslinking was reversed by adding NaCl to 200 mM and heating at 65° C. for at least 2 hours. Protein was digested by Proteinase K followed by extraction using an equal volume of phenol:chloroform:isoamyl alchohol and centrifugation. DNA in the aqueous layer was precipitated using 1/10 volume sodium acetate/2 volumes ethanol. The pellet was resuspended in 50 μL of nuclease-free water. Real time PCR was performed using BioRad iTaq SYBR® Supermix.

RNA Immunoprecipitation (RIP).

The general anti-AGO antibody was provided by Z. Mourelatos, University of Pennsylvania. MCF7 or T47D cells were grown in 150 cm$^2$ dishes and transfected with duplex RNAs using RNAiMax (Invitrogen). Cells were crosslinked using 1% (v/v) formaldehyde solution and harvested. Cells were lysed and nuclei obtained. Anti-AGO2 antibody (Millipore 07-590) or the general anti-AGO antibody was incubated with nuclear lysates overnight. The antibody-treated material was then mixed with Protein A/G Agarose Plus (Santa Cruz) and washed five times. Complex was eluted and crosslinking reversed by adding 200 mM NaCl and heating to 65° C. for two hours. Samples were treated with DNase I, reverse transcribed, and amplified.

Rapid Amplification of cDNA ends (RACE).

5'-RACE and 3'-RACE were performed according to the manufacturers protocol using the GeneRacer kit (Invitrogen). This kit includes enzymatic treatments that select for full length RNA with intact 5' caps rather than truncated products. For 5'-RACE, RNA was treated with phosphatase prior to removal of the cap to prevent cloning of truncated transcripts. For 3'-RACE, cDNA was made using oligo dT primers to allow cloning of the polyadenylated 3' ends. Multiple primer sets (Supplementary Table S4) were used to maximize detection of transcripts and reduce the likelihood of bias from any one primer set. The inventors used the Platinum Taq High Fidelity kit (Invitrogen) to produce product for cloning. PCR products were cloned into a PCR-4 Topo vector and sequenced (McDermott sequencing core, UT Southwestern). The inventors sequenced multiple clones from at least two independent experiments to confirm results.

Chromatin Conformation Capture.

20 million cells were grown and crosslinked in 1% formaldehyde. Cells were recovered by scraping (5 μg genomic DNA). Nuclei were purified using hypotonic lysis and distriubted into 1 million nuclei aliquots. Aliquots were stored at −80° C. An additional 10 million nuclei were recovered without the use of formaldehyde for a no crosslink control. Aliquots were removed from −80° C. storage and resuspended in 500 μL of 1× restriction buffer (RB) and 3% SDS and incubated for 1.5 hr at 37° C. with shaking at 1000 rpm to loosen chromatin. Then Triton-X was added to 1.8% and samples were incubated 1 hr more at 37° C. with shaking to sequester SDS. 300 units of restriction enzyme DpnII were added and incubated overnight at 37° C. with shaking. Next day, SDS was added to 1.6% and samples were incubated at 65° C. for 30 min to inactivate restriction enzyme. 150 μL of sample was saved to check restriction enzyme efficiency. Samples were diluted to 2 mL volume with 1.2× final concentration of ligase buffer and 1% final concentration of Triton-X. Samples were incubated at 37° C. for 1 hr. Samples were placed on ice and either 40 units of T4 ligase were added and incubated overnight at 16° C. The next day samples were incubated for 30 min at room temp. Crosslinks were reversed by adding NaCl to 200 mM and incubating at 65° C. for 2 hrs with proteinase K. Samples were then incubated with RNase A for 45 minutes at 41° C. Finally DNA was purified by phenol:chloroform extraction and ethanol:sodium acetate precipitation. DNA was resuspended in 50 μL of nuclease free water and 1 μL was used in each PCR reaction. Primers were designed to span several DpnII cut sites at the 5' end, 3' end, and internal sites. Various combinations of forward and reverse primers were tested. Positive control templates for primers were synthesized as single strand DNA oligonucleotides (Sigma). Product was cloned and sequenced to ensure product was specific. Sequenced products aligned with their respective sites in the genome with the GATC consensus sequence for DpnII between them.

Computational Methods.

miRNA sequences were obtained from miRBase (Release 13.0) and gene sequences were obtained from Genome Browser (March 2006 genome assembly). Sequences overlapping gene termini were defined as the 1000 bases downstream of the annotated 3' end of the gene. All gene sequences were searched for perfect complementarity to miRNA seed sequences (bases 2-8 of the mature miRNA sequence). The total number of seed matches was calculated and compared to total seed matches within 100 iterations of randomized sequences (randomized from actual 1000 bases downstream of gene termini). Minimum free energy (MFE) of hybridization values were calculated for miRNA sequences and sequences overlapping gene termini that contained seed matches. MFE values were calculated using RNAhybrid. The same criteria were used to identify potential miRNA target sites within the noncoding RNA overlapping the PR terminus downstream for +13,037.

Interferon Response Assay.

T47D and MCF7 cells were transfected with duplex RNAs and mRNA was recovered using TRIzol® (Invitrogen) at 72 h after transfection. As a positive control in parallel, cells were transfected with 0.1 and 0.5 μg/ml of poly(I:C) dsRNA sequence (Sigma). Total RNA from each sample was isolated, treated with deoxyribonuclease I (Worthington Biochemical Corporation) and used to synthesize cDNA with High-capacity cDNA Reverse Transcription Kit (Applied Biosystems). Relative gene expression levels were quantified with Interferon Response Detection Kit (System Biosciences) on Bio-Rad CFX96™ Real-time System and were scaled to the untreated sample (relative expression=1). Relative expression levels are shown on a log scale.

mRNA Stability Assay.

MCF7 seeded in 6-well plates at 2.5×10$^5$ cells/well and allowed to grow for 24 hours. Cells were transfected with 25 nM of mismatch containing RNA duplexes using oligofectamine RNAi-Max (Invitrogen) at a 2:1 ratio. Each treatment group contained triplicate samples. Medium containing either 1.25 µg/ml actinomycin D (Sigma) or vehicle was added to the wells 52 hours after transfection. Cells were harvested at different time points following actinomycin D treatment (4, 9, 24, 30 hours). Total RNA was harvested from each sample using TRIzol (Invitrogen). Equal amounts of total RNA were reverse transcribed using Applied Biosystem's High Capacity Reverse Transcription kit. Quantitative PCR was performed as previously described using primer sets to PR and 18S ribosomal RNA.

Cloning of the PR 3' Non-Coding RNA for Plasmid-Based Expression.

Total RNA from T47D cells was reverse transcribed using a High Capacity cDNA Reverse Transcription Kit (Applied Biosystems, Inc.). The cDNA sequence of the PR 3' noncoding RNA (3' NCR) was amplified by touchdown PCR with Hi Fidelity Platinum Taq (Invitrogen) using the following forward and reverse primers based upon the sequence of the mature PR 3' NCR determined from RACE experiments: 3'NCR-F, GGTTTCTTTCTCCAGGTCCTCACTGGC-CATAC (SEQ ID NO:201); 3'NCR-R, ggatccggGAGAGC-TATACTCTTAGTTTGTTATAGTGACTCCA (SEQ ID NO:202). PCR product was gel-purified and 3'-end adenine overhangs blunted by incubation with PfuTurbo DNA Polymerase (Stratagene) and 0.1 mM dNTPs in 1× PfuTurbo reaction buffer. Blunted PCR product was inserted into the Strataclone Mammalian Expression Vector pCMV-SC (Stratagene) following the manufacturer's recommended protocol. Correct orientation of the 3' NCR cDNA sequence for expression from the CMV promoter in the generated pCMV-SC-3'NCR vector was verified by sequencing.

Plasmid-Based Overexpression Experiments.

T47D, MCF7, or MDA-231 cells were seeded in six-well plates at 200,000 cells per well. Cells were transfected with plasmid DNA using Lipofectamine-2000 according to the manufacturer's instructions when the cells were 85% confluent. Cells were harvested for RNA 24 hours after transfection.

Branched DNA Assay (bDNA).

The Quantigene 2.0 bDNA assay was performed essentially as described by the manufacturer (Panomics/Affymetrix). Briefly, samples in 96-well plates were lysed in a 200 µL solution containing two parts nuclease-free water and one part lysis mixture. Proteinase K stock (50 µg/mL) was added to a final volume of 10 µL Proteinase K per milliliter prepared solution. The plates were then incubated at 55° C. for 60 minutes. Specific probes to detect human GAPDH (used as control for normalization) or human PR (mRNA, or other transcripts) were prepared in lysis mixture and blocking buffer was separately added to DNA capture plates. The probes were designed with the help of and manufactured by Panomics.

Lysed cells were added to the prepared bDNA plates containing probes in a ratio of (80 µL lysed cells to 20 µL probe preps). The plates were incubated overnight at 55° C. On the next day, the plates were removed to room temperature and washed using an automated washer. Wells were washed three times with 300 µL wash solution per well. The following steps consisted of three one-hour incubations in preamplifier, amplifier, and labeling probe respectively. The first two incubations were performed at 55° C., while the labeling probe incubation was at 50° C. Between each step was a set of washes as described above. After a final series of washes, substrate was added. Luminescence was measured in the wells using a spectrophotometer and an integration time of 200 milliseconds. Analysis was done after normalizing the plates with their corresponding GAPDH probes.

Example 2

Results

Characterization of the PR 3'-UTR and Overlapping Transcripts.

Working with agRNAs requires accurate identification of mRNA termini. Initially, however, the PR GenBank sequence had been inaccurately labeled with the 5' end extended too far upstream and the 3' terminus prematurely truncated (FIG. 1A, top). Northern analysis suggested lengths for PR mRNA variants19 but lacked a precise length for the largest variant (estimated to be 11.4 kB) (FIG. 1A, middle). A GenBank update based on a cluster of expressed sequence tags extended the 3' UTR downstream to +13,037 (FIG. 1A, bottom).

The inventors performed northern analysis with probes complementary to i) the protein-encoding region of PR mRNA (probe 1), ii) the terminus of PR mRNA at +13,037 predicted by the recent GenBank update (probe 2), and iii) a region immediately downstream from the predicted +13,037 terminus (probe 3) (FIG. 1B). Probe 1 yielded major products at ~5.5 kB and >10 kB, similar to results observed previously19 (FIG. 1C). Probe 2 (complementary to the region at the predicted PR terminus) yielded only the >10 kb band (FIGS. 1C-D), consistent with the conclusion that the band is full length PR mRNA. Probe 3 (complementary to the region immediately downstream of +13,037) did not detect transcript (FIG. 1D). Quantitative PCR (qPCR) revealed that RNA levels were relatively constant before abruptly dropping after nucleotide +13,037 (FIG. 1E, FIG. 10). 5' and 3' Rapid Amplification of cDNA Ends (RACE) detected polyadenylation sites near +13,037 (FIG. 11).

Characterization of Transcripts that Overlap the 3' Terminus of PR mRNA.

The inventors used 3' and 5' RACE to search for noncoding transcripts that overlap the 3' terminus and identified transcripts that are transcribed in sense orientation (i.e., synthesized in the same direction) relative to PR mRNA (FIG. 1F, FIGS. 2A-B, FIGS. 10-11). These 3' transcripts share a transcription start site at +11,325 and multiple polyadenylation sites 1400 to 1500 bases downstream from to the +13,037 terminus of PR mRNA. They did not detect antisense transcripts in this region. Since the 3' transcript is transcribed in the same direction as PR mRNA, the inventors tested whether it was long variant of PR mRNA. They performed RT-PCR using a forward primer (primer E) complementary to PR mRNA that was directly upstream of +11,325 (and therefore had no complementarity to the +11325/+14,546 transcript) and a reverse primer (primer G) upstream of +14,546 (FIG. 2A). No amplified product was detected (FIG. 2C, FIGS. 10C-D). By contrast, RT-PCR using a forward primer (primer F) directly downstream of +11,325 and reverse primer directly upstream of +14,546 (primer G) detected the +11325/+14,546 product. Sequencing confirmed the identity of the amplified primer F/primer G product as the +11,325/+14,546 transcript and revealed that the transcript was unspliced (Supplementary FIG. S2e). Beyond the +14,546 terminus of the noncoding transcript, qPCR revealed that RNA levels drop abruptly in both T47D and MCF7 cells (FIGS. 2D-E, FIG. 10). RT-PCR with one primer (primer F) complementary to a sequence shared by PR mRNA and the 3' noncoding transcript and a primer (primer H) downstream from +14,546 detected no product, suggesting that the mRNA does not extend past +13037 (FIG. 2C).

Many genes are transcribed beyond their poly-A sites and then cleaved to form the mature mRNA. PCR did not detect evidence for longer PR mRNA (FIG. 2C), but the inventors cannot exclude with certainty its existence or its involvement in the mechanism of 3' agRNAs. qPCR revealed that the 3' noncoding transcript was almost entirely in the nuclear fraction of cell lysates while PR mRNA was mostly in the cytoplasm (FIG. 12).

Figure 13C:
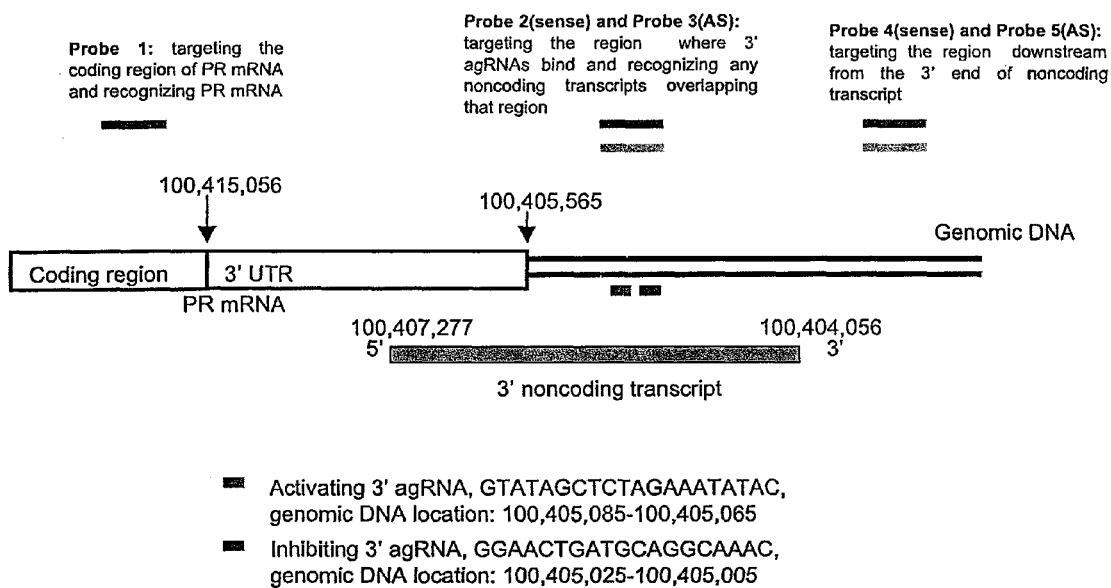

The inventors verified their data using the branched DNA (bDNA) assay (FIG. 13). The bDNA assay directly detects RNA using strand-specific probes that allow discrimination of sense and antisense transcripts. A probe set complementary to the sense transcript beyond +13,037 detected RNA at ~4% relative to the level of PR mRNA in either T47D or MCF7 cells. Assays with a probe set designed to detect a possible antisense transcript downstream from +13,037 suggested that an antisense transcript was either not present or was present a levels too low to detect.

Choice of Target Sequences for Duplex RNAs.

The inventors chose target sequences within the +11,325/+14,546 3' noncoding transcript but downstream from +13,037 terminus of PR mRNA. (Supplementary Table S1, FIG. 1F). Duplex RNAs are numbered by the position of the most upstream base relative to the +1 transcription start site for PR mRNA. They also tested duplex RNAs that target the PR promoter or PR mRNA to allow comparisons with other modulatory RNAs. The inventors have previously characterized agRNAs that target the promoter region (5' agRNAs) that modulate PR expression. PR-11 targets the region −11/+8 relative to the transcription start site and activates PR transcription in MCF7 and T47D cells6. PR-9 targets the region −9/+10 and is a robust transcriptional silencing agent in T47D cells (Janowski et al., 2005). PR3593 and PR2526 target PR mRNA.

Gene Inhibition by Small RNAs that Target Sequences Beyond the 3'-UTR.

The inventors tested several 3' agRNAs complementary to sequences downstream from the +13,037 terminus of PR mRNA (Supplementary Table S1, FIG. 1F). agRNAs PR13485 and PR13580 inhibited PR protein expression in T47D cells (FIG. 3A). PR has two major protein isoforms, PRB and PRA19 and both of these appear during western analysis. The $IC_{50}$ value for inhibition of PR13580 was 10.7 nM, similar to the value for inhibition by mRNA-targeting RNA PR2526, 11.5 nM (FIG. 3B, FIG. 14). Mismatch-containing duplex RNAs did not inhibit gene expression. Some of the control RNAs maintained the potential for seed sequence20 recognition of the duplex (PR13485_MM3, PR13580_MM3) demonstrating that seed sequence complementarity is not sufficient to induce the observed silencing (FIG. 3A).

Small RNAs can induce off-target effects through induction of the interferon response (21) Inhibitory 3' agRNA PR13580 did not significantly enhance expression of interferon-responsive genes (FIG. 15A) and was chosen for detailed investigation. Addition of poly(I:C), a potent inducer of the interferon response did not alter PR gene expression (FIG. 15B).

The inventors used qPCR to investigate how addition of inhibitory agRNA PR13580 affected RNA levels throughout the PR locus (FIG. 3C). The inventors' strategy was to use different primer sets, each designed to amplify a different RNA species including: i) the 5' antisense transcript at the PR promoter previously implicated in agRNA-mediated control of transcription (11), ii) the protein encoding region for PR mRNA, iii) intron 7 within PR pre-mRNA, an indicator of whether gene modulation occurs before or after splicing, and iv) the +11325/+14546 noncoding transcript overlapping the terminus of PR mRNA (FIG. 1F).

Addition of agRNA PR13580 to T47D cells reduced levels of PR mRNA (FIG. 3C). The level of PR pre-mRNA was also reduced, suggesting that modulation of RNA occurs prior to splicing. Levels of the noncoding transcript downstream from the terminus of the 3'-UTR were reduced, as were levels of the 5' noncoding transcript overlapping the transcription start site of PR. Negative control duplex RNA PR13063 did not reduce levels of PR mRNA (FIG. 16). The bDNA assay yielded similar results (FIG. 17).

To test whether agRNAs targeting sequences beyond the 3'-UTR altered gene transcription, the inventors measured RNAP2 occupancy at the PR promoter. Chromatin immunoprecipitation (ChIP) revealed that duplex agRNA PR13580 reduced occupancy of RNAP2 at the promoter (FIG. 3D). The inventors also measured levels of the histone modification H3K27me3 which serves as a chromatin-level marker for gene silencing (Barski et al., 2007). Addition of PR13580 to T47D cells led to a 27-fold increase in H3K27me3 levels within the PR gene relative to cells treated with mismatched control duplex (FIG. 3E). Addition of PR-9 also caused changes in RNAP2 occupancy and levels of H3K27me3. RNA PR3593 that targets PR mRNA did not decrease RNAP2 occupancy (FIG. 3D), emphasizing a basic difference in mechanism between agRNAs (inhibition of transcription) and duplex RNAs that function through post transcriptional gene silencing (PTGS) (inhibition of translation/destruction of mRNA).

Gene Activation by Small RNAs that Target Sequences Beyond the 3'-UTR.

The inventors hypothesized that agRNAs complementary to sequences beyond the 3' terminus of PR might also yield enhanced gene expression in MCF7 cells, a cell line where PR expression is low and increased expression is easily detectable. agRNA PR13515 increased levels of PR protein and mRNA (FIGS. 4A-C). Levels of PR pre-mRNA were also increased (FIG. 4C), consistent with the suggestion that RNA levels increase prior to splicing. For comparison, the inventors also measured RNA levels after addition of agRNA PR-11 that is complementary to the PR promoter/5' noncoding RNA transcript (Schwartz et al., 2008) and observed similar effects with all primer sets (FIG. 4C). The bDNA assay also revealed increased levels of PR mRNA and the 3' noncoding transcript upon addition of PR13515 or PR-11 (FIG. 17C).

Addition of either PR-11 or PR13515 led to enhanced RNAP2 recruitment at the PR transcription start site (FIG. 4D) and a decrease in the silencing marker H3K27me3 (FIG. 4E). The similarity of gene activation between PR-11 and PR13515 reinforces the suggestion that modulation of gene transcription by agRNAs proceeds through similar mechanisms regardless of whether their target regions are located beyond the 5' or 3' boundaries of mRNA.

The inventors tested whether increased stability of PR mRNA contributes to increased levels of PR mRNA following treatment with PR13515. Actinomycin D, a small molecule that inhibits transcription (Keen et al., 2005), was added to cells that had been previously treated with PR13515 or PR-11. The half-life of PR in MCF7 cells has been established to be 7-10 hours (Zaragoza et al., 2006). In MCF7 cells treated with either PR13515 or PR-11, addition of actinomycin D reversed the agRNA-mediated increase in PR mRNA. PR mRNA levels decreased by 8-10 fold within thirty hours.

(FIG. 4F). These data suggest that increased levels of PR mRNA are due to enhanced transcription.

The inventors tested several control RNAs to evaluate specificity. Control RNA PR13515_MM4 contained mismatched bases substituted throughout the sequence of PR13515. Control RNAs PR13515_MM3 and PR13515_MM3B that had mismatched bases clustered to preserve the potential for off-target effects that might arise from seed sequence complementarity (Nardulli et al., 1988) did not enhance protein expression (FIG. 4A). PR13515 did not increase expression of interferon-responsive genes and activation of the interferon response did not increase PR expression (FIGS. 15C-D). Off-target effects are a concern whenever duplex RNAs are introduced into cells. The inventors' 3' and 5' agRNAs have partial complementarity to other genes, but these matches do not suggest any source for off-target regulation of PR.

Effect of Physiological Stimuli on 3' Transcript Expression and agRNA Action.

17β-estradiol is a potent and well-characterized activator of PR gene expression in breast cancer cells (Nardulli et al., 1988). Conversely, expression of PR is decreased in cells grown in media containing charcoal-stripped serum and supplemented with either interleukin-1β (IL-1β) or epidermal growth factor (EGF) (Cho et al., 1994; Stoica et al., 2000; Zaragoza et al., 2006).

The inventors investigated how these physiologic stimuli would affect expression of the 3' and 5' noncoding transcripts (FIGS. 5A-B). PR mRNA levels were reduced in T47D and MCF7 cells grown using charcoal-stripped serum. Addition of EGF or IL-1β further reduced levels of PR mRNA, while addition of 17β-estradiol increased PR mRNA expression. In all cases, levels of the 3' noncoding transcript varied proportionally with PR mRNA (FIGS. 5A-B). By contrast, expression of the 5' noncoding transcript did not change significantly in T47D or MCF7 cells grown in charcoal-stripped serum, or in media supplemented with 17β-estradiol. Expression of the 5' transcript was decreased by addition of EGF or IL1β in MCF7 cells.

Figure 18:
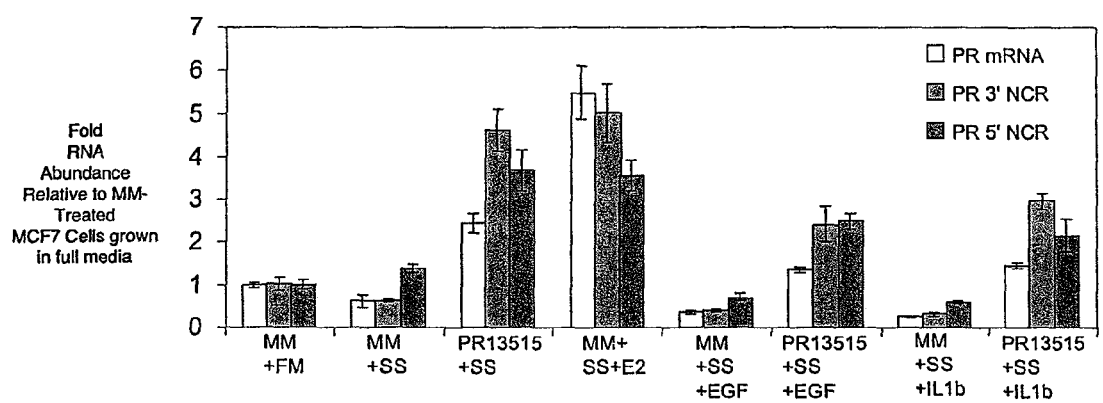
FIG. 18. Effect of combining physiologic stimuli with addition of agRNAs on expression of PR mRNA, the 3' noncoding RNA, and the 5' noncoding RNA. Data from FIG. 5D plotted without PR13515+FM and MM+SS+PR13515 data to allow easier comparison of other conditions. SS: serum-stripped media. FM: full media. E2: 17β estradiol treatment (100 nM). IL1β: interleukin 1β treatment (10 ng/mL). EGF: epidermal growth factor treatment (100 ng/mL). Data is derived from triplicate independent experiments.

The inventors then tested whether the addition of agRNAs would affect regulation of PR expression by physiologically relevant stimuli and, conversely, whether physiologic stimuli could block the action of agRNAs (FIGS. 5C-D, FIG. 18). Addition of inhibitory 3' agRNA PR13580 to T47D cells cultured in charcoal stripped serum supplemented with IL-1β or EGF led to a proportionate reduction in expression of PR mRNA and the 3' noncoding transcript to levels lower than those achieved by the physiologic treatments alone. Treating cells with 17β-estradiol increases PR mRNA expression (FIG. 5A) Inhibitory agRNA PR13580 reversed this effect, leading to low expression of PR (FIG. 5C) and almost unchanged expression of the 5' noncoding transcript regardless of physiologic treatment.

In MCF7 cells, addition of activating agRNA PR13515 in combination with 17β-estradiol yielded enhanced activation of PR gene expression to levels substantially above those achieved by addition of 17β-estradiol or PR13515 alone. PR13515 reversed the repressive effects from growth in charcoal-stripped serum, EGF addition, and IL1β addition on PR expression (FIG. 5D). These data suggest that activating and inhibitory agRNAs can counteract or supplement the effects of physiologic regulators on PR gene expression.

Argonaute Protein Recruitment by Noncoding RNAs.

Duplex agRNAs PR-9 and PR-11 are complementary to sequences within the PR promoter and recruit AGO protein to a noncoding transcript that overlaps the PR gene promoter (Schwartz et al., 2008). The sense noncoding transcript overlapping the 3' terminus of the PR gene (FIG. 1F) contains complementary target sites for inhibitory or activating agRNAs PR13580 and PR13515, and is a candidate for involvement in RNA-mediated gene modulation.

The inventors used RNA immunoprecipitation (RIP)28 from isolated nuclei with an anti-AGO2 antibody (FIG. 19) to examine recruitment of AGO2 protein to the 3' noncoding transcript during modulation of gene expression by agRNAs. When silencing agRNA PR13580 was added to T47D cells (FIG. 6A) or activating agRNA PR13515 was added to MCF7 cells (FIG. 6B), the inventors observed association between AGO2 and the 3' noncoding transcript. 5' agRNAs targeting a noncoding RNA at the PR promoter showed similar recruitment of AGO2 to the 5' noncoding transcript (FIGS. 6C-D). Sequencing confirmed the identity of the RIP products (FIG. 19). RIP with an anti-AGO1 antibody did not detect association of AGO1 (FIG. 20).

Inhibition of AGO2 Expression with an Anti-AGO2 siRNA Reversed Gene Silencing by PR13580.

Figure 21:
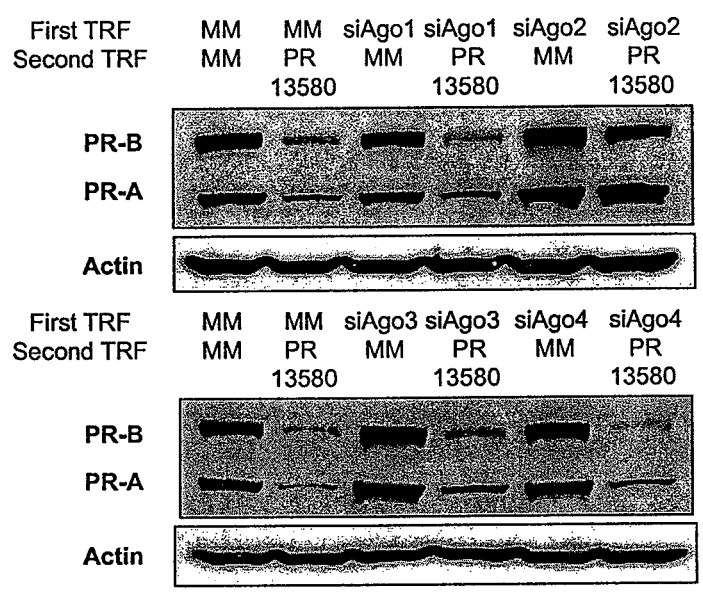
FIG. 21. Effect of silencing AGO1, AGO2, AGO3, or AGO4 expression on activity of PR13580. Duplex RNAs (complementary to the respective mRNAs) designed to inhibit expression of AGO1, AGO2, AGO3, or AGO4 were transfected into T47D cells at day 0. PR 13580 was transfected into cells at day 3, and cells were harvested for analysis of PR protein at day 7. All RNAs were added at 25 nM. Western analysis of PR protein levels after a double transfection assay using siAGO1, siAGO2, siAGO3, or siAGO4 in the initial transfection MM:mismatch-containing contro duplex. TRF: transfection.
Figure 22:
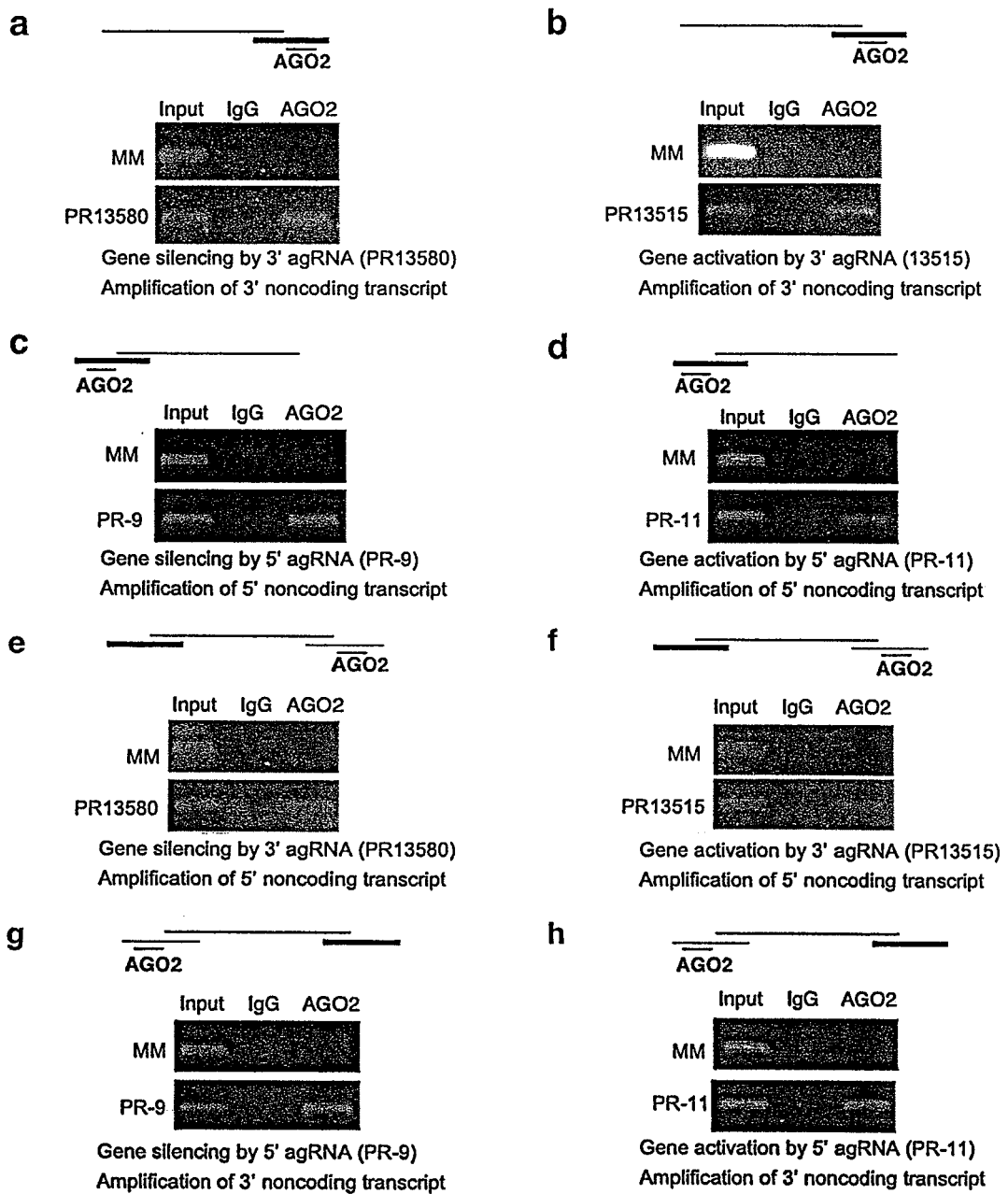
FIGS. 22A-H. Effect of 3' or 5' agRNAs on recruitment of AGO protein to the 3' or 5' noncoding transcripts at the PR locus. Unlike the experiments shown in FIGS. 4A-H, which used an antibody that recognizes AGO2, these experiments used an antibody that recognizes all four AGO variants indiscriminately (Nelson et al., *RNA* 13, 1787-1792 2007). Effect of adding (FIG. 22A) inhibitory RNA PR13580 to T47D cells or (FIG. 22B) activating RNA PR13515 to MCF7 cells on recruitment of AGO protein to the 3' noncoding transcript. Effect of adding (FIG. 22C) inhibitory RNA PR-9 to T47D cells or (FIG. 22D) activating RNA PR-11 to MCF7 cells on recruitment of AGO protein to the 5' noncoding transcript. Effect of adding (FIG. 22E) inhibitory RNA PR13580 to T47D cells or (FIG. 22F) activating RNA PR13515 to MCF7 cells on co-immunoprecipitaton of AGO protein with the 5' noncoding transcript. Effect of adding (FIG. 22G) inhibitory RNA PR-9 to T47D cells or (FIG. 22H) activating RNA PR-11 to MCF7 cells on co-immunoprecipitation of AGO protein with the 3' noncoding transcript. The scheme above each gel depicts PR mRNA, the 3' and/or 5' noncoding transcripts, and AGO bound agRNA. The heaviest line represents the transcript being amplified. Data is representative of four independent experiments.
Figure 23:
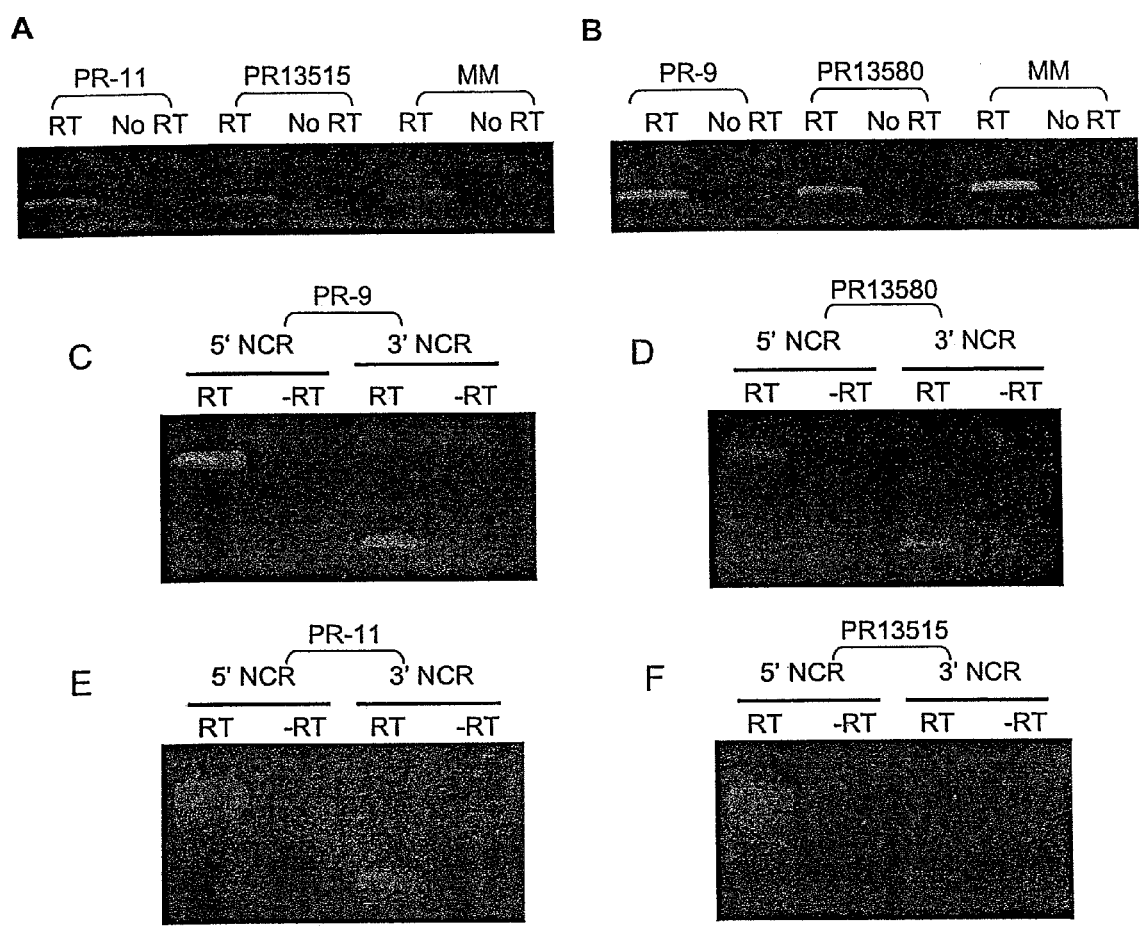
FIGS. 23A-F. The RIP assay detects RNA in the nucleus, not DNA. When reverse transcriptase (RT) is added, amplified product is observed. When no reverse transcriptase is added (no RT), no amplified product was detected. Detection of RNA in nuclear extracts after addition of RNAs to (FIG. 23A) MCF7 cells.

Inhibition of AGO1, AGO3, or AGO4 expression did not reverse gene silencing (FIG. 21). These data are consistent with a primary role for AGO2. The inventors observed the same results when using a well-characterized antibody that recognizes all four AGO proteins29 (FIGS. 22A-D). Identical RIP results using two different anti-AGO antibodies supports the specificity of AGO involvement in the mechanism of 3' agRNAs. No product was observed in the absence of reverse transcriptase (FIG. 23) or after transfection of cells with mismatch-containing duplex RNAs. Cytoplasmic proteins GAPDH and tubulin were not detected in the nuclei, indicating that the inventors are not detecting interactions in the cytoplasm.

Cleavage of the 3' Noncoding Transcript is not Detected.

Small RNAs that are complementary to mRNA can induce cleavage of their target transcripts (Siomi and Siomi, 2009). An important question of mechanism is whether 3' agRNAs act by promoting cleavage of the 3' noncoding transcript. The inventors readily detected cleavage of PR mRNA by PR2562, a duplex RNA that is complementary to the coding region of PR mRNA (FIGS. 24A-B).

Figure 24:
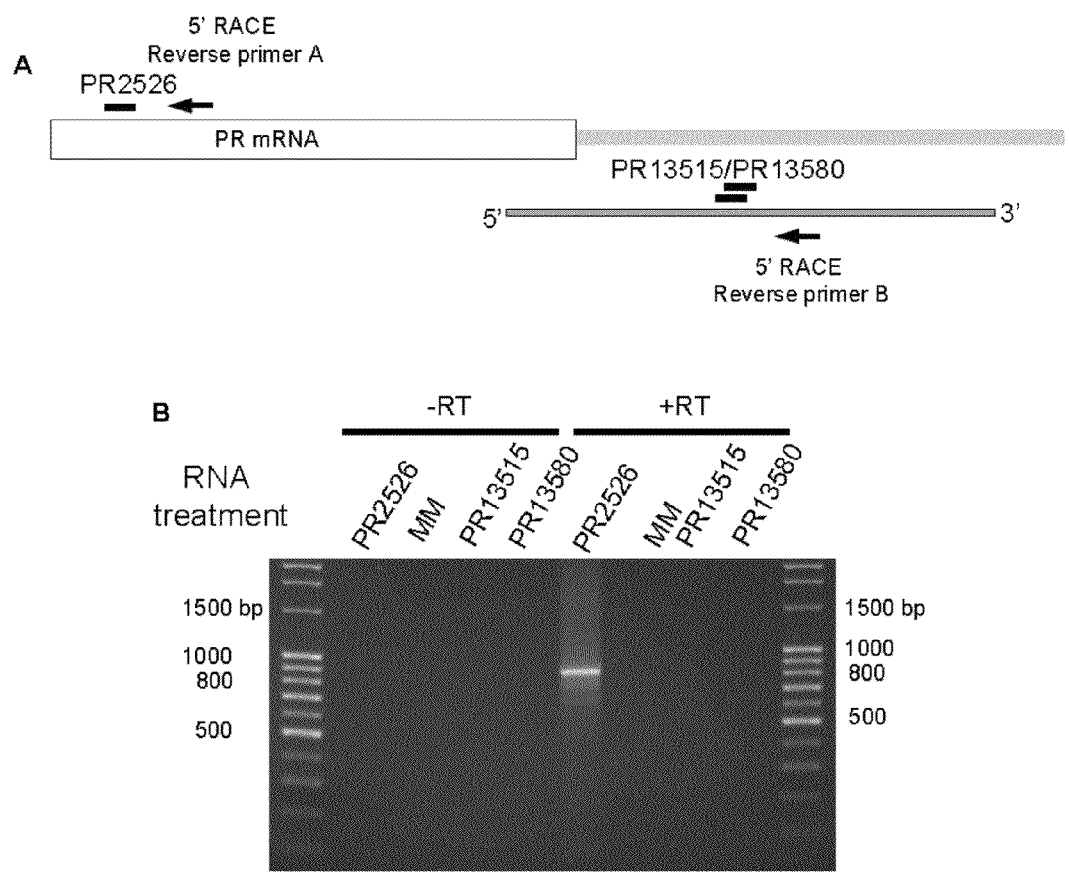
FIGS. 24A-B. 5'-RACE showing no detection of cleavage products within the 3' noncoding transcript after addition of activating agRNA PR13515 or inhibitory agRNA PR13580.

The inventors were unable to detect any cleavage of the 3' noncoding RNA using silencing agRNA PR13580 in T47D cells or activating agRNA PR13515 in MCF7 cells (FIGS. 24A-B). They note that the 3' noncoding transcript is expressed at relatively low levels and it is possible that cleavage might occur without being detectable by 5' RACE. Failure to detect any cleavage, however, is consistent with 1) the inventors' observation that addition of PR13515 enhances levels of the noncoding transcript (FIG. 4C) rather than reducing levels as would be predicted if transcript cleavage were occurring; 2) previous results showing that 5'agRNA PR-11 does not alter levels of the 5' noncoding transcript and does not cause detectable cleavage of the transcript (Janowski et al., 2007); and 3) RIP data showing association of AGO2 because the transcript must be intact if it is to be detected during RIP.

Overexpression of 3' Noncoding Transcript does not Affect PR mRNA Levels.

It is possible that the 3' noncoding transcript recruits AGO2 protein prior to its release from chromosomal DNA. Alternatively, the 3' noncoding transcript might be released from the chromosome and subsequently return to act at the PR locus. This latter mechanism would be similar to protein transcription factors that are synthesized in the cytoplasm and return to act on their target promoters in the nucleus.

Figure 25:
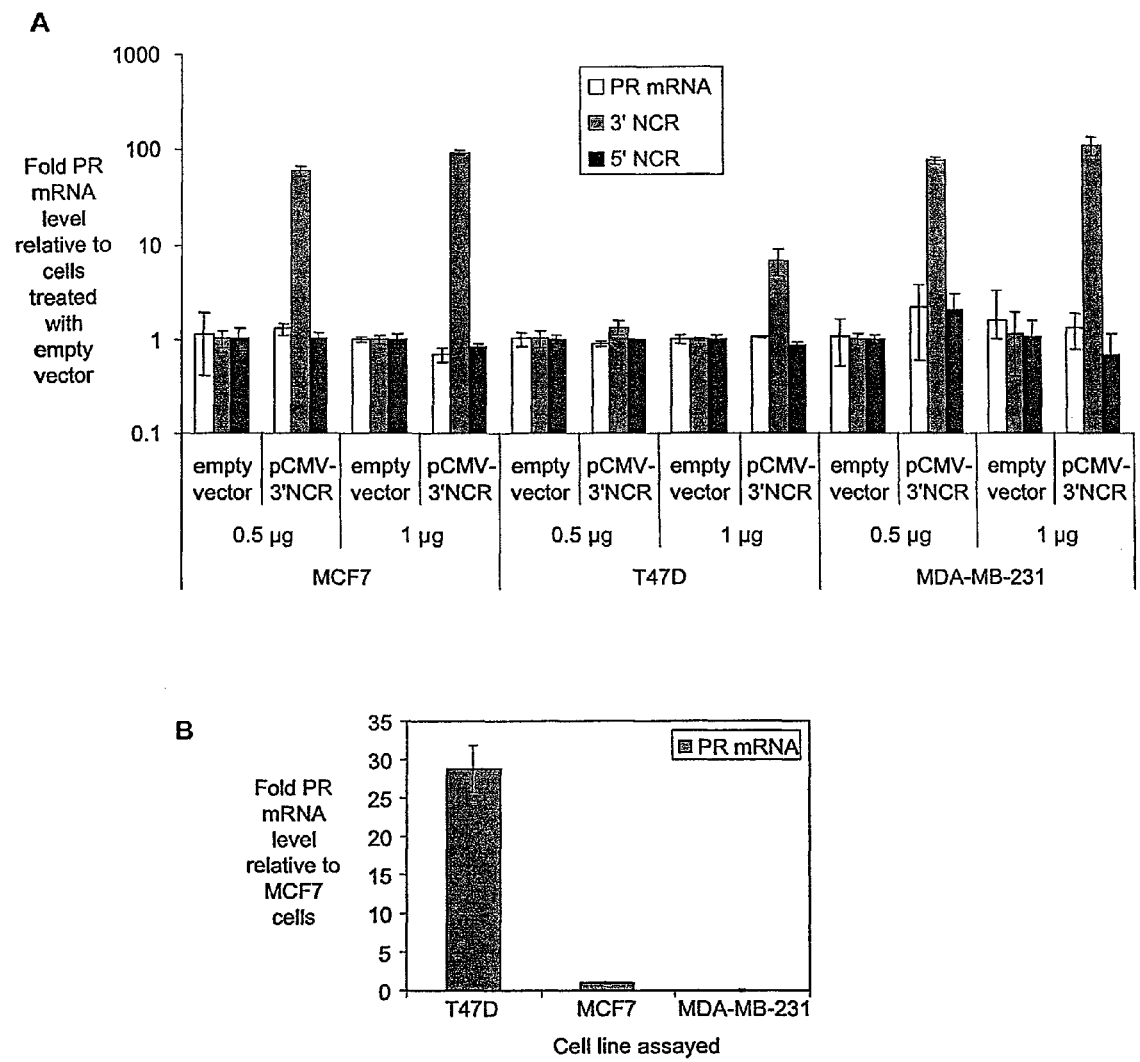
FIGS. 25A-B. Effect of overexpressing the 3' noncoding transcript on expression of transcripts at the PR locus.

To examine the effect of altered cellular levels of the 3' noncoding transcript and PR mRNA, the inventors cloned and overexpressed the 3' noncoding transcript in three breast cancer cell lines with varying basal PR expression levels (T47D-high, MCF7-low, and MDA-MB231-undetectable). Overexpression of the 3' noncoding transcript by as much as 100-fold above endogenous levels did not yield a significant change in PR mRNA levels in any of these three cell lines (FIG. 25). These results suggest that the cellular concentration of 3' noncoding RNA does not affect PR expression.

Gene Looping Brings 5' and 3' Sequences into Proximity.

Modulation of gene transcription by small RNAs complementary to sequences beyond the PR 3'-UTR suggests that recognition of downstream sequences influences activity at gene promoters. This influence must be exerted over a long distance because the genomic locations of the PR promoter and the agRNA target sites are ~100 kB apart. Previous reports suggest that gene promoters and termini can be held in close proximity to one another (O'Sullivan et al., 2004; Tan-Wong et al., 2008; Tiwari et al., 2008). Such proximity might facilitate the modulation of gene expression between otherwise distant 3' and 5' regions.

The inventors investigated whether the promoter and terminal regions of PR might also be in proximity using chromosome conformation capture (3C) analysis (Tan-Wong et al., 2008; Tiwari et al., 2008), a technique that examines the proximity of sequences within chromosomal DNA. In this technique chromosomal DNA is crosslinked, digested with restriction enzyme, and treated with DNA ligase to join DNA ends that are in close proximity. After reversal of crosslinks the DNA is amplified and sequenced to evaluate the proximity of target regions. The inventors amplification of 3C products using multiple primer sets that vary in distance from the 5' promoter and 3' terminal regions of PR (FIG. 7A). For example, amplification by primer T2 (complementary to a sequence beyond the PR 3'-UTR termini) and primer F2 (complementary to sequences within PR exon 1) would only be predicted to occur if the 5' and 3' ends of the PR locus are held in proximity by gene looping.

Figure 26:
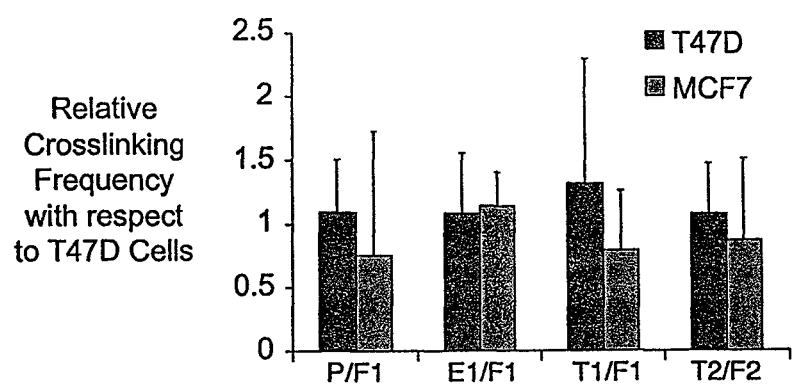
FIG. 26. 3C analysis of the PR locus: Comparing looping in MCF7 versus T47D cells. Crosslinking frequencies are relative to detection of a fixed fragment within genomic DNA for untreated T47D and MCF7 cells. Primer E1 amplifies PR exon 1. Primers T1 and T2 amplify sequences beyond the terminus of PR mRNA. Primers P, E1, F1, F2, T1, and T2 are described in FIG. 7A. Triplicate independent experiments.

The inventors observed that the 5' promoter region of the PR gene was ligated to the 3' terminal regions in T47D (FIG. 7B) and MCF7 (FIG. 7D) cells. Even though expression of PR is much higher in T47D than MCF7 cells, the inventors did not detect a difference in the relative amount of looping (FIG. 26). Addition of inhibitory agRNAs PR13580 or PR-9 to T47D cells (FIGS. 7B-C) or activating agRNAs PR13515 or PR-11 to MCF7 cells (FIGS. 7D-E) did not affect the relative amount of looping at the PR locus.

The inventors also examined the effects of physiologic stimuli on looping. They previously described the effects of adding estrogen, growth of cells in serum-stripped media, treatment with epidermal growth factor (EGF), or adding IL1β decreases on PR expression (FIG. 5). These treatments did not change the relative amounts of gene looping (FIGS. 27 and 28). These data suggest that gene looping at the PR locus remains constant under a range of different cell types, environmental stimuli, and agRNA treatments. It is most likely that the looping is intrachromosomal between the termini of a single PR gene. The inventors are unaware of evidence for interchromosomal contacts between different alleles of the same gene on different chromosomes, but the inventors note that such contacts are possible.

Proximity of 5' and 3' Noncoding Transcripts.

The inventors investigated the possibility that gene looping might allow the 5' and 3' noncoding transcripts to form long distance associations. They used RIP with anti-AGO2 antibodies to examine the proximity of the noncoding transcript at the 3'-UTR to the noncoding transcript at the PR promoter. Addition of inhibitory 3' agRNA PR13580 (FIG. 6E) or activating 3' agRNA PR13515 (FIG. 6F) followed by RIP led to detection of the 5' noncoding transcript. Similarly, addition of duplex agRNAs complementary to the PR promoter, inhibitory agRNA PR-9 (FIG. 6G) and activating agRNA PR-11 (FIG. 6H), led to recovery of the 3'-noncoding transcript. RIP uses a chemical crosslinking step that allows detection of factors within a complex. Therefore, it is not necessary for association between the 3' and the 5' noncoding transcripts to be direct. A more likely explanation is that the association between these noncoding RNAs is indirect. Instead, there is may be a ribonucleoprotein complex containing AGO, and the 5' noncoding and 3' noncoding transcripts. The inventors also observed the same results when using a second anti-AGO antibody (Nelson et al., 2007) (FIGS. 22E-H).

Inhibition of BRCA1 Expression by agRNAs Targeted Beyond the 3'-UTR.

To test whether gene modulation by 3' agRNAs might apply to other genes, The inventors targeted sequences beyond the 3'-UTR of the tumor suppressor breast cancer associated gene 1 (BRCA1). BRCA1 was chosen because: 1) its 3' termini had been well characterized (Smith et al., 2009), 2) its expression is lowered in a significant percentage of human cancers (Miki et al., 1994), 3) it is expressed in T47D breast cancer cells, and 4) the chromosomal loci juxtapose its promoter and termination regions31. 3'-RACE and qPCR confirmed the previously reported35 termination site for BRCA1 mRNA (FIG. 29). 3C analysis confirmed that the BRCA1 promoter and 3' terminal regions are in proximity (FIG. 30).

3' agRNAs inhibited expression of BRCA1 protein, mRNA, and pre-mRNA (FIG. 31) (Supplementary Table 1). BRCA7851 reduced levels of RNAP2 at the BRCA1 promoter. An siBRCA complementary to BRCA1 mRNA (Ma et al., 2006) did not decrease recruitment of RNAP2 to the BRCA1 promoter. The 3' agRNAs did not activate interferon responsive genes (FIGS. 15E-F). These data suggest that 3' agRNAs can also regulate expression of BRCA1.

Potential miRNA Target Sites Occur Downstream from 3'-UTRs.

One explanation for the robust action of 3' agRNAs is that they might be exploiting endogenous regulatory mechanisms that involve microRNAs (miRNAs). To determine whether miRNAs are candidates for recognition of sequences beyond the 3' termini of mRNA the inventors investigated the complementarity of miRNAs with sequences downstream from 3'-UTRs of known genes (FIG. 32). The inventors had previously reported a similar examination for complementarity of miRNAs to gene promoters that revealed substantial sequence matches (Younger et al., 2009).

Gene silencing by miRNAs requires complementarity between the target and the miRNA seed sequence (bases 2-8) (Lewis et al., 2003). Seed sequence matches downstream from gene termini occurred at the same relative frequency as within 3'-UTRs (FIG. 32B). The inventors measured the frequency of seed matches relative to sequence matches that resulted from comparisons with randomizing downstream regions and observed a ~20% increase in seed sequence matches relative to randomized sequences (FIG. 32C). Examination of highly ranked matches revealed many miRNAs with good complementarity to regions downstream from gene termini (FIG. 32A).

The inventors used their computational algorithm to identify miRNAs with complementarity to the portion of the PR 3' noncoding transcript that is downstream from the termination site for PR mRNA (FIG. 8A, FIG. 33). Synthetic miRNAs were synthesized and introduced into T47D cells. miR-193b inhibited expression of PR mRNA when assayed using four different PCR primer sets targeting different regions of PR mRNA (FIG. 8B). miR-193b is encoded within an intergenic region of chromosome 16. It is present in both the nucleus (~40-50%) and cytoplasm of the cell lines used in these studies. The potency of miR-193b to T47D was similar to agRNA PR13580 (FIG. 3B, FIG. 8D). Introduction of mismatches into the region of potential seed sequence complementarity between miR-193b and the 3' noncoding transcript prevented inhibition (FIG. 8E). These results are consistent with a direct interaction at the predicted target site but do not rule out an indirect effect from a seed sequence interaction with some other gene. Comparison of miR-193b and 3' agRNA PR13580 revealed similar effects on levels of the 5' noncoding transcript, PR pre-mRNA, and the 3' noncoding transcript (FIG. 8F). ChIP analysis of cells transfected with miR-193b revealed decreased levels of RNAP2 at the PR promoter (FIG. 8G). These data suggest that miR-193b can act as an inhibitory agRNA by a mechanism similar to designed agRNA PR 13580.

SUPPLEMENTARY TABLE 1

RNAs targeting PR or BRCA1.

| Name | Target site location | Sequence | |
|---|---|---|---|
| *RNAs complementary to the PR promoter* | | | |
| PR-9 | -9/+10 | UGUCUGGCCAGUCCACAGCTT | (SEQ ID NO: 1) |
| PR-11 | -11/+8 | GCUGUCUGGCCAGUCCACATT | (SEQ ID NO: 2) |
| *RNA complementary to the PR 3'-UTR* | | | |
| PR2526 | +2526/+2544 | AGUUGUGCUGCCCUUCCAUTT | (SEQ ID NO: 3) |
| PR3593 | +3593/+3611 | CAUAAUCCUGACCAAAACATT | (SEQ ID NO: 4) |
| *RNAs complementary beyond the PR 3'-UTR* | | | |
| PR13063 | +13063/+13082 | UGUAUUGAGGUUUUAGAUGCTT | (SEQ ID NO: 5) |
| PR13485 | +13485/+13503 | CCUAGUAAUGAAACCAAUGTT | (SEQ ID NO: 6) |
| PR13515 | +13515/+13534 | GUAUAUUUCUAGAGCUAUACTT | (SEQ ID NO: 7) |
| PR13580 | +13580/+13598 | GUUUGCCUGCAUCAGUUCCTT | (SEQ ID NO: 8) |
| miR-634 | | AACCAGCACCCCAACUUUGGACTT | (SEQ ID NO: 9) |
| miR-193b | | AACUGGCCCUCAAAGUCCCGCUTT | (SEQ ID NO: 10) |
| miR-1287 | | UGCUGGAUCAGUGGUUCGAGUCTT | (SEQ ID NO: 12) |
| miR-1265 | | CAGGAUGUGGUCAAGUGUUGUUTT | (SEQ ID NO: 13) |
| *RNA complementary to the BRCA1 protein-encoding RNA* | | | |
| siBRCA | +1416/+1436 | UACAUCAGCUACUUUGGCAUUTT | (SEQ ID NO: 14) |
| *RNAs complementary beyond the BRCA1 3'-UTR* | | | |
| BRCA7209 | +7209/+7227 | AAAGGCUCUGAGAAAGUCGTT | (SEQ IDNO:15) |
| BRCA7324 | +7324/+7342 | UUUGUUUUGGCAGCAACAGTT | (SEQ ID NO: 16) |
| BRCA7851 | +7851/+7869 | CAUCUGUGGAUUAAGCAUGTT | (SEQ ID NO: 17) |
| BRCA7988 | +7988/+8007 | CUCCAUUUUCUCUAUCUUCCTT | (SEQ ID NO: 18) |
| BRCA8870 | +8870/+8888 | GUGGAAAAGUGGGAGGACATT | (SEQ ID NO: 19) |
| BRCA9077 | +9077/+9095 | UGUUGAUGAUUCUGGUUGCTT | (SEQ ID NO: 20) |
| *Mismatch-Containing RNAs* | | | |
| MM | | UCUCUCGCCAGUGCACACCTT | (SEQ ID NO: 21) |
| PR13485_MM3 | | CCUAGUAAUCAAAGCAUUGTT | (SEQ ID NO: 22) |
| PR13515_MM3 | | GUAUAUUUCAAGACCUAAACTT | (SEQ ID NO: 23) |
| PR13515_MM3B | | GUUUAUAUCUUGAGCUAUACTT | (SEQ ID NO: 24) |
| PR13515_MM4 | | GUAUUUUUCAAGACCUAAACTT | (SEQ ID NO: 25) |
| PR13580_MM3 | | GAUUGGCUGGAUCAGUUCCTT | (SEQ ID NO: 26) |
| PR13580_MM4 | | GUUUACCUCCAUGAGUACCTT | (SEQ ID NO: 27) |
| Neg1 | | UCAAGAAGCCAAGGAUAAUTT | (SEQ ID NO: 28) |
| Neg2 | | CAACAUCACUUUAAGGAAGTT | (SEQ ID NO: 29) |
| Neg3 | | UCUCUCGCGAGUCCACAGCTT | (SEQ ID NO: 30) |
| miR-193b-seedMM | | AAACAGCCCUCAAAGUCCCGCUTT | (SEQ ID NO: 31) |
| miR-193b-midMM | | AACUGGCCCUCAACUGCCCGCUTT | (SEQ ID NO: 32) |
| miR-193b-endMM | | AACUGGCCCUCAAAGUCCCAACTT | (SEQ ID NO: 33) |

RNA sequences are listed 5' to 3'. Only one strand of the duplex RNA is shown, corresponding to + strand of genomic DNA. Numbering of target site locations is relative to the +1 transcription start site for PR (NM_000926.4) and BRCA1a (NM_007294.2), respectively.

SUPPLEMENTARY TABLE 2

Primers employed for synthesis of RNA probes in northern blot analysis.

| | | Sequence |
|---|---|---|
| Probe 1 | Forward | 5'-TGG TGT TTG GTC TAG GAT GGA-3' (SEQ ID NO: 34) |
| | Reverse | 5'-TAA TAC GAC TCA CTA TAG GCA CCA TCC CTG CCA ATA TCT-3' (SEQ ID NO: 35) |
| Probe 2 | Forward | 5'-CAC CTT GCT CCT CAT TTC TGA-3' (SEQ ID NO: 36) |
| | Reverse | 5'-TAA TAC GAC TCA CTA TAG GTT CAA ACC ACC AGC CAA TTT-3' (SEQ ID NO: 37) |

SUPPLEMENTARY TABLE 2-continued

Primers employed for synthesis of RNA probes in northern blot analysis.

| | | Sequence |
|---|---|---|
| Probe 3 | Forward | 5'-TCA GGC AAT CAA GTT GAA ACC-3' (SEQ ID NO: 38) |
| | Reverse | 5'-TAA TAC GAC TCA CTA TAG GTT GCC TGC ATC AGT TCC TTA TAG-3' (SEQ ID NO: 39) |
| Probe for Cyclophilin A mRNA | Forward | 5'-CAC CGT GTT CTT CGA CAT TG-3' (SEQ ID NO: 40) |
| | Reverse | 5'-TAA TAC GAC TCA CTA TAG GTC GAG TTG TCC ACA GTC AGC-3' (SEQ ID NO: 41) |

SUPPLEMENTARY TABLE 3

Primes used for qPCR to detect transcript level across PR locus.

| Target Region | | Sequence | |
|---|---|---|---|
| 33-104 | Forward | 5'-CTT GTT GTA TTT GCG CGT GT-3' | (SEQ ID NO: 42) |
| | Reverse | 5'-GCC TCG GGT TGT AGA TTT C-3' | (SEQ ID NO: 43) |
| 102-200 | Forward | 5'-TAC AAC CCG AGG CGG CTA-3' | (SEQ ID NO: 44) |
| | Reverse | 5'-GAA GGG TCG GAC TTC TGC T-3' | (SEQ ID NO: 45) |
| 171-313 | Forward | 5'-GTA CGG AGC CAG CAG AAG TC-3' | (SEQ ID NO: 46) |
| | Reverse | 5'-TCT CTG GCA TCA AAC TCG TG-3' | (SEQ ID NO: 47) |
| 2693-2813 | Forward | 5'-ACT GGA TGC TGT TGC TCT CC-3' | (SEQ ID NO: 48) |
| | Reverse | 5'-CAG GTT GAT CAG TGG TGG AA-3' | (SEQ ID NO: 49) |
| 3439-3518 | Forward | 5'-CGG GCA CTG AGT GTT GAA T-3' | (SEQ ID NO: 50) |
| | Reverse | 5'-CAC CAT CCC TGC CAA TAT CT-3' | (SEQ ID NO: 51) |
| 3501-3619 | Forward | 5'-ATA TTG GCA GGG ATG GTG AA-3' | (SEQ ID NO: 52) |
| | Reverse | 5'-CAA GAC CTC ATA ATC CTG ACC A-3' | (SEQ ID NO: 53) |
| 3584-3663 | Forward | 5'-ATG TCT TTT GTT TTT GGT CAG GA-3' | (SEQ ID NO: 54) |
| | Reverse | 5'-TGA TGT TAT AAA TGT AAG GCT TTC AGA-3' | (SEQ ID NO: 55) |
| 3599-3703 | Forward | 5'-TGG TCA GGA TTA TGA GGT CTT G-3' | (SEQ ID NO: 56) |
| | Reverse | 5'-AAT TAG AAC CTC ACA ATT TTT CTT TT-3' | (SEQ ID NO: 57) |
| 3739-3846 | Forward | 5'-TGT TTT GTT TAC CCA TAT TTT CTT GA-3' | (SEQ ID NO: 58) |
| | Reverse | 5'-TCC TCA CCT ACA TGG TAT GAA A-3' | (SEQ ID NO: 59) |
| 3940-4028 | Forward | 5'-CCC TTT GTG TCA ATT ATA TTT CCA A-3' | (SEQ ID NO: 60) |
| | Reverse | 5'-TGA ATT CCT CCT CAC ACA AAA-3' | (SEQ ID NO: 61) |
| 4273-4422 | Forward | 5'-TGA GGT ATT GCG AGT GGA CA-3' | (SEQ ID NO: 62) |
| | Reverse | 5'-GAG CAA TTG GCA GGA AAG AT-3' | (SEQ ID NO: 63) |
| 4549-4649 | Forward | 5'-TGT TTC AGC CAT GCA AAT CT-3' | (SEQ ID NO: 64) |
| | Reverse | 5'-TTT GGC TGA GTC TCG AAG GT-3' | (SEQ ID NO: 65) |
| 5904-6052 | Forward | 5'-CCA CAG GTT TGG CTT TTG TT-3' | (SEQ ID NO: 66) |
| | Reverse | 5'-CCA TTT GGT GAA GCC ATA TTC-3' | (SEQ ID NO: 67) |
| 7371-7485 | Forward | 5'-CCA GAG CCA TGT GCA TAA GA-3' | (SEQ ID NO: 68) |
| | Reverse | 5'-ATC AGT GGG GAC CAC AGT TG-3' | (SEQ ID NO: 69) |
| 8139-8266 | Forward | 5'-TAA GAA TTT GGG GGT GTT GG-3' | (SEQ ID NO: 70) |
| | Reverse | 5'-AGG AGA ACA AAC CCC TTG GT-3' | (SEQ ID NO: 71) |
| 8959-9086 | Forward | 5'-GCT CAG CAG CTT TCA TTG AT-3' | (SEQ ID NO: 72) |
| | Reverse | 5'-TTC TCC TCC CCC AGA AAA GT-3' | (SEQ ID NO: 73) |
| 12207-12356 | Forward | 5'-TGT GCC TGA CAG TTC TCC TG-3' | (SEQ ID NO: 74) |
| | Reverse | 5'-CCA TGT GCA AAA CAG TCA AAG-3' | (SEQ ID NO: 75) |
| 12604-12714 | Forward | 5'-CAC CTT GCT CCT CAT TTC TGA-3' | (SEQ ID NO: 76) |
| | Reverse | 5'-CCC AGG CAT ACA CAG ATG AA-3' | (SEQ ID NO: 77) |
| 13271-13382 | Forward | 5'-TCA GGC AAT CAA GTT GAA ACC-3' | (SEQ ID NO: 78) |
| | Reverse | 5'-TCA ATG TGA ATA GCC AAA ACA G-3' | (SEQ ID NO: 79) |
| 14354-14445 | Forward | 5'-CAT GTG CGT TGA CAT TCA CA-3' | (SEQ ID NO: 80) |
| | Reverse | 5'-TGA TTC TGA TGG TTG GTG GA-3' | (SEQ ID NO: 81) |

SUPPLEMENTARY TABLE 3-continued

Primes used for qPCR to detect transcript level across PR locus.

| Target Region | | Sequence | |
|---|---|---|---|
| Exon 4/5 | Forward | 5'-TGC AGG ACA TGA CAA CA CAA-3' | (SEQ ID NO: 82) |
| | Reverse | 5'-TAC AGC ATC TGC CCA CTG AC-3' | (SEQ ID NO: 83) |
| Exon 6/7 | Forward | 5'-CCT TAC CAT GTG GCA GAT CC-3' | (SEQ ID NO: 84) |
| | Reverse | 5'-TGT GAG CTC GAC ACA ACT CC-3' | (SEQ ID NO: 85) |
| 14770-14858 | Forward | 5'-CAC TGC ACC TGG CCT AAA CT-3' | (SEQ ID NO: 86) |
| | Reverse | 5'-CCT TGA CCT CCT TTG CTG AA-3' | (SEQ ID NO: 87) |
| 15496-15627 | Forward | 5'-TTC AGC AAA GGA GGT CAA GG-3' | (SEQ ID NO: 88) |
| | Reverse | 5'-CAA TCT GTC CCA TGC AGA AA-3' | (SEQ ID NO: 89) |

SUPPLEMENTARY TABLE 4

Primers used in RACE.

Primers used to identify the 3'-termini of PR mRNA

| | |
|---|---|
| 5'-GGC ACT GGC TGG TAA CAG ATG CAA AAC TG-3' | (SEQ ID NO: 90) |
| 5'-TTG GCA AGA GAT GCA GGG AAT CTT TCT CAT-3' | (SEQ ID NO: 91) |

Primers used to identify the 3' noncoding sense transcript

| | | |
|---|---|---|
| C | 5'-GCA AAG CAA AGA GTG ATT CTC AGG CAA TCA AG-3' | (SEQ ID NO: 92) |
| D | 5'-GCC TAA ATT CTA TAA GGA ACT GAT GCA GGC AAA CC-3' | (SEQ ID NO: 93) |
| B | 5'-TGA TTG CCT GAG AAT CAC TCT TTG CTT TGC TA-3' | (SEQ ID NO: 94) |
| A | 5'-CAC TGT GTA GTT GGT TTC AAC TTG ATT GCC TGA-3' | (SEQ ID NO: 95) |

SUPPLEMENTARY TABLE 5

Primers used to detect PR transcripts.

| Target Region | | Sequence | |
|---|---|---|---|
| 5'-noncoding antisense transcript | Forward | 5'-GGA GGA GGC GTT GTT AGA AA-3' | (SEQ ID NO: 96) |
| | Reverse | 5'-GAA GGG TCG GAC TTC TGC T-3' | (SEQ ID NO: 97) |
| PR Intron | Forward | 5'-CAA AAA GGG TCC GGT GTA GA-3' | (SEQ ID NO: 98) |
| | Reverse | 5'-AGG CAC TGC TCC ACT GTC TT-3' | (SEQ ID NO: 99) |
| 3'-noncoding sense transcript | Forward | 5'-TTC AGA CTA CAT TGG TTT CAT TAC TAG G-3' | (SEQ ID NO: 100) |
| | Reverse | 5'-TTG CCT GCA TCA GTT CCT TAT AG-3' | (SEQ ID NO: 101) |

Primer pair amplifying PR protein-encoding mRNA was designed by Applied Biosystems.

SUPPLEMENTARY TABLE 6

Primers used to define BRCA1 mRNA.

| Target Region | | Sequence | |
|---|---|---|---|
| 5'-promoter | Forward | 5'-GCG CGG GAA TTA CAG ATA AA-3' | (SEQ ID NO: 102) |
| | Reverse | 5'-TAC CCA GAG CAG AGG GTG AA-3' | (SEQ ID NO: 103) |
| BRCA1 pre-mRNA | Forward | 5'-ACC TGC GAA ATC AGA AAC AA-3' | (SEQ ID NO: 104) |
| | Reverse | 5'-TGT GCT GAG CAA GGA TCA TAA-3' | (SEQ ID NO: 105) |
| 3'-flanking region | Forward | 5'-TTC AGA CTA CAT TGG TTT CAT TAC TAG G-3' | (SEQ ID NO: 106) |
| | Reverse | 5'-TTG CCT GCA TCA GTT CCT TAT AG-3' | (SEQ ID NO: 107) |

Primer pair amplifying BRCA1 mRNA was designed by Applied Biosystems.

SUPPLEMENTARY TABLE 7

Primers used in CHIP.

Primers used in RNAP2 CHIP at PR promoter

Forward 5'-GGA GGA GGC GTT GTT AGA AA-3'
(SEQ ID NO: 108)
Reverse 5'-GAA GGG TCG GAC TTC TGC T-3'
(SEQ ID NO: 109)

Primers used in RNAP2 CHIP at BRCA1 promoter (FIG. 8D)

Forward 5'-GCG CGG GAA TTA CAG ATA AA-3'
Reverse (SEQ ID NO: 110)
5'-TAC CCA GAG CAG AGG GTG AA-3'
(SEQ ID NO: 111)

SUPPLEMENTARY TABLE 8

Primers used in FIG. 5.

| Target transcript | | Sequence | |
|---|---|---|---|
| PR mRNA | Forward | 5'-TGC AGG ACA TGA CAA CA CAA-3' | (SEQ ID NO: 112) |
| | Reverse | 5'-TAC AGC ATC TGC CCA CTG AC-3' | (SEQ ID NO: 113) |
| 3' noncoding transcript (3' NCR) | Forward | 5'-TAA GGA ACT GAT GCA GGC AAA-3' | (SEQ ID NO: 114) |
| | Reverse | 5'-AAG CCA AAA ATC CTC CCA AG-3' | (SEQ ID NO: 115) |
| 5' noncoding transcript (5' NCR) | Forward | 5'-CCT AGA GGA GGA GGC GTT GT-3' | (SEQ ID NO: 116) |
| | Reverse | 5'-ATT GAG AAT GCC ACC CAC A-3' | (SEQ ID NO: 117) |

SUPPLEMENTARY TABLE 9

Primers used in RIP (FIG. 6).

| Target Transcript | Direction | Sequence | |
|---|---|---|---|
| 5' noncoding RNA | Forward | 5'-GGA GGA GGC GTT GTT AGA AA-3' | (SEQ ID NO: 118) |
| | Reverse | 5'-GAA GGG TCG GAC TTC TGC T-3' | (SEQ ID NO: 119) |
| 3' noncoding RNA | Forward | 5'-CAGACTACATTGGTTTCATTACTAGG-3' | (SEQ ID NO: 120) |
| | Reverse | 5'-GCATTTATTTTATTTACTAAAGGAGCA-3' | (SEQ ID NO: 121) |
| 3' noncoding RNA | Forward | 5'-TAA GGA ACT GAT GCA GGC AAA-3' | (SEQ ID NO: 122) |
| | Reverse | 5'-AAG CCA AAA ATC CTC CCA AG-3' | (SEQ ID NO: 123) |
| 3' noncoding RNA | Forward | 5'-TTC AGA CTA CAT TGG TTT CAT TAC TAG G-3' | (SEQ ID NO: 124) |
| | Reverse | 5'-TTG CCT GCA TCA GTT CCT TAT AG-3' | (SEQ ID NO: 125) |
| 3' noncoding RNA | Forward | 5'-CCT AGA GGA GGA GGC GTT GT-3' | (SEQ ID NO: 126) |
| | Reverse | 5'-ATT GAG AAT GCC ACC CAC A-3' | (SEQ ID NO: 127) |

SUPPLEMENTARY TABLE 10

Primers used in 3C analysis.

Primers used in 3C analysis of PR

| T2 | 5'-AGTTTAGGCCAGGTGCAGTG-3' (SEQ ID NO: 128) |
|---|---|
| T1 | 5'-TAGCTGATTTGGGCCAGTTT-3' (SEQ ID NO: 129) |
| E4 | 5'-TGTTAATGAGCATTGAACCAGA-3' (SEQ ID NO: 130) |
| E3 | 5'-ATCATCTGCCCCTGTTGAAA-3' (SEQ ID NO: 131) |
| E2 | 5'-TCCTTACCTGTGGGAGCTGT-3' (SEQ ID NO: 132) |

SUPPLEMENTARY TABLE 10-continued

Primers used in 3C analysis.

| E1 | 5'-GGAGAACTCCCCGAGTTAGG-3' (SEQ ID NO: 133) |
|---|---|
| F2 | 5'-GAAGGGTCGGACTTCTGCT-3' (SEQ ID NO: 134) |
| F1 | 5'-TACAACCCGAGGCGGCTA-3' (SEQ ID NO: 135) |
| P | 5'-TCTAACAACGCCTCCTCCTC-3' (SEQ ID NO: 136) |

Primers used in 3C analysis of BRCA1

| D1 | 5'-GGTGCATATAAAATCCTCAGGC-3' (SEQ ID NO: 137) |
|---|---|
| D2 | 5'-GCTCCTCAGCGCCCGGTC-3' (SEQ ID NO: 138) |
| D3 | 5'-GTATTCTTTGACGGGGGGTAG-3' (SEQ ID NO: 139) |
| D4 | 5'-GCTCCATCACTTGAAATGGC-3' (SEQ ID NO: 140) |
| D5 | 5'-CACTGCCCTGTGCTATGTCAA-3' (SEQ ID NO: 141) |
| D7 | 5'-CCAGCCTGGGTGACAGAGC-3' (SEQ ID NO: 142) |
| D9 | 5'-GGCTTGGCCTCAAGAGAATAGCTG-3' (SEQ ID NO: 143) |
| D10 | 5'-CCGGTCATGGTGGTGGACA-3' (SEQ ID NO: 144) |
| D11 | 5'-CATGAGGCCAAAATAAAGGTGTTCG-3' (SEQ ID NO: 145) |

SUPPLEMENTARY TABLE 11

Primers used in Supplementary FIG. S21a.

| Target region | | Sequence | |
|---|---|---|---|
| 6889-6957 | Forward | 5'-ATG ACA GAT CCC ACC AGG AA-3' | (SEQ ID NO: 146) |
| | Reverse | 5'-CAA CAG GGA GCA AAG GAA AA-3' | (SEQ ID NO: 147) |
| 7197-7275 | Forward | 5'-ACT TAG GCC AGC GAC TTT C-3' | (SEQ ID NO: 148) |
| | Reverse | 5'-TAC TAT CAT TAC CCC CAT TT-3' | (SEQ ID NO: 149) |
| 7319-7405 | Forward | 5'-ATT TCC TGT TGC TGC CAA AA-3' | (SEQ ID NO: 150) |
| | Reverse | 5'-GGC CTC ATG AAA CCT GAA AC-3' | (SEQ ID NO: 151) |
| 7402-7464 | Forward | 5'-GGC CAA AAT AAA GGT GTT CG-3' | (SEQ ID NO: 152) |
| | Reverse | 5'-AGA ACT GCA AGG ACC CAG AG-3' | (SEQ ID NO: 153) |

Example 3

Discussion

RNA Recognition Beyond the 3'-UTR.

The inventors data shows that duplex RNAs can modulate transcription by targeting sequences beyond the 3' UTR. These results 1) expand the pool of RNA transcripts that can be targeted by small RNAs; 2) suggest that interactions encoded beyond the 3' UTR can be important; 3) show that RNA-mediated recognition can control transcription over a 100,000 base distance; 4) are consistent with gene looping as an explanation for the long distance control of transcription by RNA; 5) demonstrate that agRNAs can counteract or supplement the effects of physiologic stimuli; 6) suggest that endogenous miRNAs complementary to sequences beyond the 3' termini of genes can regulate gene transcription; and 7) uncover additional layers of regulation and gene structure at the PR locus. agRNAs that target the 5' promoter region have similar effects on gene expression and involve the essential RNA binding protein AGO, suggesting that the mechanisms of 3' agRNAs and 5' agRNAs are related.

Mechanism of 3' agRNAs.

Overexpression of the 3' noncoding RNA does not affect expression of PR (FIG. 25), consistent with the suggestion that the 3' noncoding RNA species becomes involved in the complex prior to dissociation from chromosomal DNA. Proximity of the newly synthesized RNA to the proteins controlling gene transcription would simplify the challenge of initiating gene specific inhibition of transcription by increasing the effective concentration of the RNA relative to genomic DNA. Once noncoding RNA has left the target chromosomal locus it would face greater obstacles returning and forming sequence-selective interactions upon addition of complementary agRNA.

RNA immunoprecipitation data suggest that noncoding RNAs are the direct molecular targets of agRNAs, not sequences within chromosomal DNA. AGO2 appears to play a critical role in the mechanism by promoting binding of the agRNA to the noncoding transcript. After being recruited to the noncoding transcript, AGO2 is available to form interactions with other proteins or disrupt existing interactions. The inventors have previously shown that agRNAs modulate recruitment or displacement of other proteins such as HP1γ and hnRNPk, and also alter histone modifications (Schwartz et al., 2008). A scheme showing a potential orientation of noncoding transcripts, PR genomic DNA, AGO2, and 3' agRNA is presented in FIGS. 9A-B. While AGO2 is the best candidate for involvement and the inventors do not observe cleavage of the target transcript, additional experiments will be needed to fully investigate involvement of AGO1, AGO3, or AGO4 and whether or not the target transcript is cleaved.

How can transcription be affected by an RNA-mediated binding event across 100,000 bases (FIG. 9A)? Three lines of evidence support the conclusion that the PR gene "loops" (i.e., juxtaposes its 3' and 5' termini) (FIG. 9B): 1) striking similarity in the properties of 3' and 5' agRNAs, 2) 3C analysis demonstrating proximity of 5' promoter and 3' terminus regions, and 3) RNA immunoprecipitation showing association of the 3' (24) and 5' noncoding transcripts. Gene looping has been observed at the X-inactivation center (Tsai et al., 2008). The X-inactivation center controls transcriptional inactivation of the X chromosome in females and is regulated by noncoding RNAs Xist, Tsix, and Xite. 3C analysis indicates the loci for these noncoding RNAs are positioned close enough for interactions during the inactivation process and the molecular mechanism may be related to the mechanism of agRNA-mediated gene regulation that the inventors observe.

Similarities to Other Regulators of Transcription.

While the molecular basis for the action of nuclear hormone receptors and other protein regulators is still not completely understood after many years of study, insights into how proteins control transcription provide a framework for broadly understanding the mechanism of agRNAs. Like agRNAs, nuclear hormone receptors recognize specific sequences. For nuclear hormone receptors, ligand binding controls recognition of a coactivator or corepressor protein, while agRNAs recruit AGO2. Endogenous RNA coactivators and transcriptional activators have already been identified (Lanz et al., 1999; Colley and Leedman, 2009; Kuwabara et al., 2004) and it is possible that agRNAs and the agRNA/AGO2 complex may make similar interactions at gene promoters. More generally, many transcription factors have domains that contain RNA binding motifs (Cassiday and Maher, 2002; Kurokawa et al., 2009; D'Orso and Frankel, 2009; Southgate et al., 1990). HIV-1 Tat protein is an especially compelling example because it binds a viral transcript and interacts with other proteins to control transcription (D'Orso and Frankel, 2009; Southgate et al., 1990).

Regulation of gene expression by 3' agRNAs, both activation and inhibition, is robust, suggesting that the mechanism of agRNA-mediated regulation of PR expression shares components with endogenous PR regulation. Consistent with this hypothesis, silencing of CARM-1 or SRC3, proteins known to be critical for regulation of PR by estrogen46, blocked the activity of activating or inhibitory agRNAs PR-11 (Janowski, unpublished).

Both 3' and 5' agRNAs regulate the levels of PR transcripts. Why do the inventors observe activation under some conditions and inhibition under others? Expression of PR is poised to respond to in vivo signals such as hormones, cytokines, and growth factors (Lange et al., 2007). The primary difference between agRNA-mediated activation and repression is that activation is more easily observed in cells that express low basal levels of PR (i.e., cells poised to increase expression) while inhibition is observed in cells that express relatively high amounts of PR (i.e., cells poised to decrease expression). The inventors note that relatively greater PR activation in cells with low basal expression is not restricted to agRNAs.

17β-estradiol also activates PR expression much more robustly in low-PR expressing MCF7 cells than in higher-PR expressing T47D cells. There are many examples of proteins acting as either activators or repressors depending on: 1) context (Willy et al., 2000; Chahrour et al., 2008), 2) binding to accessory proteins (Scsucova et al., 2005; Dubnicoff et al., 1997; Glass et al., 1989; Zhang and Lazar, 2000; Herschberger, 2005), or 3) antagonist/agonist binding (Kraus, 2008). Noncoding RNAs can also either activate or repress transcription through interactions with proteins at promoters possibly through regulating transcriptional coactivator and corepressor complexes (Goodrich and Kugel, 2009).

The transcriptional control machinery can adapt to different stimuli to produce different effects, and this versatility probably underlies the observed mechanism of agRNA action. Conversely, the ability of 3' agRNAs to modulate gene expression over seemingly large genomic distances emphasizes the remarkable diversity of macromolecules and mechanisms affecting transcription and the power of RNA as a genetic regulator.

The foregoing description and examples are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

VII. References

The following references, to the extent that they provide exemplary procedural or other details supplementary to those set forth herein, are specifically incorporated herein by reference:

U.S. Pat. No. 4,981,957
U.S. Pat. No. 5,118,800
U.S. Pat. No. 5,279,721
U.S. Pat. No. 5,319,080
U.S. Pat. No. 5,359,044
U.S. Pat. No. 5,393,878
U.S. Pat. No. 5,446,137
U.S. Pat. No. 5,466,786
U.S. Pat. No. 5,514,785
U.S. Pat. No. 5,519,134
U.S. Pat. No. 5,567,811
U.S. Pat. No. 5,576,427
U.S. Pat. No. 5,591,722
U.S. Pat. No. 5,595,760
U.S. Pat. No. 5,597,909
U.S. Pat. No. 5,610,300
U.S. Pat. No. 5,627,053
U.S. Pat. No. 5,639,873
U.S. Pat. No. 5,646,265
U.S. Pat. No. 5,658,873
U.S. Pat. No. 5,670,633
U.S. Pat. No. 5,672,659
U.S. Pat. No. 5,700,920
U.S. Pat. No. 5,757,994
U.S. Pat. No. 5,788,166
U.S. Pat. No. 5,792,747
U.S. Pat. No. 5,838,002
U.S. Pat. No. 5,902,880
U.S. Pat. No. 5,986,258
U.S. Pat. No. 6,146,886
U.S. Pat. No. 6,268,490
U.S. Pat. No. 6,395,713
U.S. Pat. No. 6,525,191
U.S. Pat. No. 6,531,584
U.S. Pat. No. 6,600,032
U.S. Pat. No. 6,670,461
U.S. Pat. No. 6,770,748
U.S. Pat. No. 6,794,499
U.S. Pat. No. 7,034,133
U.S. Pat. No. 7,053,207
U.S. Pat. No. RE 35,413
U.S. Patent Publn. 2003/0082807
U.S. Patent Publn. 2003/0207841
U.S. Patent Publn. 2004/0014959
U.S. Patent Publn. 2004/0143114
U.S. Patent Publn. 2004/0171570
U.S. Patent Publn. 2004/0219565
U.S. Patent Publn. 2007/0213292
U.S. Patent Publn. 2007/0287831
U.S. Patent Publn. 2008/0015162
U.S. Patent Publn. 2008/0032945
Akhtar et al., *Trends in Cell Bio.*, 2:139, 1992.
Akhtar, In: *Delivery Strategies for Antisense Oligonucleotide Therapeutics*, 1995.
Akinc et al. *Nat. Biotechnol.*, 2008 May; 26(5):561-9, 2008.
Aldrian-Herrada et al., *Nucleic Acids Res.*, 26:4910-16, 1998.
Allerson et al., *J. Med. Chem.*, 48:901-904, 2005.
Altschul et al., *J. Mol. Biol.*, 215(3):403-410, 1990.
Amaral and Mattick, *Mamm. Genome*, 19:454-492, 2008.
Bahr et al., *J. Mass Spectrom.*, 32:1111-1116, 1997.
Barski et al., *Cell*, 129:823-837, 2007.
Bentin and Nielsen, *Biochemistry*, 35:8863-8869, 1996.
Bentzley et al., *Anal Chem.*, 68(13):2141-2146, 1996.
Boado et al. *J. Pharm. Sci.*, 87(11):1308-15, 1998.
Boado, *Adv. Drug Delivery Rev.*, 15:73, 1995.
Braasch et al., *Methods*, 23(2):97-107, 2001.
Bucknall et al., *J. Am. Soc. Mass Spectrom.*, 13(9):1015-1027, 2002.
Caprioli et al., *Anal. Chem.*, 69:4751, 1997.
Cassiday and Maher, *Nucl. Acids. Res.*, 30:4118-4126, 2002.
Chahrour et al., *Science*, 320:1224-1229, 2008.
Chaurand et al., *Anal Chem.*, 71(23):5263-5270, 1999.
Chen et al., *Biomed Chromatogr.*, 15(8):518-24, 2001.
Chen et al., *Fed. of Eur. Biochem Soc.*, 309:115-118, 1992.
Chen et al., *Hum. Gen.*, 120:301-333, 2006a.
Cho et al., *Endocrinology*, 134:658-664, 1994.
Choung et al., *Biochem. Biophys. Res. Commun.*, 342:919-927, 2006.
Chowrira et al., *J. Biol. Chem.*, 269(41):25856-25864, 1994.
Colley and Leedman, *Crit. Reviews Biochem. Mol. Biol.*, 44:25-33, 2009.
Couture et al., *Trends in Genetics*, 12:510, 1996.
D'Orso and Frankel, *Proc. Natl. Acad. Sci. USA*, 106:3101-3106, 2009.
Demidov et al., *Chem Biochem.*, 2:133-139, 2001.
Desiderio et al., *J. Mass Spectrom.*, 35(6):725-733, 2000.

Desiderio et al., *Methods Mol. Biol.*, 61:57-65, 1996.
Dubnicoff et al., *Genes Dev.*, 11:2952-2957, 1997.
Duncan et al., *Rapid Commun. Mass Spectrom.*, 7(12):1090-1094, 1993.
Egholm et al., *Nature*, 365(6446):566-568, 1993.
Elayadi et al., *Nucleic Acids Res.*, 29(8):1683-9, 2001.
Elmen et al., *Nature*, 452(7189):896-9, 2008.
Esau et al. *Cell Metab.*, 3(2):87-98, 2006.
Faruqi et al., *Proc. Natl. Acad. Sci. USA*, 95:1398-1403, 1998.
Faulstich et al., *Anal. Chem.*, 69(21):4349-4353, 1997.
Fenn et al., *Science*, 246(4926):64-71, 1989.
Frieden et al., *Nucle. Nucleo. Nucleic Acids*, 22(5-8):1041-3, 2003.
Geyeregger et al., *Cell. Mol. Life Sci.*, 63:424-539, 2006.
Gingeras, *Genome Res.*, 17:682-690, 2007.
Glass et al., *Cell*, 59:697-708, 1989.
Gobom et al., *Anal. Chem.*, 72(14):3320-3326, 2000.
Goodrich and Kugel, *Crit. Rev. Biochem. Mol. Biol.*, 44:3-15, 2009.
Haeberli et al., *Nucleic Acids Res.*, 33:3965-3975, 2005.
Hall et al., *Nucleic Acids Res.*, 32:5991-6000, 2004.
Hall et al., *Nucleic Acids Res.*, 34:2773-2781, 2006.
Han et al., *Proc. Natl. Acad. Sci. USA*, 104:12422-12427, 2007.
Hassani et al., *J. Gene Med.*, 7(2):198-207, 2005.
He et al., *Science*, 322(5909):1855-7, 2008.
Herschberger et al., *Cancer Res.*, 65:1598-1605, 2005.
Hofland and Huang, *Handb. Exp. Pharmacol.*, 137:165, 1999.
Holstege et al., *EMBO J.*, 16:7468-7480, 1997.
Horak et al., *Rapid Commun. Mass Spectrom.*, 15(4):241-248, 2001.
Hoshika et al., *Nucleic Acids Res.*, 32:3815-3825, 2004.
Ishiwata et al., *Chem. Phare. Bull.*, 43:1005, 1995.
Izant and Weintraub, *Science*, 229:345, 1985.
Janowski et al., *Nat. Chem. Biol.*, 3:166-173, 2007.
Janowski et al., *Nat. Struct. Mol. Biol.*, 13:787-792, 2006.
Janowski et al., *Nature Chem. Biol.*, 1:210-216, 2005b.
Janowski et al., *Nature Chem. Biol.*, 1:216-222, 2005a.
Jespersen et al., *Anal Chem.*, 71(3):660-666, 1999.
Jiang et al., *Biochem. Pharmacol.*, 59:763-772, 2000.
Jolliet-Riant and Tillement, *Fundam. Clin. Pharmacol.*, 13:16, 1999.
Kabarle et al., *Anal. Chem.* 65(20):972A-986A, 1993.
Kahl et al., *J. Mol. Biol.*, 299:75-89, 2000.
Kaihatsu et al., *Biochem.*, 42(47):13996-4003, 2003.
Kaihatsu et al., *Chem. Biol.*, 11:749-758, 2004.
Kanazawa et al., *Biol. Pharm. Bull.*, 22(4):339-346, 1999.
Kapranov et al., *Science*, 316:1484-1488, 2007.
Kapranov, *Nat Rev Genet.*, 8(6):413-23, 2007.
Kashani-Sabet et al., *Antisense Res. Dev.*, 2:3, 1992.
Kaur et al., *Biochemistry*, 45(23):7347-7355, 2006.
Kazmaier et al., *Anesthesiology*, 89(4):831-817, 1998.
Keen et al., *J. Biol. Chem.*, 280:29519-29524, 2005.
Kim et al., *Nat. Struct. Mol. Biol.*, 13:792-797, 2006.
Koshkin and Dunford, *J. Biol. Chem.*, 273(11):6046-6049, 1998.
Koshkin and Wengel, *J. Org. Chem.*, 63(8):2778-2781, 1998.
Kraus, *Curr. Op. Cell Biol.*, 20:294-302, 2008.
Krützfeldt et al., *Nature*, 438:685-689, 2005.
Kumar et al., *Biochem. Pharmacol.*, 55:775-783, 1998.
Kurokawa et al., *RNA Biol.*, 6:3, 2009 (ahead of print)
Kuwabara et al., *Cell*, 19:779-793, 2004.
Lange et al., *Annu. Rev. Physiol.*, 69:171-199, 2007.
Lanz et al., *Cell*, 97:17-27, 1999.
Larsen and Nielsen, *Nucl. Acids Res.*, 24:458-463, 1996.
Lasic et al., *Chem. Rev.* 95:2601, 1995.
Lasic et al., *Science*, 267:1275, 1995.
Lee et al., *ACS Symp. Ser.*, 752:184, 2000.
Lewis et al., *Cell*, 115:787-798, 2003.
Li et al., *Proc. Natl. Acad. Sci. USA*, 102:19231-19236, 2005.
Li et al., *Proc. Natl. Acad. Sci. USA*, 103:17337-17342, 2006.
Liu et al., *J. Biol. Chem.*, 42:24864, 1995.
Liu et al., *Science*, 305:1437-1441, 2004.
Lovelace et al., *J. Chromatogr.*, 562(1-2):573-584, 1991.
Lynn et al., *J. Mol. Evol.*, 48(5):605-614, 1999.
Ma et al., *Mol. Endo.*, 20:14-34, 2006.
Marie et al., *Anal. Chem.*, 72(20):5106-5114, 2000
Maurer et al., *Mol. Membr. Biol.*, 16:129, 1999.
McGarry and Lindquist, *Proc. Natl. Acad. Sci. USA*, 83:399, 1986.
McMahon et al., *Life Sci.*, 71(3):325-3, 2002.
Miketova et al., *Mol. Biotechnol.*, 8(3):249-253, 1997.
Miki et al., *Science*, 266:66-71, 1994.
Mirgorodskaya et al., *Rapid Commun. Mass Spectrom.*, 14(14):1226-1232, 2000.
Misrahi et al., *Biochemistry*, 26(13):3975-3982, 1987.
Mollegaard et al., *Proc. Natl. Acad. Sci. USA*, 91:3892-3895, 1994.
Morita et al., *Nucleic Acids Res. Suppl.*, (2):99-100, 2002
Morris et al., *Science*, 305:1289-1292, 2004.
Muddiman et al., *Fres. J. Anal. Chem.*, 354:103, 1996.
Nardulli et al., *Endocrinology*, 122:935-944, 1988.
Nelson et al., *Rapid Commun. Mass Spectrom.*, 8(8):627-631, 1994.
Nelson et al., *RNA*, 13:1787-1792, 2007.
Nguyen et al., *J. Chromatogr. A.*, 705(1):21-45, 1995.
Nielsen et al., *Science*, 254:1497-1500, 1991.
O'Sullivan et al., *Nat. Genetics*, 36:1014-1018, 2004.
Ohkawa et al., *Nucleic Acids Symp. Ser.*, 27:156, 1992.
Ojwang et al., *Proc. Natl. Acad. Sci. USA*, 89:10802, 1992.
Oku et al., *Biochim. Biophys. Acta*, 1238:86, 1995.
Orum et al., *Curr. Opin. Mol. Ther.*, 3(3):239-43, 2001.
Pardridge et al., *Proc. Natl. Acad. Sci. USA*, 92:5592, 1995.
Paroo and Corey, *Trends Biotechnol.*, 22(8):390-4, 2004.
PCT Appln. WO 2000/53722
PCT Appln. WO 2005/021570
PCT Appln. WO 2005/115481
PCT Appln. WO 2005/121371
PCT Appln. WO 93/23569
PCT Appln. WO 94/02595
PCT Appln. WO 94/14226
PCT Appln. WO 96/10390
PCT Appln. WO 96/10391
PCT Appln. WO 96/10392
PCT Appln. WO 98/39352
PCT Appln. WO 99/14226
Pignon et al., *Hum. Mutat.*, 3: 126-132, 1994.
Prakash et al., *J. Med. Chem.*, 48:4247-4253, 2005.
Rand et al., *Cell*, 123:621-629, 2005.
Remington's Pharmaceutical Sciences, 18th Ed. Mack Printing Company, 1289-1329, 1990.
Remington's Pharmaceutical Sciences, Mack Publishing Co., 1985.
Roepstorff, In: MALDI-TOF Mass Spectrometry Protein Chemistry, Jolles and Jörnvall (Eds.), 1-220, 2000.
Sarver et al., *Science*, 247:1222-1225, 1990.
Scanlon et al., *Proc. Natl. Acad. Sci. USA*, 88:10591-10595, 1991.
Schwartz et al., *Nat. Struct. Mol. Biol.*, 15:842-848, 2008.
Scotto-Lavino et al., *Nat. Protocols*, 1:2555-2562, 2006b.
Scotto-Lavino et al., *Nat. Protocols*, 1:2742-2745, 2006a.
Scsucova et al., *Nucl. Acids. Res.*, 33:2269-2269, 2005.
Singh et al., *Chem. Commun.*, 4:455-456, 1998

Singh et al., *J. Org. Chem.*, 63:10035-10039, 1998.
Siomi and Siomi, *Nature*, 557:396-404, 2009.
Smith et al., *Genome Res.*, 6:1029-1049, 2009.
Southgate et al., *Nature*, 345:640-642, 1990.
Soutschek et al., *Nature*, 432(7014):173-178, 2004.
Stoeckli et al., *Nat. Med.*, 7(4):493-496, 2001.
Stoica et al., *J. Endocrinology*, 165:371-378, 2000.
Summerton & Weller, *Antisense Nucleic Acid Drug Dev.;* 7(3):187-95, 1997.
Sun et al., *Nucleic Acids Res.*, 33:5533-5543, 2005.
Taira et al., *Nucleic Acids Res.*, 19:5125, 1991.
Takach et al., *J. Protein Chem.*, 16:363, 1997.
Tang, *Trends Biochem. Sci.*, 30:106-114, 2004.
Tan-Wong et al., *Proc. Natl. Acad. Sci. USA*, 105:5160-5165, 2008.
The Science and Practice of Pharmacy, 2003.
Thompson et al., *Nature Genet.*, 9:444-450, 1995.
Ting et al., *Nat. Gen.*, 37:906-910, 2005.
Tiwari et al., *PLOS Biology*, 12:2911-2927, 2008.
Tsai et al., *Dev. Biol.*, 319:416-425, 2008.
Tyler et al. *Proc. Natl. Acad. Sci. USA*, 8; 96(12):7053-8, 1999b.
Tyler et al., *Am. J. Physiol.*, 277(6 Pt 1):L1199-204, 1999a.
Urban-Klein, *Gene Ther.*, 12:461-6, 2005.
Ventura et al., *Nucleic Acids Res.*, 21:3249, 1993.
Villanueva et al., *Genes Dev.*, 13:3160-3169, 1999.
Wahlestedt et al., *Proc. Natl. Acad. Sci. USA*, 97:5633-5638, 2000.
Weerasinghe et al., *J. Virol.*, 65:5531, 1991.
Willy et al., *Science*, 290:982-984, 2000.
Wittmann et al., *Biotechnol. Bioeng.*, 72:642, 2001.
Wu et al., *Anal. Biochem.*, 263(2):129-38, 1998.
Wu et al., *Biochem. Biophys. Res. Commun.*, 233(1):221-226, 1997.
Wu et al., *Rapid Commun Mass Spectrom.*, 14(9):756-64, 2000.
Yang et al., *J. Agric. Food Chem.*, 48(9):3990-6, 2000.
Younger et al., *Bioorg. Med. Chem. Lett.*, 19:3791-3794, 2009.
Zaragoza et al., *Biol. Reprod.*, 75:697-704, 2006.
Zhang and Lazar, *Annu. Rev. Physiol.*, 62:439-466, 2000.
Zhang et al., *J. Biol. Chem.*, 275:24436-24443, 2000.
Zhong et al., *Clin. Chem. ACTA.*, 313:147, 2001.
Zweigenbaum et al., *Anal. Chem.*, 71(13):2294-300, 1999.
Zweigenbaum et al., *J. Pharm. Biomed. Anal.*, 23(4):723-733, 2000.

What is claimed is:

1. A method of increasing expression of a progesterone receptor gene in a cell comprising contacting the cell with an oligomer of 10-30 bases in length and comprising SEQ ID NO: 7, thereby increasing expression of the progesterone receptor gene.

2. The method of claim 1, wherein the oligomer is a duplex.

3. The method of claim 2, wherein the duplex is RNA.

4. The method of claim 1, wherein the oligomer is single-stranded.

5. The method of claim 1, wherein the oligomer comprises at least one locked nucleic acid (LNA) base or 2'-O-methyl (2'-O-me) 2'-deoxy, 2'-deoxy-2'-fluoro, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA) base.

6. The method of claim 1, wherein the oligomer is 15-25 bases in length.

7. The method of claim 1, wherein the oligomer is 18-23 bases in length.

8. The method of claim 1, wherein said cell is an isolated cell.

9. The method of claim 1, wherein said cell is located in situ in a host, and contacting comprises administering to the host an amount of the oligomer effective to modulate expression of the progesterone receptor gene.

10. The method of claim 1, further comprising detecting a change in the expression of the progesterone receptor gene.

11. The method of claim 10, wherein detecting comprises inferring a change in the expression of the progesterone receptor gene from a physiologic change in the cell.

12. The method of claim 10, wherein the cell is located in situ in a host and detecting comprises inferring a change in the expression of the progesterone receptor gene from a physiologic change in the host.

13. The method of claim 10, wherein detecting comprises one or more of Northern blot, PCR, immunohistochemistry, Western blot or ELISA.

14. A method of increasing transcription of a progesterone receptor gene in a cell comprising contacting the cell with an oligomer of 10-30 bases in length and comprising SEQ ID NO: 7, thereby increasing transcription of the progesterone receptor gene.

15. A method of decreasing expression of a progesterone receptor gene in a cell comprising contacting the cell with an oligomer of 10-30 bases in length and comprising SEQ ID NO: 6 or 8, thereby decreasing expression of the progesterone receptor gene.

16. The method of claim 15, wherein the oligomer is a duplex.

17. The method of claim 16, wherein the duplex is RNA.

18. The method of claim 15, wherein the oligomer is single-stranded.

19. The method of claim 15, wherein the oligomer comprises at least one locked nucleic acid (LNA) base or 2'-O-methyl (2'-O-me) 2'-deoxy, 2'-deoxy-2'-fluoro, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA) base.

20. The method of claim 15, wherein the oligomer is 15-25 bases in length.

21. The method of claim 15, wherein the oligomer is 18-23 bases in length.

22. The method of claim 15, wherein said cell is an isolated cell.

23. The method of claim 15, wherein said cell is located in situ in a host, and contacting comprises administering to the host an amount of the oligomer effective to modulate expression of the progesterone receptor gene.

24. The method of claim 15, further comprising detecting a change in the expression of the progesterone receptor gene.

25. The method of claim 24, wherein detecting comprises inferring a change in the expression of the progesterone receptor gene from a physiologic change in the cell.

26. The method of claim 24, wherein the cell is located in situ in a host and detecting comprises inferring a change in the expression of the progesterone receptor gene from a physiologic change in the host.

27. The method of claim 24, wherein detecting comprises one or more of Northern blot, PCR, immunohistochemistry, Western blot or ELISA.

28. A method of decreasing transcription of a progesterone receptor gene in a cell comprising contacting the cell with an oligomer of 10-30 bases in length and comprising SEQ ID NO: 6 or 8, thereby decreasing transcription of the progesterone receptor gene.

* * * * *

UNITED STATES PATENT AND TRADEMARK OFFICE
CERTIFICATE OF CORRECTION

| | | |
|---|---|---|
| PATENT NO. | : 8,815,586 B2 | Page 1 of 1 |
| APPLICATION NO. | : 12/766574 | |
| DATED | : August 26, 2014 | |
| INVENTOR(S) | : David R. Corey and Xuan Yue | |

It is certified that error appears in the above-identified patent and that said Letters Patent is hereby corrected as shown below:

In title page, item (56) References Cited - Other Publications, delete the 18th reference on page 2, line 41 "Kim et al., "Argonaute-1 directs siRNA-mediated transcriptional gene silencing in human cells," *Nat. Struct. Mot. Biol.*, 13:793-7, 2006." and replace with --Kim et al., "Argonaute-1 directs siRNA-mediated transcriptional gene silencing in human cells," *Nat. Struct. Mol. Biol.*, 13:793-7, 2006.-- therefor.

In title page, item (56) References Cited - Other Publications, delete the 35th reference on page 2, line 13 "Schwartz el al., "Antisense transcripts are targets for activating small RNAs," *Nat. Struct. Mol. Biol.*, 15:842-8, 2008." and replace with --Schwartz et al., "Antisense transcripts are targets for activating small RNAs," *Nat. Struct. Mol. Biol.*, 15:842-8, 2008.-- therefor.

In title page, item (56) References Cited - Other Publications, delete the 49th reference on page 2, line 49 "Younger el al., "Endogenous small RNA targets gene promoter in mammalian cells," Gordon Research Conference, Salve Regina University, Newport, RI, Jun. 1-6, 2008." and replace with --Younger et al., "Endogenous small RNA targets gene promoter in mammalian cells," Gordon Research Conference, Salve Regina University, Newport, RI, Jun. 1-6, 2008.-- therefor.

In the specification,

Delete the paragraph at column 1, lines 11-14 and replace with --This invention was made with Government support under Grant Nos. GM 77253 and EB 05556 awarded by the National Institutes of Health. The Government has certain rights in the invention.-- therefor.

Signed and Sealed this
Twenty-third Day of December, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,815,586 B2
APPLICATION NO. : 12/766574
DATED : August 26, 2014
INVENTOR(S) : David R. Corey et al.

Page 1 of 1

It is certified that error appears in the above-identified patent and that said Letters Patent is hereby corrected as shown below:

In the Specification

In Column 1, Lines 11-14 delete paragraph and insert:
-- This invention was made with government support under grant numbers GM077253 and EB005556 awarded by The National Institutes of Health. The government has certain rights in the invention. --
therefor.

This certificate supersedes the Certificate of Correction issued December 23, 2014.

Signed and Sealed this
Seventh Day of July, 2020

Andrei Iancu
*Director of the United States Patent and Trademark Office*